United States Patent [19]
Hanafusa et al.

[11] Patent Number: 5,888,763
[45] Date of Patent: Mar. 30, 1999

[54] PEPTIDES SPECIFIC FOR THE FIRST CRK-SH3 DOMAIN

[75] Inventors: Hidesaburo Hanafusa; Beatrice S. Knudsen; Stephan M. Feller; John Kuriyan; Xiaodong Wu; Jie Zheng, all of New York, N.Y.; David Cowburn, Westfield, N.J.

[73] Assignee: The Rockefeller University, New York, N.Y.

[21] Appl. No.: 367,070

[22] Filed: Dec. 30, 1994

[51] Int. Cl.$^6$ .............................. C12P 21/06; C12N 1/20; C07H 21/00
[52] U.S. Cl. ...................... 435/69.1; 435/252.3; 536/23.1
[58] Field of Search ............................. 435/252.3, 320.1, 435/69.1, 325; 536/23.5, 23.1

[56] References Cited

FOREIGN PATENT DOCUMENTS

WO 92/01713  2/1992  WIPO .
WO 9524419  9/1995  WIPO .

OTHER PUBLICATIONS

Afar et al. (1994) Science 264:424–6.
Witte et al. (1981) J. Virol. 39:870–8.
Hullett et al. (1993) Transplant. Proc. 25(1, Book1), pp. 756–757 Abstract only.
Kruh et al. (1990) Proc. Natl. Acad. Sci. USA 87:5802–6.
Fainstein et al. (1989) Oncogene 4:1477–81.
Wu et al. (1995) Structure 3:215–26.
Feller, S.M. (1995) Eur. J. Clin. Pharm. 49:Abst. A150.
Knudsen et al. (1994) J. Biol. Chem. 269:32781–7.
Knudsen et al. (1995) EMBO J. 14:2191–8.
Schumacher et al. (1995) J. Biol. Chem. 270:15341–7.
Baba et al. (1995) J. Immunol. 154:399–412.
Lim et al. (1994) Nature 372:375–9.
Cheadle et al., 1994, J. Biol. Chem. 269:24034–39.
Feller et al., 1994, EMBO J. 13:2341–51.
Feng et al., 1994, Science 266:1241–47.
Finan et al., 1994, J. Biol. Chem. 269:13752–55.
Goudreau et al., 1994, Nature Struct. Biol. 1:898–907.
Lim and Richards, 1994, Nature Structural Biol. 1: 221–25.
Pleiman et al., 1994, Science 263:1609–12.
Ren et al., 1994, Genes Dev. 8:783–95.
Seedorf et al., 1994, J. Biol. Chem. 269:16009–14.
Sparks et al., 1994, J. Biol. Chem. 269:23853–56.
Sumimoto et al., 1994, Proc. Natl. Acad. Sci. USA 91:5345–49.
Tanaka et al., 1994, Proc. Natl. Acad. Sci. USA 91:3443–47.
Terasawa et al., 1994, Nature Struct. Biol. 1:891–97.
Yu et al., 1994, Cell 76: 933–45.
Chardin et al., 1993, Science 260:1338–43.
Egan et al., 1993, Nature 363:45–51.
Gout et al, 1993, Cell 75:25–36.
Olivier et al., 1993, Cell 73:179–91.
Ren et al., 1993, Science 259: 1157–61.
Suen et al., 1993 Mol. Cell. Biol. 13:5500–12.
Cicchetti et al., 1992, Science 257:803–806.
Lowenstein et al., 1992, Cell 70:431–42.
Matsuda et al., 1992, Mol. Cell Biol. 12:3482–89.
Matuoka et al., 1992, Proc. Natl. Acad. Sci. USA 89:9015–19.
Reichman et al., 1992, Cell Growth Diff. 3:451–60.
Mayer et al., 1988, Nature 332:272–75.
Athan asiodis et al. (1990) Nuc. Acids Res. 18:6434 "Complete nucleotide sequence of the PVuII restriction enzyme . . .".

*Primary Examiner*—Robert A. Wax
*Assistant Examiner*—Daniel S. Mytelka
*Attorney, Agent, or Firm*—Klauber & Jackson

[57] ABSTRACT

The present invention relates to regulation and control of cellular processes by SH3-domain binding proteins and peptides. In particular, the invention provides a consensus sequence of a peptide that shows high specificity and affinity for the first SH3 domain of cellular Crk. In specific examples, a number of peptides that contain the consensus are shown to bind c-Crk specifically. The molecular basis for this specificity is examined by crystallography.

10 Claims, 15 Drawing Sheets

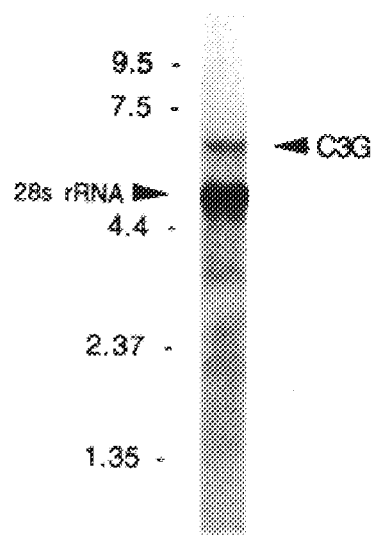

FIG. 1B 9.5 -
7.5 -
28s rRNA ▶
4.4 -
2.37 -
1.35 -

C3G/CB-1    S P P P A L P P K K R Q
C3G/CB-2    D T P P A L P E K K R R
C3G/CB-3    E K P P P L P E K K N K
C3G/CB-4    A P P P A L P P K Q R Q consensus:    P P A L P $^B_P$ K K R v-Crk ▶ c-Crk ▶ c-Crk/CEF v-Crk/3Y1

FIG.8A

| C3G a.a. | | | | | | | | | | | | Inhibition | Kd (μM) |
|---|---|---|---|---|---|---|---|---|---|---|---|---|---|
| CB-1 | 280-291 | | P | P | P | A | L | P | P | K | K | R | | 1.89 ± 0.06 |
| CB-2 | 452-461 | | T | P | P | A | L | P | E | K | K | R | | 14.5 ± 0.6 |
| CB-3 | 539-548 | | K | P | P | L | P | E | K | K | Q | | | 35.8 ± 1.2 |
| CB-4 | 607-616 | | P | P | P | A | L | P | P | K | Q | R | | 4.15 ± 0.25 |
| no peptide | | | | | | | | | | | | | | |

| | 1 | 2 | 3 | 4 | 5 | 6 | 7 | 8 | 9 | 10 | 11 | 12 | binding |
|---|---|---|---|---|---|---|---|---|---|---|---|---|---|
| gst- 1-12 | N | S | P | P | A | L | P | P | K | K | R | | |
| gst- 3-12 | | | P | P | P | A | L | P | P | K | K | R | |
| gst- 4-12 | | | | P | P | A | L | P | P | K | K | R | |
| gst- 3-11 | | | P | P | P | A | L | P | P | K | K | | |
| gst- 5-12 | | | | | P | A | L | P | P | K | K | R | |
| gst- 3-12 P5A, P8A | | | P | P | A | A | L | A | P | K | K | R | |
| gst- 1-12 K10L | | | P | P | P | A | L | P | P | L | K | R | |
| gst- 3-12 R12N | | | P | P | P | A | L | P | P | K | K | N | |
| gst- 4-12 R12N | | | | P | P | A | L | P | P | K | K | N | |

FIG. 17

|  | bbbbbbb | RT loop | bbbbb |  | n-src loop |  | bbbbb | distal | bbbbb | 3₁₀ | bbbb |
|---|---|---|---|---|---|---|---|---|---|---|---|
| Crk-N | AEY VRALFDF | NGNDEEDLPFKKGDI | LRIRD | KP |  | EEQ | WWNAE | DSE G | KRGMI | PV PYV | EKYR |
| v-Crk | VEY VRALFDF | KGNDDGDLPFKKGDI | LKIRD | KP |  | EEQ | WWNAE | DMD G | KRGMI | PV PYV | EKC |
| Crkl | LEY VRTLYDF | PGNDAEDLPFKKGEI | LVIIE | KP |  | EEQ | WWSAR | NKD G | RVGMI | PV PYV | EKL |
| Nck-N | AEEVV VVAKFDY | VAQQELDIKKNER | LWLLD | D |  | SKS | WWRVR | NSM N | KTGFV | PSNYV | ERKN SA |
| Lck | DNL VIALHSY | EPSHDGDLGFEKGEQ | LRILE | Q |  | SGE | WWKAQ | SLTTG | QEGFE | PFNFV | AKA |
| Fyn | VTL FVALYDY | EARTGDDLSFHKGEK | FQILN | SS |  | EGD | WWEAR | SLTTG | ETGYI | PSNYV | APVD |
| Spec | DETGKEL VLALYDY | QEKSPREVTMKKGDI | LTLLN | ST |  | NKD | WWKVE | VN D | RQGFV | PAAYV | KKLD |
| Abl | L FVALYDF | VASGDNTLSITKGEK | LRVLG | YNH |  | NGE | WCEAQ | TKN | GQGWV | PSNYI | TPVN SL |
| Grb2-N | ME AIAKYDF | KATADDELSFKRGDI | LKVLN | EEC |  | DQN | WYKAE | LN G | KDGFI | PKNYI | EMKP HP |
| PI3Kb | MSAEGYQ YRALYDY | KKEREEDIDLHLGDI | LTVNK | GSLVALGFSDGQEARPEEIG | WLNGY | NETTG | ERGDF | PGTYV | EYIG RK | ial Biol. 1: 221). In such a
helix each turn consists of three amino acids. Amino acids
that are three positions apart are therefore oriented coplanar
in space. Ultrastructural analysis of the interaction of a high
affinity, proline-rich binding peptide with the PI3Kp85-a-
SH3 domain demonstrated that two coplanar proline residues form contacts with two grooves on the surface of the
SH3 domain (Yu et al., 1994, Cell 76: 933). These grooves
contain highly conserved aromatic amino acids and are
spaced approximately at a distance of one turn of a polyproline II helix.

PEPTIDES SPECIFIC FOR THE FIRST CRK-SH3 DOMAIN

The research leading to the present invention was supported in part with Grant No. Grant Nos. CA44356 and CA09673 from the National Cancer Institute. Accordingly, the Government may have certain rights in the invention.

FIELD OF THE INVENTION

The present invention relates to regulation and control of cellular processes by SH3-domain binding proteins and peptides, and diagnosis and therapy based on the binding activity of such peptides.

BACKGROUND OF THE INVENTION

Protein-protein interaction is one of the mechanisms of signal transduction processes. One such process involves non-receptor type protein-tyrosine kinases (PTKs) of the Src family, which signal in normal and transformed cells. In recent years, much of the attention has been concentrated on certain specific regions of PTKs, in particular three structural domains, termed SH2 (SH stands for Src homology), SH3, and PH (pleckstrin homology). In addition to the Src family of proteins, these domains are present in a wide variety of proteins implicated in signal transduction processes.

Src Homology 2 and 3 (SH2 and SH3) domains are globular protein modules present in a large variety of functionally distinct proteins (Koch et al., 1991, Science 252: 668; Musacchio et al., 1992, FEBS Lett. 307: 55; Mayer et al., 1993, Trends Cell Biol. 3: 8). They mediate binding events that control the activity and localization of many proteins involved in the transmission of signals from the cell surface to the nucleus. SH2 domains bind to phosphorylated tyrosine residues (Matsuda et al., 1991, Mol. Cell. Biol. 11: 1607; Waksman et al., 1992, Nature 358: 646; Cantley et al., 1991, Cell 64: 281). The specificity of these phosphorylation-dependent interactions is determined by sequences adjacent to the phosphorylated tyrosines and has been extensively analyzed (Songyang et al., 1993, Cell 72: 767; Songyang et al., 1994, Mol. Cell. Biol. 14: 2777; Lee et al., 1994, Structure 2: 423; Birge et al., 1993, Science 262: 1522 (and references therein). In contrast to the abundant data on SH2 domain specificity, the binding specificity of SH3 domains is less well understood.

The presence of SH3 domains in proteins of lower eucaryotes such as S. cervisiae is indicative of the functional importance of SH3 domains throughout evolution. Despite significant sequence diversity, structural comparisons of many SH3 domains show similar folds (Musacchio et al., 1992, Nature 359: 851). The first SH3 binding protein was isolated through its ability to bind to the AblSH3 domain and the sequence responsible for this interaction was localized to a ten amino acid proline-rich fragment (Cicchetti et al., 1992, Science 257: 803; Ren et al., 1993, Science 259: 1157). It has been suggested that proline-rich SH3-binding motifs have a structure similar to that of a polyproline II helix (Lim et al., 1994, Structur The Crk proteins belong to a family of proteins that consist almost entirely of SH2 and SH3 domains, with little intervening sequence. This family presently includes v-Crk (Mayer et al., 1988, Nature 332: 272), two forms of c-Crk proteins, c-Crk-I and c-Crk-II (Reichman et al., 1992, Cell Growth Diff. 3: 451; Matsuda et al., 1992, Mol. Cell Biol. 12: 3482), CRKL (ten Hoeve et al., 1993, Oncogene 8: 2469), Grb2/ASH (Matuoka et al., 1992, Proc. Natl. Acad. Sci. USA 89: 9015; Lowenstein et al., 1992, Cell 70: 431; Suen et al.,1993 Mol. Cell. Biol. 13: 5500) and its homologs Sem5 (Clark et al., 1992, Nature 356: 340) and Drk (Olivier et al., 1993, Cell 73: 179; Simon et al., 1993, Cell 73: 169), Grb3-3 (Fath et al., 1994, Science 264: 971), and Nck (Lehmann et al., 1990 Nucl. Acids Res. 18: 1048). Expression of v-Crk or elevated expression of c-Crk-I leads to cell transformation and increased cellular phosphotyrosine levels (Mats, 16, 18, 28, 29), but the biological role of c-Crk proteins is currently unknown. Since these proteins lack apparent catalytic domains, their function probably lies in their ability to bind specific proteins via their SH2 and SH3 domains. Proteins that interact with the CrkSH2 domain via phosphorylated tyrosine residues have been first identified in cells transformed by v-Crk or v-Src (4, 29, 30). The CrkSH2 domain was shown to preferentially bind phosphotyrosyl-peptides that contain a pTyr-X-X-Pro motif (7, 30). Such a high affinity binding motif is generated upon phosphorylation of c-Crk-II by c-Abl in the spacer region between the two CrkSH3 domains. Binding of the CrkSH2 to this phosphotyrosine residue may regulate c-Crk functions (31).

Src homology 3 (SH3) domains are present on many functionally diverse proteins that are involved in the response of cells to external stimuli (Musacchio et al., 1994, Mol. Cell Biol. 14:5495; Kuriyan and Cowburn, 1993, Curr. Op. Struct. Biol. 3:828–37). The ability of the SH3 domains to bind to short, specific, linear, proline-rich sequences (Cicchetti et al., 1992, Science 257:803) within their binding partners has important functional consequences. SH3 domains may control the cellular localization of their binding partners (Bar-Sagi et al., 1993, Cell 74:83–91); Rotin et al., 1994, EMBO J. 13:4440), determine the substrate specificity of enzymes (Feller et al., 1994, EMBO J. 13:2341–2351) or modulate the catalytic activity of SH3-containing (Liu et al., 1993, Mol. Cell Biol. 13:5225; Mayer and Baltimore, 1994, Mol. Cell Biol. 14:2883), as well as SH3-binding proteins (Gout et al., 1993, Cell 75:25; Pleiman et al., 1994, Science 263:1609). Despite the abundance of SH3 domains within signalling proteins and their potential biological importance, only a few systems are known where SH3 domains play a direct role in physiological or pathological processes. These include genetic systems that demonstrated the crucial role of complex formation between the adaptor protein, Grb2 and the Guanine-nucleotide exchange factor, Son of Sevenless (SOS) (Olivier et al., 1993, Cell 73:179), and two human diseases that involve loss of function mutations of SH3 domains Rawlings et al., 1993, Science 261:358) or their binding sequences (Cheng et al., 1994, Proc. Natl. Acad. Sci. USA 91:8152).

Identification of two proline-rich motifs in the SH3 binding proteins, 3BP1 and 3BP2 was first achieved by expression library screening with the AblSH3 domain (Cicchetti et al., supra). Mutagenesis of the 3BP-1 sequence pointed to the proline residues at positions 2, 5 and 10 that are crucial in the binding to the AblSH3 domain (Ren et al., 1993, Science 259:1157). Proline-rich motifs were subsequently identified in known SH3 targets (Seedorf et al., 1994, J. Biol. Chem. 269:16009; Ren et al., 1994, Genes Dev. 8:783; Tanaka et al., 1994, Proc. Natl. Acad. Sci. USA 91:3443), and found to bind to several SH3 domains with variable affinities (Liu et al., 1993, supra; Gout et al., 1993, supra; Chardin et al., 1993, Science 260:1338). Only one highly selective interaction, the binding of a proline-rich sequence in p47$^{phox}$ to the C-terminal p67$^{phox}$ SH3 domain has been reported (Finan et al., 1994, J. Biol. Chem. 269:13752). More recently, new SH3 binding sequences that are not necessarily found in known proteins have been delineated by screening of combinatorial peptide (Yu et al., 1994, Cell 76:933) and phage display libraries (Cheadle et al., 1994, J. Biol. Chem. 269:24034; Sparks et al., 1994, J. Biol. Chem. 269:23853) and provide valuable information about affinity and specificity requirements for SH3 domains.

Structural and mutational analyses of SH3 domain-peptide complexes from Sem-5, p85α, Abl and Fyn (Lim and Richards, 1994, Nature Structural Biology 1:221; Booker et al., 1993, Cell 73:813; Musacchio et al., 1994, Nature Structural Biology 1:546; Yu et al., 1994, supra) revealed molecular details of interactions between SH3 domains and proline-rich sequences. The SH3 domain core is composed of two perpendicular, antiparallel, 3-stranded β-pleated sheets. The hydrophobic surface contains shallow grooves formed by highly conserved aromatic amino acids which contact the proline-rich peptides. This area interacts with two coplanar proline residues from the SH3 binding motif, which forms a polyproline type II helix (Williamson, 1994, Biochem. J. 297:245–260). A second set of coplanar amino acids in positions next to the two proline residues contacts the hydrophobic surface as well as the highly variable RT and n-Src loops that emerge from the core. Despite the contacts of these four amino acids, the affinities of SH3 domains to their ligands are in the micromolar range (Yu et al., 1994, supra).

The general features of SH3 structure and the interaction with proline-rich peptides are now understood (Kudyan & Cowburn, 1993, Curr. Op. Struct. Biol., 3:828–837, Saraste & Musacchio, 1994, Nature Struct. Biol., 1:835–837). The structures of a number of uncomplexed SH3 domains have been determined and have established a highly conserved fold consisting of two anti-parallel β sheets packed against each other (reviewed in (Kudyan & Cowburn, 1993, Curr. Op. Struct. Biol., 3:828–837)). The discovery that SH3 domains bind to sequences that contain multiple prolines with characteristic PXXP motifs (Cicchetti et al., 1992, Science, 257, 803–806, Ren et al., 1993, Science, 259:1157–1161) was followed by the proposal that the SH3 surface could recognize a polyproline type II helix (Lim & Richards, 1994, Nature Struct. Biol. 1:221–225) and by the determination of the three-dimensional structures of peptide complexes of the p85 SH3 domain by NMR (Yu et al., 1994, Cell, 76:933–945) and the Abl and Fyn SH3 domains by X-ray crystallography, Musacchio et al., 1994, Nature Struct. Biol., 1:546–551). These first structures of SH3 complexes revealed that a conserved set of residues on the SH3 surface provide hydrophobic interactions with sidechains presented by the polyproline type II helix.

In each of these structures, the peptide bound in the same orientation ("plus" orientation). Four papers have recently appeared describing the interaction of proline-rich peptides with the Src SH3 domain (Feng et al., 1994, Science, 266:1241–1247) and with SH3 domains of mammalian Grb2 (Goudreau et al., 1994, Nature Struct. Biol., 1:898–907, Terasawa et al., 1994, Nature Struct. Biol, 1:891–897) and its *C. elegans* homolog Sem-5 (Lim et al., 1994, Nature, 372:375–379). The structures of Src SH3 domain bound to two peptides obtained by selection from a combinatorial library revealed that while one peptide bound in the "plus" orientation, the other bound in the opposite direction ("minus" orientation). The three structures of Grb2/Sem-5 SH3 domains show that the Sos peptides bind in the "minus" orientation. The ability of different prolin-rich peptides to bind in opposite orientations to the same binding sites on the SH3 surface can be understood in terms of the symmetry of the polyproline helix and the specific electrostatic and hydrophobic packing interactions observed in these complexes, and analyses of these structures have led to the enunciation of general rules for prolin-rich peptides binding to SH3 domains (Feng et al., 1994, Science, 266:1241–1247, Lim et al., 1994, Nature, 372:375–379).

In these recent structures of the Src (Feng et al., 1994, Science, 266:1241–1247, Lim et al.) and Grb2/Sem5 (Goudreau et al., 1994, Nature Struct. Biol., 1:898–907, Terasawa et al., 1994, Nature Struct. Biol, 1:891–897, Lim et al., 1994, Nature, 372:375–379) peptide complexes, the orientation of the peptide is determined primarily by electrostatic interactions between arginine residues In the peptide and acidic residues that are localized at one end of the peptide binding surface of the SH3 domains. Many SH3 domains have acidic residues in this region. For example, most SH3 domains have a glutamate or aspartate residue corresponding to Glu 172 in Sew-5 that is observed to hydrogen bond to the arginine residue in the Sos peptide (Lim et al., 1994, Nature, 372:375–379). Likewise, the central interactions via PXXP motifs involve highly conserved hydrophobic residues in the SH3 domains. Consequently, the basis for sequence discrimination between prolin-rich peptides and particular SH3 domains requires further elaboration.

The citation of any reference herein is not an admission that such reference is available as prior art to the instant invention.

SUMMARY OF THE INVENTION

In broadest aspect, the present invention relates to molecules that are capable of modulating intracellular signal transduction, which molecules contain a peptide having a nine amino acid consensus sequence. In particular, the molecules of the invention specifically bind to SH3 domains of Crk family proteins, particularly the first SH3 domain ("CrkSH3(1)", also termed herein "SH3(N)") of c-Crk. In particular, the consensus sequence of 9 amino acids binds to the first SH3 domain of c-Crk with high affinity, e.g., saturable binding, and demonstrates relatively low affinity, e.g., non-saturable binding, with other SH3 domains, such as GrbSH3. Such peptides are termed herein as having a Crk binding (CB) sequence, and hence are termed CB peptides. Accordingly, the molecules of the invention that comprise a CB peptide are referred to as CB molecules (since such molecules will demonstrate c-Crk binding activity). In a preferred aspect, a peptide of the invention binds to the first c-CrkSH3 domain with a $K_d$ of less than 10 μM. In another preferred aspect, a peptide of the invention binds to the Grb2SH3 domain with a $K_d$ of greater than 20 μM. In a futher preferred aspect, a peptide of the invention inhibits binding of c-Crk to a 12-mer fusion peptide with GST having the structure GST-NSPPPALPPKKR (SEQ ID NO:21), preferably by greater than about 65%. In yet a specific embodiment, a peptide of the invention binds to a GST-CrkSH3(1) fusion protein as detected by ELISA or blotting.

The peptides of the present invention include a nine amino acid residue peptide having the consensus sequence; a polypeptide or protein preferably of more than 25 amino acid residues that contains the consensus sequence, which polypeptide or protein is not an intracellular signal transducing polypeptide or protein, or has been modified to abrogate signal transducing activity; a peptide of more than nine amino acid residues, and less than 100 amino acid residues, e.g., from nine to less than 50 amino acid residues, more particularly from nine to less than 25 amino acid residues, and including from about nine to 12 amino acid residues, that contains the disclosed nine amino acid consensus sequence; fusion polypeptides (or fusion proteins) wherein the consensus sequence is fused with a fusion partner protein, e.g., GST or transferrin, and conjugates of such peptides with a carrier molecule, including but not limited to a linear polymer (such as polyethylene glycol, polylysine, etc.), a branched-chain polymer, a lipid, a cholesterol group (such as a steroid), a carbohydrate or oligosaccharide, and a polypeptide.

In its broadest aspect, the consensus sequence is:

X P X ψ P X K X X     (SEQ ID NOS:1–3), wherein ψ is an amino acid selected from the group consisting of leucine (L), isoleucine (I), and valine (V), and X is any amino acid residue.

In a specific embodiment, the sequence is selected from the group consisting of:

P P A L P E K K R     (SEQ ID NO:8)
P P A L P P K K R     (SEQ ID NO:9).

In the specific examples, infra, the following peptides have the consensus sequence:

| | | | | | | | | | | | |
|---|---|---|---|---|---|---|---|---|---|---|---|
| S | P | P | P | A | L | P | P | K | K | R | Q | (SEQ ID NO:4) |
| D | T | P | P | A | L | P | E | K | K | R | R | (SEQ ID NO:5) |
| E | K | P | P | P | L | P | E | K | K | N | K | (SEQ ID NO:6) |
| A | P | P | P | A | L | P | P | K | Q | R | Q | (SEQ ID NO:7) |
| L | Q | A | P | E | L | P | T | K | T | R | T | (SEQ ID NO:10) |
| A | V | S | P | L | L | P | R | K | E | R | G | (SEQ ID NO:11) |
| P | R | L | P | I | L | P | S | K | T | R | T | (SEQ ID NO:12) |
| S | G | S | P | A | L | P | R | K | Q | R | D | (SEQ ID NO:13) |
| | P | P | P | A | L | P | P | K | K | R | | (SEQ ID NO:17) |
| | T | P | P | A | L | P | E | K | K | R | | (SEQ ID NO:18) |
| | K | P | P | P | L | P | E | K | K | Q | | (SEQ ID NO:19) |
| | P | P | P | A | L | P | P | K | Q | R | | (SEQ ID NO:20) |
| N | S | P | P | P | A | L | P | P | K | K | R | (SEQ ID NO:21) |
| | | X | P | A | L | P | P | K | K | R | | (SEQ ID NO:23) |
| | P | P | P | A | L | P | P | K | K | N | | (SEQ ID NO:26) |
| | | P | P | A | L | P | P | K | K | N | | (SEQ ID NO:27) |
| | A | P | P | A | L | P | P | K | K | R | | (SEQ ID NO:28) |
| | P | A | P | A | L | P | P | K | K | R | | (SEQ ID NO:29) |

-continued

| | | | | | | | | | |
|---|---|---|---|---|---|---|---|---|---|
| P | P | P | P | L | P | P | K | K | R | (SEQ ID NO:31) |
| A | P | P | A | L | P | A | K | K | R | (SEQ ID NO:34) |
| A | P | P | A | L | P | P | K | A | R | (SEQ ID NO:36) |
| P | P | P | A | L | P | P | K | K | A | (SEQ ID NO:37) |
| P | P | P | A | L | P | P | K | A | R | (SEQ ID NO:43) |
| P | P | P | A | L | P | P | K | K | K | (SEQ ID NO:44) |

The invention is also directed to nucleic acids for transgenic expression of a peptide that contains the consensus sequence as defined above, or any of the specific sequences set forth above.

In addition to proteins, the invention extends to an antibody that binds to the peptide of the invention. Such antibodies may be polyclonal or monoclonal, and are intended to include single chain, Fv fragments, F(ab) fragments, chimeric antibodies, humanized antibodies, bacterially expressed antibodies, etc. In a specific embodiment, the antibody can inhibit the binding activity of a signal transducing protein, e.g., C3G, to the first SH3 domain of Crk-family proteins. Preferably, the antibody can inhibit binding of a signal transducing protein having the consensus sequence to the first SH3 domain of c-Crk.

The proteins and polypeptides of the invention, and nucleic acids encoding the same, are useful for diagnosis and therapy of a disease or disorder associated with a defect in intracellular signal transduction. For example, the invention relates to a method for treating a disease or disorder associated with a defect in intracellular signal transduction comprising administering an amount of a peptide of the invention into cells of a subject believed to be suffering from a disease or disorder associated with a defect in intracellular signal transduction. Alternatively, the invention relates to introducing an expression vector that expresses a protein or polypeptide containing the consensus sequence into cells of a subject believed to be suffering from a disease or disorder associated with a defect in intracellular signal transduction, wherein the expression control sequence of the expression vector provides for expression in the cell. In particular, the present invention contemplates inhibiting binding of intracellular signalling proteins to the first SH3 domain of c-Crk, e.g., to decrease cellular activation associated with intracellular signalling. Such therapy may be important in the treatment of certain cancers and tumors. Inhibition can also be achieved with neutralizing antibodies and with antisense nucleic acids.

Thus, it is a primary object of the present invention to provide factors for modulation of intracellular signal transduction.

It is a further object of the invention to provide modulators of SH3-mediated signal transduction.

A corollary object of the invention is to inhibit or reverse oncogenic transformation of a cell by inhibiting the signal transduction pathway within the cell.

A related object is to treat a disease or disorder associated with an impairment of signal transduction.

A further object of the invention is to modulate cellular activation by inhibiting binding of intracellular proteins to the first SH3 domain of c-Crk.

These and other objects of the present invention can be better appreciated and understood by reference to the following drawings and detailed description of the invention.

BRIEF DESCRIPTION OF THE DRAWINGS

FIG. 1: C3G sequence and m-RNA. A. Amino acid sequence of C3G (SEQ ID NO:45). The 30 amino acids that may be deleted by alternative splicing are underlined. The proline-rich CrkSH3 binding motifs in the middle of the protein are boxed. The large box at the C-terminus indicates the CDC25 homology domain. B. Northern blot of HeLa cell poly(A)+ RNA probed with a C3G-probe. C. Alignment of the proline-rich CrkSH3 binding sequences in C3G (SEQ ID NOS:4–9).

FIG. 8: Affinities of the four proline-rich sequences in C3G to the CrkSH3(1) domain. C3G derived peptides (CB-1 to CB-4; SEQ ID NOS:17–20) were used to inhibit the binding of the gst-1-12 peptide to c-Crk from lysates of c-Crk overexpressing CEFs at a 1:500 molar ratio of gst-1-12 to peptide. Gst-1-12/c-Crk complexes were precipitated with glutathione-beads, blotted and probed with Crk antiserum. The bottom lane in the autoradiogram from a representative peptide inhibition study shows the amount of Crk precipitated in the absence of competitor peptide competition. Binding affinities of the peptides to gst-CrkSH3(1) were determined by tryptophane fluorescence as described in the Material and Method section of Example 2.

B. Binding of CB-1 gst-fusion peptides to the CrkSH3(1) domain. Wild type or mutant sequences derived from the CB-1 region of C3G (CB-1 peptide and derivatives; SEQ ID NOS:17, 21–27) were expressed as gst-fusion peptides as described under Materials and Methods in Example 2. The numbering of amino acid positions indicated in italic is used throughout Examples 2 and 3. For the SH3 binding assay, 1 µg of gst-fusion peptide was blotted and the blot incubated with $^{35}$S-gst-CrkSH3(1) (35,000 dpm/µg) at a concentration of 2 µg/ml in blocking buffer. After washing the binding of the $^{35}$S-gst-CrkSH3(1) was visualized by autoradiography for 12 h.

Figure 9:
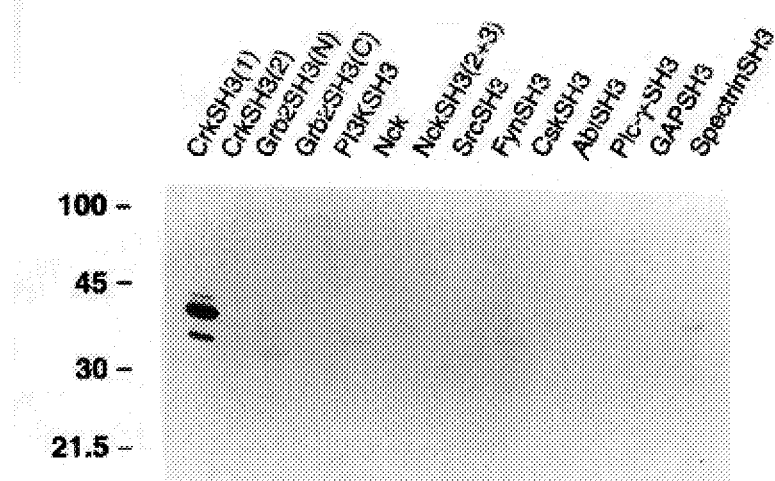

FIG. 9: Binding analysis of a 9 amino acid gst-fusion peptide derived from CB-1 to a panel of SH3 domains. The SH3 domains indicated above each lane were expressed as gst-fusion proteins. One µg gst CrkSH3(1) or equimolar amounts of the other gst-fusion proteins were blotted and probed with a $^{35}$S-gst-4-12. The three day exposure of the autoradiogram in this experiment allowed detection of additional SH3 domains that weakly bound to the 9 amino acid gst-fusion peptide.

Figure 10:
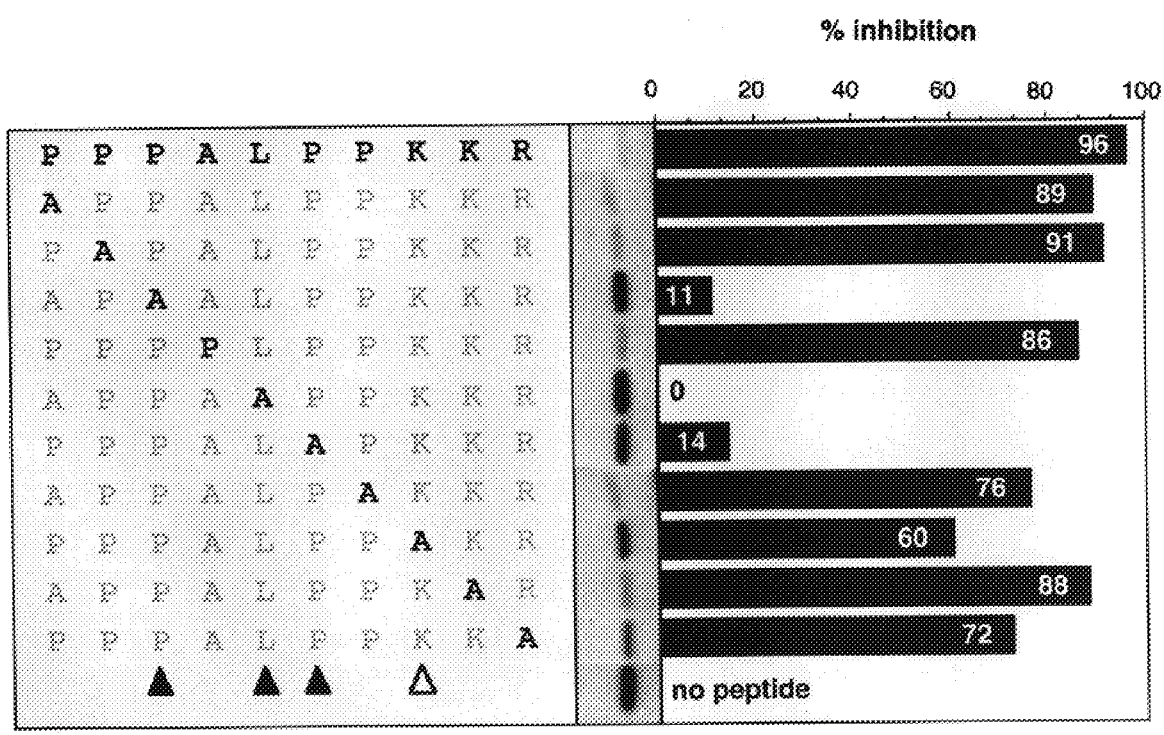

FIG. 10: Alanine scan through the CB-1 peptide. The synthetic peptides shown (SEQ ID NOS:17, 28–37) were used in competition studies as described under Materials and Methods. The filled arrow heads indicate the positions where a mutation to Ala almost entirely abolished the binding. The open arrow head points to the Lys-10Ala mutation that significantly reduced the binding. A representative blot is shown. Each synthetic peptide was used in a 500-fold molar excess to inhibit the binding of 1 µM gst-1-12 to c-Crk from lysates of c-Crk overexpressing CEFs. Gst-1-12/c-Crk complexes were precipitated with glutathione-beads, blotted and detected with the Crk antibody. The last lane represents c-Crk precipitated in the absence of competitor peptide. The autoradiogram of the blot was scanned and the competition for each peptide was indicated as % inhibition of gst-1-12/c-Crk complex formation in the bar graph. Data show one out four representative experiments.

Figure 11:
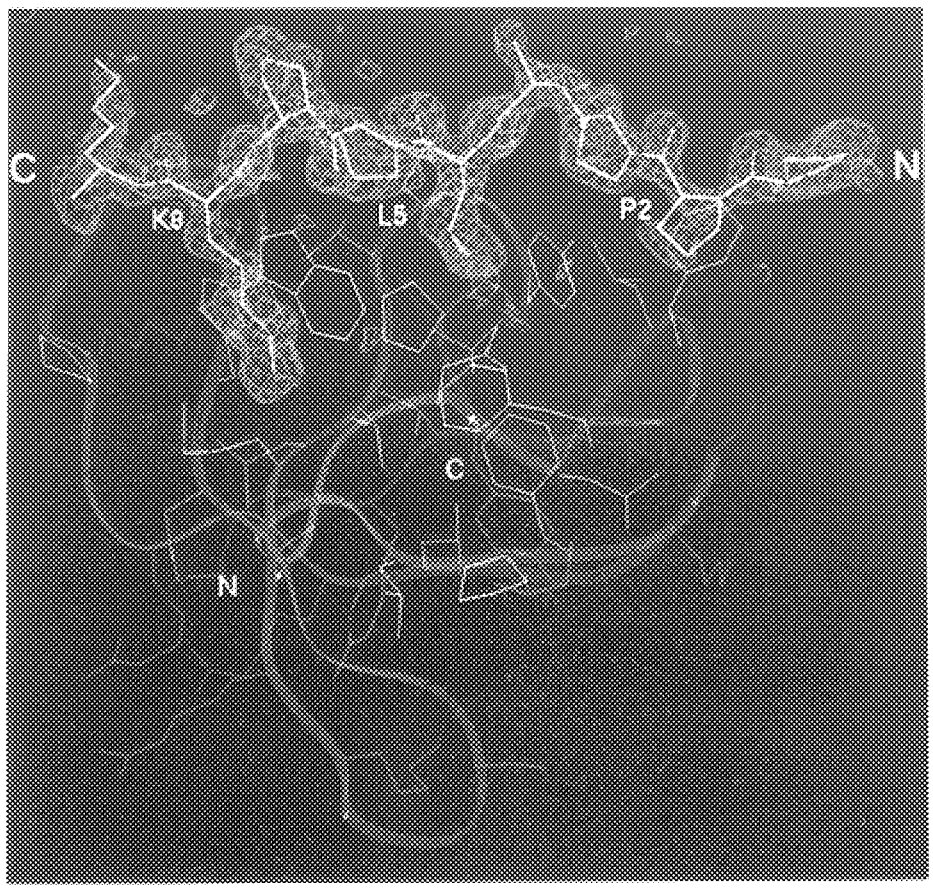

FIG. 11: Difference electron density map for the C36 peptide bound to c-Crk SH3(N). The C3G peptide was removed from the final model of the Crk-C3G complex and an electron density map was calculated using $(F_o-E_c)$ coefficients and model phases, using data between 10.0 and 1.5 Å spacings. One hundred steps of positional refinement without peptide preceded the calculation of the map. Electron density contours at the 2.0 φ (in blue) and 4.0 cφ (in red) levels are shown. The C3G peptide is shown in yellow within the density, with Pro 2, Leu 5 and Lys 8 residues labeled. The backbone of c-Crk SH3-N is represented as a ribbon. Acidic sidechains are red, basic sidechains are blue, polar sidechains are yellow and non-polar sidechains are white.

Figure 12:
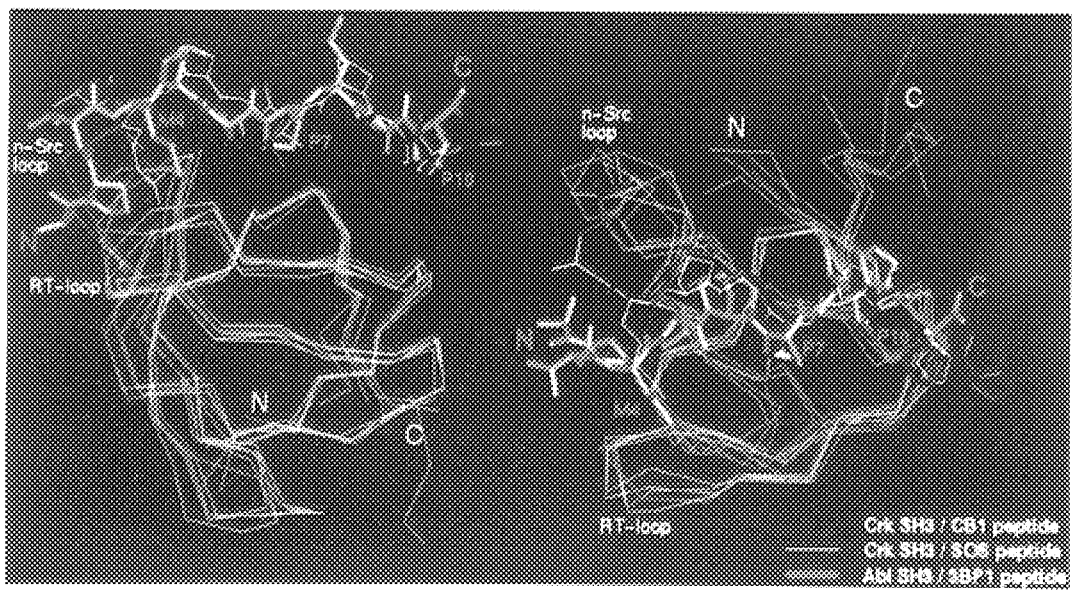

FIG. 12. Comparison of various uncomplexed and peptide complexed SH3 structures determined by X-ray crystallography. The $C^\alpha$ backbone of a number of SH3 domains, aligned by least squares, are shown in this figure. The uncomplexed SH3 domains are from Fyn (Noble et al., 1993, EMBO J., 12:2617–2624), Uk (Eck et al., 1994, Nature, 368:764–769), spectrin (Musacchio et al., 1992, Nature, 359:851–855) and Nck (Wu & Kuriyan, unpublished) (all in yellow) and the three complexed SH3 structures are Crk SH3/C36 (in red), Crk SH3/Sos (in white) and Abl SH3/3BPI (in green, (Musacchio et al., 1994, Nature Struct. Biol., 1:546–551)). To emphasize the reversed orientation of the C3G and Sos peptides with respect to the 3BPI peptide, their N- and C-termini are labelled.

Figure 13:
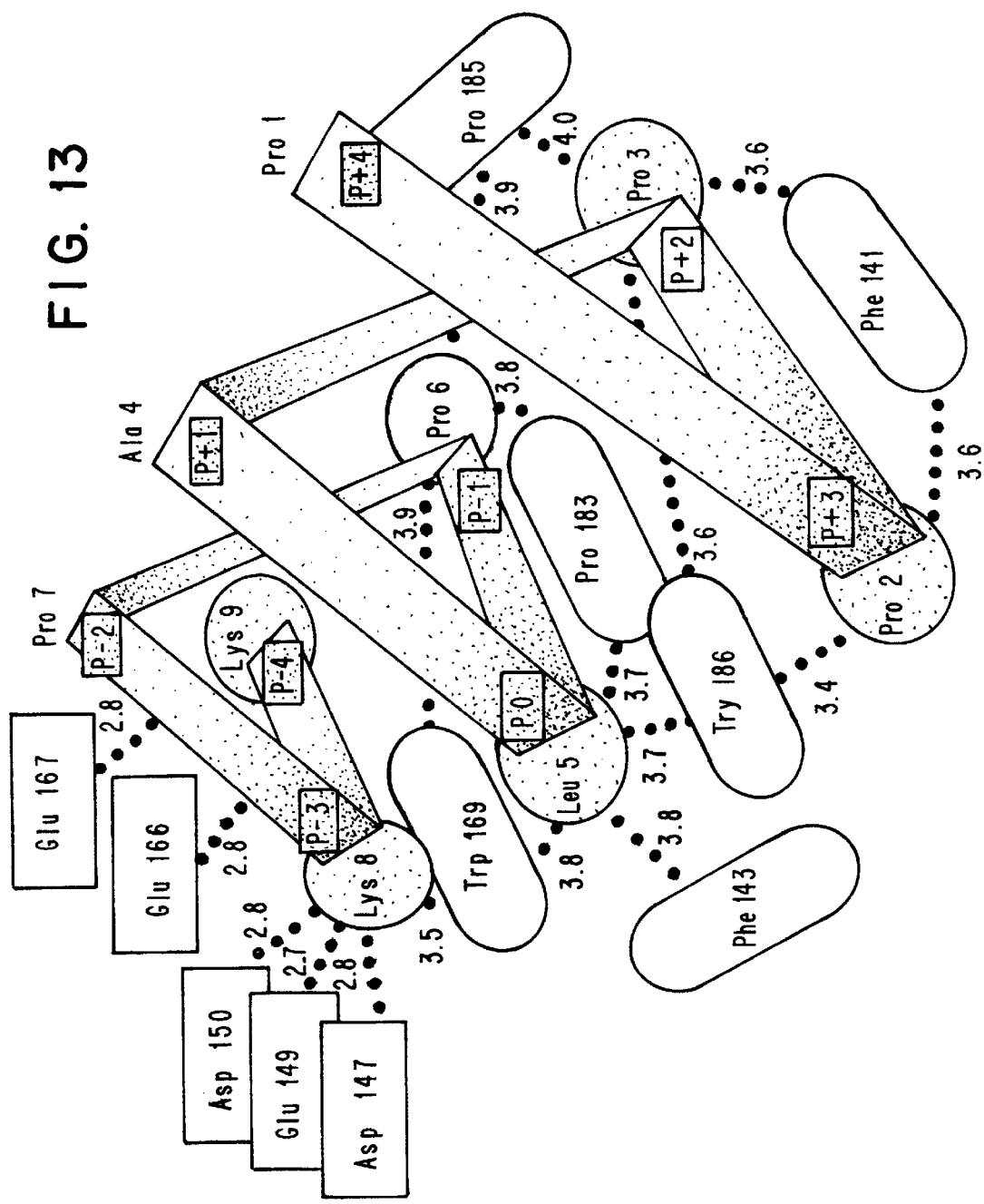

FIG. 13. Schematic diagram showing interactions between the C3G peptide and the c-Crk SH3-N domain. The C3G peptide is represented by the left-handed shaded ribbon, and peptide residues that interact with the SH3 domain are indicated by shaded circles. Residues in c-Crk SH3-N that interact with the peptide are indicated by rounded boxes (for hydrophobic residues) and rectangular boxes (for acidic residues). Distances (in Å) between interacting residues are shown for the nearest pair of carbon atoms (for hydrophobic interactions) and between donor atom and acceptor atom for hydrogen bonds.

Figure 14A:
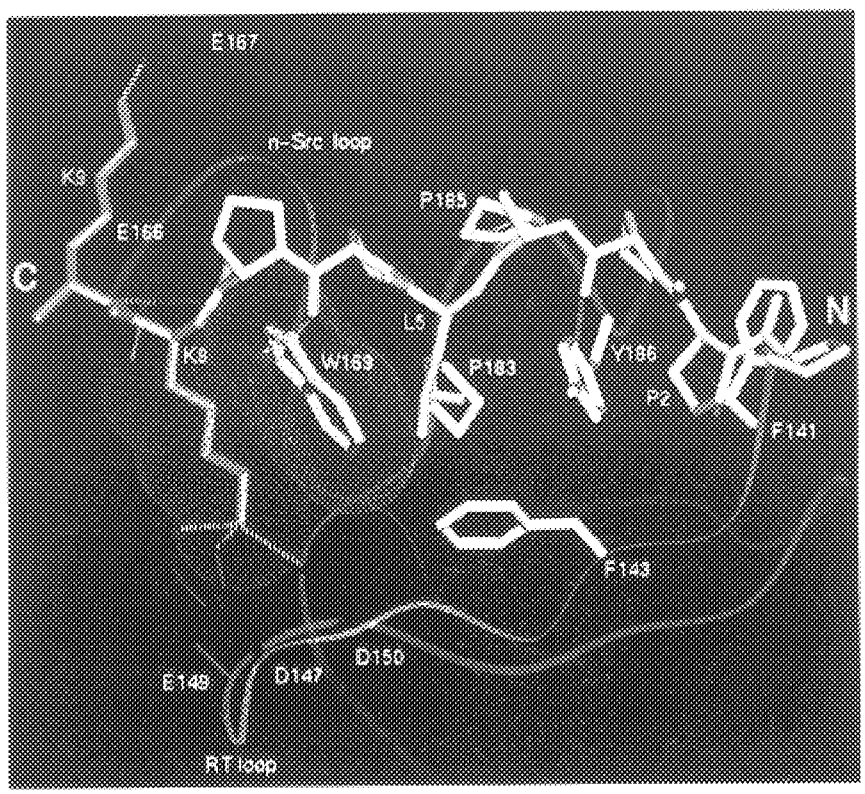
Figure 14B:
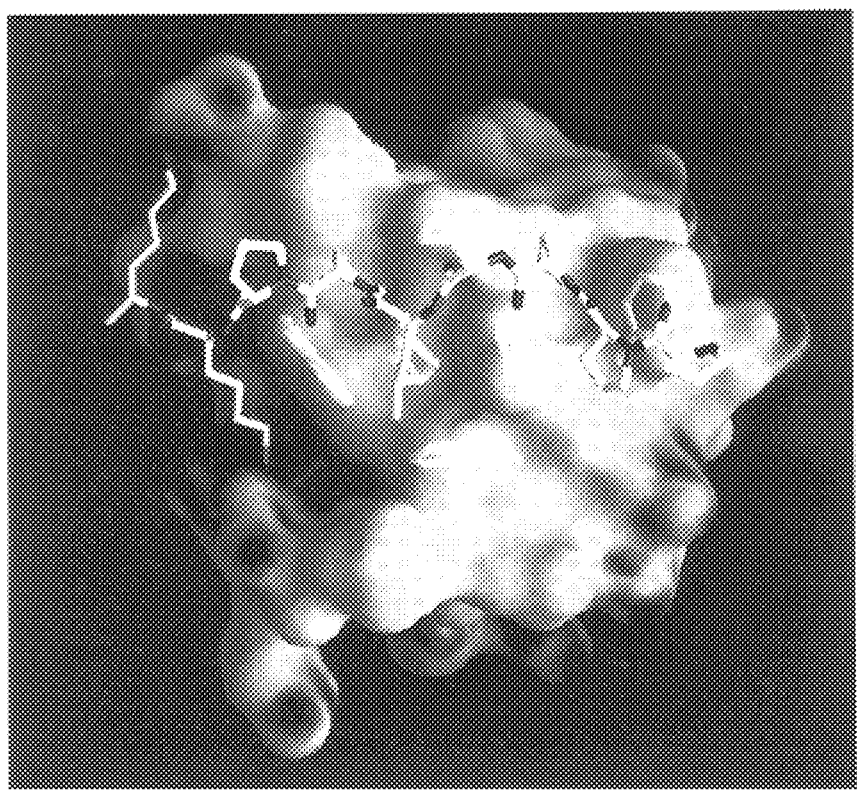

FIG. 14. The interface between c-Crk SH3-N domain and the C3G peptide. Important hydrophobic and polar interactions between c-Crk SH3-N and the C3G peptide. FIG. 14A depicts the polypeptide backbone of the SH3 domain is represented by a green ribbon, and SH3 sidechains that interact with the peptide are colored red for acidic residues and white for hydrophobic residues. The RT-Src and n-Src loops flanking the C-terminal region of the C3G peptide are labeled. The C3G peptide is colored yellow, except for Lys 8 and Lys 9, which are colored blue. The van der Waals surfaces of Lys 8 (in C3G) arid Trp 169 (in Crk) are indicated by small dots. Hydrogen bonds associated with the sidechains of the C3G peptide are indicated by white dashed lines, and hydrogen bonds made to the backbone of C3G are drawn in blue. This figure was generated using QUANTA (Molecular Simulations. Inc.). FIG. 14B depicts the molecular surface of the Crk-C3G complex, calculated with the peptide removed and displayed using GRASP (Nicholls et al., 1991, Proteins: Struct. Funct. and Genetics, 11:281–296). The surface is colored according to the local electrostatic potential calculated in the absence of peptide, assuming a 0.10M NaCl concentration in the solvent. Note the negatively charged pocket (red) surrounding the Lys 8 sidechain of the C3G peptide and the neutral region (white) interacting with Pro 2 to Pro 6 of C3G. The hydrophobic sidechains underneath the SH3 surface are displayed in green. The orientation in (b) is the same as in (a), for ease of identification of the residues.

Figure 15:
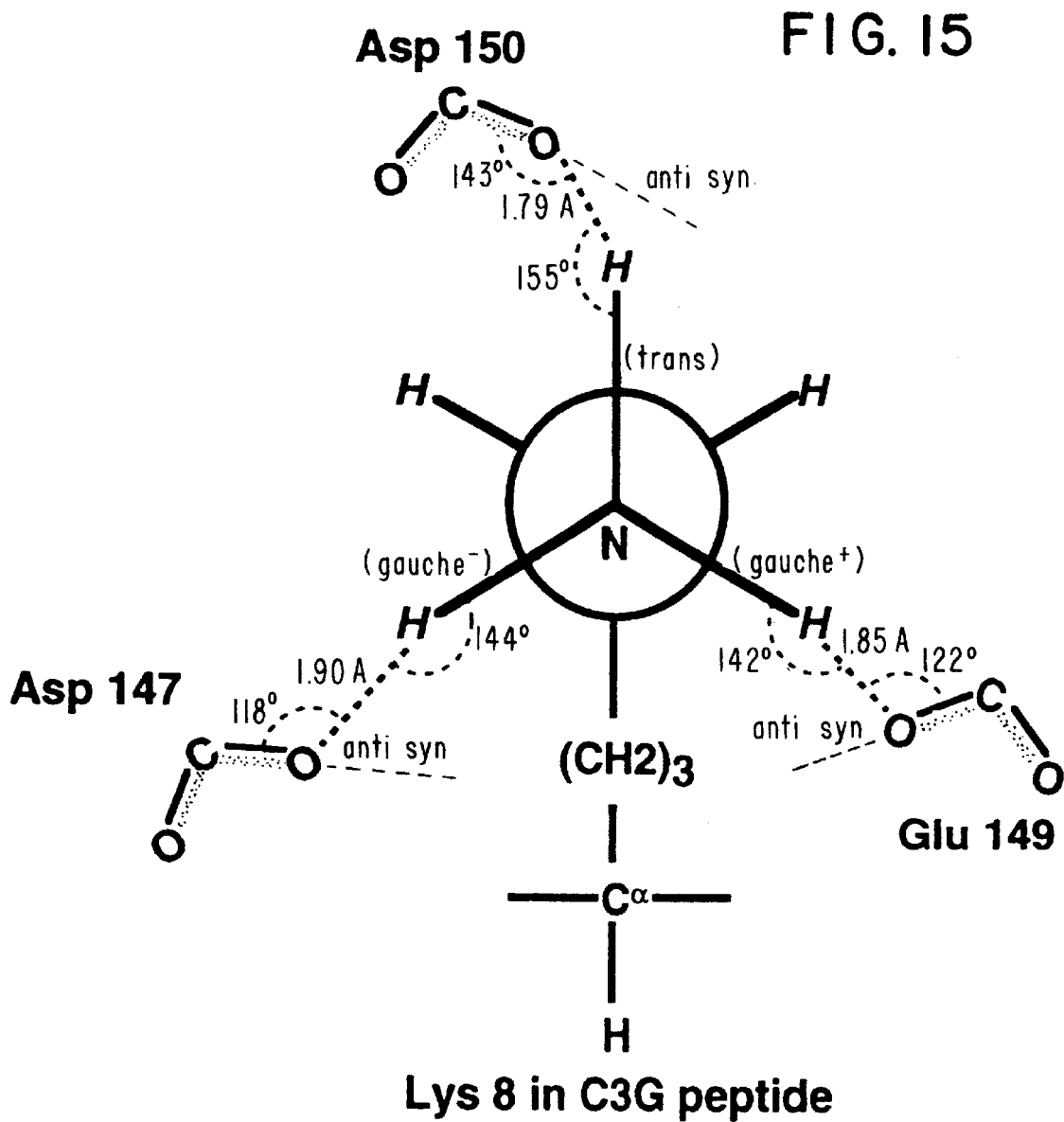

FIG. 15. Schematic diagram of the stereochemistry of the lysine-carboxyl interaction at position P.3. After Ippolito et al. (Ippolito et al., 1990, J. Mol. Biol., 215:457471). The amino group of the lysine is shown in a Newman projection, and the relative disposition of the carboxyl groups and the hydrogen-bonding hydrogens is indicated, for the CrlUC3G complex.

Figure 16:
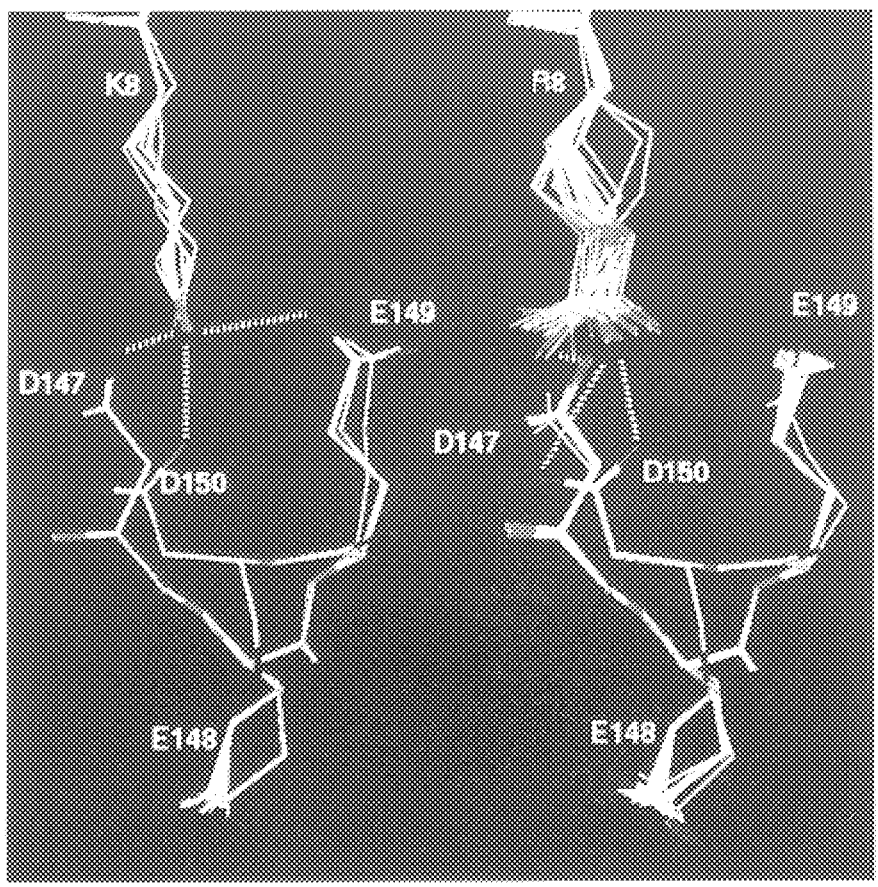

FIG. 16. Results of multiple refinements of the structures of the Crk-C3G and Crk-Sos complexes. To estimate the structural uncertainties associated with the lysine and arginine interactions, the coordinates of residues 147–150 (the RT loop) of Crk SH3 and Lys 8 in C3G peptide (Arg8 in Sos peptide) of the final structure were repeatedly perturbed by random displacements, resulting in an rms deviation of 1.7 A from original model. The resulting structures were independently refined, using data to 1.9 Å for Crk/C3G and Crk/Sos. The results of twenty-four independent refinements are shown for Crk/C3G (left) and Crk/Sos (right). All the structures shown have R-values that are comparable to the original structure (see text). Hydrogen bonds are indicated by dashed lines. Oxygen atoms are colored red, nitrogens blue and carbons white.

FIG. 17. Sequence alignment of several SH3 domains. The sequences of different SH3 domains (SEQ ID NOS:46–55) are aligned based on the secondary structure. The top line provides the notations for secondary structure: "b" for β-sheet and $3^{10}$ for 310 helix. The most highly conserved residues that interact with the ligand are in bold font. Residues that are conserved in many SH3 domains and that interact with the ligand are underlined. The residues in italics represent those that are specific for Crk SH3 and closely related domains.

Figure 18:
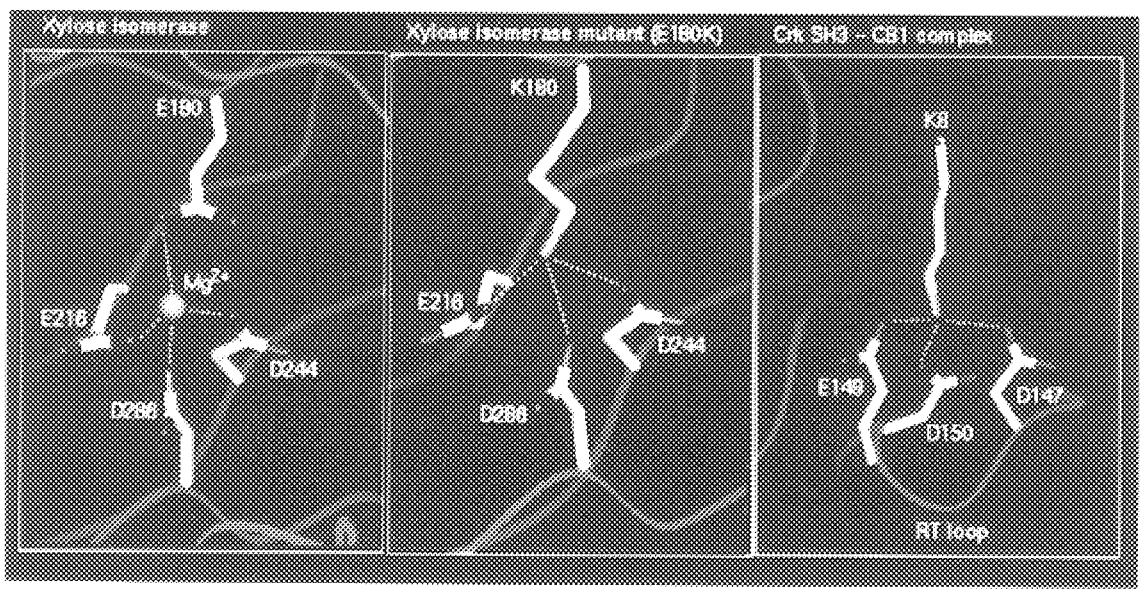

FIG. 18. Comparison of the lysine binding site in Crk to a metal binding site in xylose isomerase. In each of the figures, residues of interest are shown as stick figures, the protein backbone is shown as a ribbon, and hydrogen bonds and metal coordination are indicated by broken lines. (a) The left panel depicts a $Mg^{2+}$ binding site in wild type xylose isomerase (protein databank entry, 1xya, (Allen, K. N., 1994, Biochemistry, 33:1488)). (b) The middle panel shows the lysine-specific interactions in a mutant xylose isomerase, in which the Glu180 was changed to a lysine (entry 1xyl, (Allen, K. N., 1994, Biochemistry, 33:1488)). Both structures of xylose isomerase were determined at 1.8 Å resolution. (c) The panel on the extreme right shows the lysine-specific interactions in the Crk-C3G complex. The red ribbon represents the peptide backbone and the blue ribbon represents the SH3 backbone. Note the extended conformation of the lysine and the fact that it approaches the triad of carboxyl groups from directly above, thus allowing the formation of a more optimal hydrogen-bonding network in Crk-C3G than seen in the xylose isomerase mutant.

DETAILED DESCRIPTION OF THE INVENTION

As noted above, the present invention relates to proteins and polypeptides that are involved in intracellular signal transduction, and CB-molecules capable of modulating intracellualr signal transduction. In particular, the invention provides a consensus amino acid c-CrkSH3(1) binding (CB) sequence that binds with relatively high affinity and specificity to the first c-Crk SH3 domain, and with low relatively affinity to other SH3 domains. Accordingly, the invention provides such peptides of nine or more amino acid residues in length, which can bind to the first c-Crk SH3 domain and inhibit binding of intracellular proteins, e.g., intracellular signalling proteins, to that domain. In a further aspect, the invention relates to nucleic acids, particularly DNA molecules, encoding such proteins and polypeptides. In one aspect, the invention relates to diagnosis of diseases or disorders, employing the polypeptides and nucleic acids of the invention. The invention further relates to modulation of intracellular signal transduction by introducing a peptide of the invention to a subject believed to be in need of modulation. Thus, the invention relates to methods for preparing the peptides and nucleic acids, and pharmaceutical compositions containing the peptides.

To facilitate understanding of the invention, the following terms shall have the definitions set out below.

The term "CB" peptide refers to a peptide having the consensus sequence XPXψPXKXX (SEQ ID NOS:1–3), and preferably the consensus sequence XPXLPXKXX (SEQ ID NO:1).

The term "CB molecule" is used herein to broadly refer to a compound comprising a CB peptide, i.e., containing CB peptide moieties. Thus, the term molecule includes but is not limited to a peptide or polypeptide, particularly a peptide or polypeptide of from nine to less than 100 amino acid residues, from nine to less than 50 amino acid residues, from nine to less than 25 amino acid residues, and from 9 to 12 amino acid residues. The molecules of the invention further include fusion proteins comprising a fusion partner seqence as defined below and the consensus sequence. In a further aspect, a molecule of the invention can be a CB peptide covalently or non-covalently associated with a carrier molecule, such as but not limited to a peptide or protein ligand of a receptor (e.g., a hormone or protein such as transferrin), an antibody or antigen-binding portion thereof, a branched-chain polymer (e.g., as described in U.S. Pat. No. 4,289,872 to Denkewalter et al., issued Sep. 15, 1981; U.S. Pat. No. 5,229,490 to Tam, issued Jul. 20, 1993; and International Patent Publication No. WO 93/21259, published 28 Oct., 1993 by Frechet et al.), a linear polymer (such as polyethylene glycol, polylysine, etc.), a lipid, a cholesterol group (such as a steroid), or a carbohydrate or oligosaccharide.

The term "protein" is used herein to refer to the naturally occurring form of a gene product, both in a pre-processed form (if applicable), and in a post-processed form (also if applicable). The term "polypeptide" is inclusive of the term protein, but also encompasses minor modifications, such as deletions or N- or C-terminal additional amino acid residues to facilitate expression, purification, labeling, stability of the recombinant product, and the like. A "fusion protein" is a chimeric protein comprising a peptide having the CB consensus sequence and a fusion partner. Preferably, the fusion partner protein refers to a protein that is capable of (i) serving as a substrate for proteolytic cleavage (e.g., a Factor Xa sequence); (ii) binding to an antibody specific for the fusion partner protein; (iii) binding to a cognate receptor or a ligand; (iv) interacting ionically or hydrophobically with a chromatographic support; (v) catalyzing a reaction, i.e., enzymatic activity; or (vi) otherwise biologically active as assayed in vitro or in vivo. In a specific example, infra, the fusion partner is GST.

A protein or polypeptide is said to have a "proline-rich motif" when a region of the protein or polypeptide has a disproportionate number of proline residues, including two or more proline residues in tandem, or the consensus sequence PXXP.

The term "consensus sequence" is used herein to refer to a region or domain in a series of proteins or polypeptides that has features in common among all of the proteins or polypeptides. For example, the consensus sequence can be defined by determination that putative consensus segments have a probability of less than 1 in $10^6$, and preferably less than 1 in $10^7$, of matching the alignment by chance as computed on the MoST program. Alternatively, a consensus sequence can be identified by a high degree of homology or sequence similarity between a candidate segment and a consensus segment as defined by the above criteria. In the present invention, the "CB consensus sequence" is characterized by the presence of the sequence XPXLPXKXX (SEQ ID NO:1).

The term "secondary structure" refers to the first level of three-dimensional structure adopted by a protein or polypeptide. Secondary structural elements include the α-helix, β-sheet, β-turn, β-strand, and loop structures. The term "tertiary structure" refers to the three-dimensional arrangement of secondary structural motifs, i.e., the folding of a protein or polypeptide. In the context of the present invention, the location of amino acid residues of the first Crk SH3 domain that contact a CB peptide moiety are determined by the tertiary structure of the domain.

As used herein, the term "functionally active" refers to a polypeptide or protein having sufficient structure to mediate some activity. Such activities may include binding to the first c-CrkSH3 domain with a $K_d$ of less than 10 μM; binding to the Grb2SH3 domain with a $K_d$ of greater than 20 μM; inhibition of binding of c-Crk to a 12-mer fusion peptide with GST having the structure GST-NSPPPALPPKKR (SEQ ID NO:21), preferably by greater than about 65%; and binding to a GST-CrkSH3(1) fusion protein.

Various abbreviations are used herein, which have the following meanings: SH2, Src homology 2 domain; SH3, Src homology 3 domain; C3G, Crk SH3 bindng Guanine-nucleotide releasing factor; CB, Crk binding sequence; gst, glutathione S-transferase; PI3K, phosphatidylinositol 3-kinase; BSA, bovine serum albumin; SDS-PAGE, sodium dodecyl sulfate-polyacrylamide gele electrophoresis; PCR, polymerase chain reaction; OD, optical density; PMSF, phenylmethylsulfonyl fluoride; DTT, dithiothreitol; AU, arbitrary units.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984).

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control. The vector may be a cloning vector, e.g., to propagate the cloned gene, or it may be an expression vector, in which a foreign gene is inserted under control of expression control sequences contained in the vector for heterologous gene expression in a recombinant host cell.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell. A cell has been "transformed" by exogenous or heterologous DNA when the transfected DNA effects a phenotypic change. Preferably, the transforming DNA should be integrated (covalently linked) into chromosomal DNA making up the genome of the cell. However, stable transformation with plasmid (or cosmid) DNA is also possible.

"Heterologous" DNA refers to DNA not naturally located in the cell, or in a chromosomal site of the cell. Preferably, the heterologous DNA includes a gene foreign to the cell.

A "clone" is a population of cells derived from a single cell or common ancestor by mitosis.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules") in either single stranded form, or a double-stranded helix. Double stranded DNA—DNA, DNA-RNA and RNA—RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation. A "complementary" nucleic acid is the opposite strand, e.g., mRNA is complementary to the DNA template, antisense RNA is complementary to sense RNA, and each strand of double-stranded DNA is the complement of the other.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g., 5× SSC, 0.1% SDS, 0.25% milk, and no formamide; or 30% formamide, 5× SSC, 0.5% SDS). Moderate stringency hybridization conditions correspond to a higher $T_m$, e.g., 40% formamide, with 5× or 6× SCC. High stringency hybridization conditions correspond to the highest $T_m$, e.g., 50% formamide, 5× or 6× SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–9.51. For hybridization with shorter nucleic acids, i.e., oligonucleotides, the position of mismatches becomes more important, and the length of the oligonucleotide determines its specificity (see Sambrook et al., supra, 11.7–11.8). Preferably a minimum length for a hybridizable nucleic acid is at least about 10 nucleotides; more preferably at least about 15 nucleotides; most preferably the length is at least about 20 nucleotides.

The term "oligonucleotides" refers to short nucleic acids (including nucleic acids containing phosphate bond mimics, such as thiophosphates) that can be used as primers for PCR, labeled and used as probes, used for site directed mutagenesis, and for other techniques known in the art.

"Homologous recombination" refers to the insertion of a foreign DNA sequence of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

A molecule is "antigenic" when it is capable of specifically interacting with an antigen recognition molecule of the immune system, such as an immunoglobulin (antibody) or T cell antigen receptor. An antigenic polypeptide contains at least about 5, and preferably at least about 10, amino acids. An antigenic portion of a molecule can be that portion that is immunodominant for antibody or T cell receptor recognition, or it can be a portion used to generate an antibody to the molecule by conjugating the antigenic portion to a carrier molecule for immunization. A molecule that is antigenic need not be itself immunogenic, i.e., capable of eliciting an immune response without a carrier.

The term "adjuvant" refers to a compound or mixture that enhances the immune response to an antigen. An adjuvant can serve as a tissue depot that slowly releases the antigen and also as a lymphoid system activator that non-specifically enhances the immune response (Hood et al., *Immunology*, Second Ed., 1984, Benjamin/Cummings: Menlo Park, Calif., p. 384). Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvants such as BCG (bacille Calmette-Guerin) and *Corynebacterium parvum*. Preferably, the adjuvant is pharmaceutically acceptable.

A composition comprising "A" (where "A" is a single protein, DNA molecule, vector, recombinant host cell, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight. It is also preferred that a composition, which is substantially free of contamination, contain only a single molecular weight species having the activity or characteristic of the species of interest.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions, Suitable pharmaceutical carriers are described in "Remington's Pharmaceutical Sciences" by E. W. Martin.

The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host.

The present invention relates to the identification of a previously unidentified consensus sequence for high affinity binding to the first CrkSH3 domain, which is characterized by having a lysine, and preferably at least two basic amino acids, following the proline-X-X-proline motif, and having an amino acid containing a hydrocarbon side chain of at least three carbon atoms, i.e., valine, isoleucine, or leucine, as an amino acid residue between the prolines, adjacent to the second proline; preferably the amino acid is leucine. The preliminary consensus sequence was identified by aligning CrkSH3 binding sequences in C3G and the Abl kinase (Ren et al., 1994, Genes & Dev. 8:783–795) with proline rich sequences of the CrkSH3-binding proteins Sos and Arg (Feller et al., 1995, Methods Enzymol.)

The invention is further based on the discovery, described in the Examples infra, a CB sequence of 9, 10, or 12 amino acids and having an arginine residue at the C-terminus showed the greatest affinity for the first Crk SH3 domain. It was further observed that mutation of the leucine residue in the consensus sequence resulted in a dramateic decrease in the binding affinity, and that mutation of lysine by substitution with leucine dramatically reduces binding affinity, although substitution with alanine results in a less dramatic, if nevertheless significant, reduction in binding affinity. An additional important observation was the specificity for binding to the CrkSH3(1) domain conferred by the lysine residue in the consensus sequence. The importance of this residue was confirmed by crystallographic analysis, which demonstrated that the ε-amino group of lysine interacts with an unusual cluster of three acidic side chain groups in the CrkSH3(1) domain.

The present invention is divided into the following sections, which relate to CB peptides and nucleic acids encoding such peptides; expression of polypeptides or proteins containing a CB peptide in vitro or in vivo; antisense nucleic acids; preparation of CB molecules; antibodies to the CB consensus sequence; diagnostic applications; and therapeutic applications.

CB Peptides and Nucleic Acids

The CB peptides of the invention contain the consensus sequence:

X P X ψ P X K X X    (SEQ ID NOS:1–3), wherein

ψ is an amino acid selected from the group consisting of leucine (L), isoleucine (I), and valine (V), and X is any amino acid residue. Preferably, ψ is leucine.

In a specific embodiment, the sequence is selected from the group consisting of:

P P A L P E K K R    (SEQ ID NO:8)
P P A L P P K K R    (SEQ ID NO:9), with the latter sequence preferred.

In the specific examples, infra, the following peptides have the consensus sequence:

| S | P | P | P | A | L | P | P | K | K | R | Q | (SEQ ID NO:4) |
| D | T | P | P | A | L | P | E | K | K | R | R | (SEQ ID NO:5) |
| E | K | P | P | P | L | P | E | K | K | N | K | (SEQ ID NO:6) |
| A | P | P | P | A | L | P | P | K | Q | R | Q | (SEQ ID NO:7) |
| L | Q | A | P | E | L | P | T | K | T | R | T | (SEQ ID NO:10) |
| A | V | S | P | L | L | P | R | K | E | R | G | (SEQ ID NO:11) |
| P | R | L | P | I | L | P | S | K | T | R | T | (SEQ ID NO:12) |
| S | G | S | P | A | L | P | R | K | Q | R | D | (SEQ ID NO:13) |
|   | P | P | P | A | L | P | P | K | K | R |   | (SEQ ID NO:17) |
|   | T | P | P | A | L | P | E | K | K | R |   | (SEQ ID NO:18) |
|   | K | P | P | P | L | P | E | K | K | Q |   | (SEQ ID NO:19) |
|   | P | P | P | A | L | P | P | K | Q | R |   | (SEQ ID NO:20) |

| | | | | | | | | | | | |
|---|---|---|---|---|---|---|---|---|---|---|---|
| N | S | P | P | P | A | L | P | P | K | K | R | (SEQ ID NO:21) |
| | | | X | P | A | L | P | P | K | K | R | (SEQ ID NO:23) |
| | | P | P | P | A | L | P | P | K | K | N | (SEQ ID NO:26) |
| | | | P | P | A | L | P | P | K | K | N | (SEQ ID NO:27) |
| | | A | P | P | A | L | P | P | K | K | R | (SEQ ID NO:28) |
| | | P | A | P | A | L | P | P | K | K | R | (SEQ ID NO:29) |
| | | P | P | P | P | L | P | P | K | K | R | (SEQ ID NO:31) |
| | | A | P | P | A | L | P | A | K | K | R | (SEQ ID NO:34) |
| | | A | P | P | A | L | P | P | K | A | R | (SEQ ID NO:36) |
| | | P | P | P | A | L | P | P | K | K | A | (SEQ ID NO:37) |
| | | P | P | P | A | L | P | P | K | A | R | (SEQ ID NO:43) |
| | | P | P | P | A | L | P | P | K | K | K | (SEQ ID NO:44). |

In one aspect of the invention, the peptides can be prepared using the well known techniques of solid phase peptide synthesis (the Merrifield synthesis), e.g., using Boc of Fmoc protecting group strategies. Such peptides may contain D- as well as L-amino acids, non-peptidyl bonds, or amino acid analogs and peptidomimetics.

In a further aspect, the invention contemplate synthesis of conformationally constrained peptides. In one embodiment, A constrained, cyclic or rigidized peptide may be prepared provided that in at least two positions in the sequence of the peptide an amino acid or amino acid analog is inserted that provides a chemical functional group capable of crosslinking to constrain, cyclise or rigidize the peptide after treatment to form the crosslink. Cyclization will be favored when a turn-inducing amino acid is incorporated. Examples of amino acids capable of crosslinking a peptide are cysteine to form disulfides, aspartic acid to form a lactone or a lactam, and a chelator such as y-carboxyl-glutamic acid (Gla) (Bachem) to chelate a transition metal and form a cross-link. Protected y-carboxyl glutamic acid may be prepared by modifying the synthesis described by Zee-Cheng and Olson (1980, Biophys. Biochem. Res. Commun. 94:1128–1132). A peptide in which the peptide sequence comprises at least two amino acids capable of crosslinking may be treated, e.g., by oxidation of cysteine residues to form a disulfide or addition of a metal ion to form a chelate, so as to crosslink the peptide and form a constrained, cyclic or rigidized peptide.

The present invention also relates to cloning vectors containing genes encoding a polypeptide or protein, such as a chimeric or fusion protein, that contains the CB consensus sequence. Such a protein or polypeptide can be made by altering encoding nucleic acid sequences by substitutions, additions or deletions that provide for incorporation of the consensus sequence. Preferably, proteins or polypeptides are made that have enhanced or increased functional activity relative to the free peptide of from nine to twelve amino acid residues that contains the consensus sequence.

For example, the present invention contemplates mutating an intracellular protein, e.g., the C3G protein, so that it is functionally inactive with respect to intracellular signal transduction, but contains a CB consensus sequence and binds to the first Crk SH3 domain with high affinity and specificity. Such mutations may be truncation, e.g., by deletion of the C-terminal portion of C3G, or mutation of a domain or region of the protein that mediates functional activity apart from binding to a Crk SH3 domain.

Due to the degeneracy of nucleotide coding sequences, many DNA sequences which encode substantially the same amino acid sequence as a CB consensus sequence can be used in the practice of the present invention. These include but are not limited to nucleotide sequences comprising all or portions of genes which are altered by the substitution of different codons that encode the same amino acid residue within the sequence, thus producing a silent change. Likewise, the derivatives of the invention include, but are not limited to, those containing, as a primary amino acid sequence, all or part of the amino acid sequence of a protein or polypeptide of the invention including altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. It should be noted, however, that substitution of arginine (or histidine) for the consensus lysine residue will result in reduction of the specificity of the recognition of the CB peptide for the first CrkSH3 domain. Similarly, substitutions for the two critical proline residues cannot be tolerated without reduction in binding affinity. Notwithstanding, substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan, and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

The genes encoding derivatives and analogs of the invention can be produced by various methods known in the art. The manipulations which result in their production can occur at the gene or protein level. For example, the cloned gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog, such as with a fusion protein, care should be taken to ensure that the modified gene remains within the same translational reading frame as the gene, uninterrupted by translational stop signals, in the gene region where the desired activity is encoded. Any technique for mutagenesis known in the art can be used, including but not limited to, in vitro site-directed mutagenesis (Hutchinson, C., et al., 1978, J. Biol. Chem. 253:6551; Zoller and Smith, 1984, DNA 3:479–488; Oliphant et al., 1986, Gene 44:177; Hutchinson et al., 1986, Proc. Natl. Acad. Sci. U.S.A. 83:710), use of TAB® linkers (Pharmacia), etc. PCR techniques are preferred for site directed mutagenesis (see Higuchi, 1989, "Using PCR to Engineer DNA", in PCR Technology: Principles and Applications for DNA Amplification, H. Erlich, ed., Stockton Press, Chapter 6, pp. 61–70).

Expression of Proteins and Polypeptides Containing the CB Sequence

The nucleotide sequence coding for a protein or polypeptide containing the CB sequence can be inserted into an appropriate expression vector, i.e., a vector which contains the necessary elements for the transcription and translation of the inserted protein-coding sequence. Such elements are termed herein a "promoter." Thus, the nucleic acid encoding a polypeptide or protein of the invention is operationally (operably) associated with a promoter in an expression vector of the invention. Both cDNA and genomic sequences can be cloned and expressed under control of such regulatory sequences.

An expression vector also preferably includes a replication origin.

The necessary transcriptional and translational signals can be provided on a recombinant expression vector, or they may be supplied by the native gene encoding a polypeptide or protein containing a CB sequence, and/or its flanking regions. However, it should be noted that such polypeptide or protein is modified, e.g., truncated or mutated, to lack signal transducing activity.

Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

A recombinant of the invention, or functional fragment, derivative or analog thereof, may be expressed chromosomally, after integration of the coding sequence by recombination. In this regard, any of a number of amplification systems may be used to achieve high levels of stable gene expression (See Sambrook et al., 1989, supra) can be used.

The cell into which the recombinant vector comprising the nucleic acid encoding the protein or polypeptide is cultured in an appropriate cell culture medium under conditions that provide for expression of the protein or polypeptide by the cell.

Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

Expression of a protein or polypeptide may be controlled by any promoter/enhancer element known in the art, but these regulatory elements must be functional in the host selected for expression. Promoters which may be used to control gene expression include, but are not limited to, the SV40 early promoter region (Benoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); prokaryotic expression vectors such as the β-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25); see also "Useful proteins from recombinant bacteria" in Scientific American, 1980, 242:74–94; promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals.

Expression vectors containing a nucleic acid encoding a protein of the invention can be identified by four general approaches: (a) PCR amplification of the desired plasmid DNA or specific mRNA, (b) nucleic acid hybridization, (c) presence or absence of "marker" gene functions, and (d) expression of inserted sequences. In the first approach, the nucleic acids can be amplified by PCR to provide for detection of the amplified product. In the second approach, the presence of a foreign gene inserted in an expression vector can be detected by nucleic acid hybridization using probes comprising sequences that are homologous to an inserted gene. In the third approach, the recombinant vector/host system can be identified and selected based upon the presence or absence of certain "marker" gene functions (e.g., β-galactosidase activity, thymidine kinase activity, resistance to antibiotics, transformation phenotype, occlusion body formation in baculovirus, etc.) caused by the insertion of foreign genes in the vector. In another example, if the nucleic acid encoding a protein or polypeptide containing a CB consensus sequence is inserted within the marker gene sequence of the vector, recombinants containing the insert can be identified by the absence of the marker gene function. In the fourth approach, recombinant expression vectors can be identified by assaying for the activity of the gene product expressed by the recombinant, provided that the expressed protein assumes a functionally active conformation. Such assays can be based, for example, on the physical or functional properties of the gene product in in vitro assay systems, e.g., binding to a first Crk SH3 domain or alternatively binding with an antibody specific for the CB consensus sequence.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

Vectors are introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267:963–967; Wu and Wu, 1988, J. Biol. Chem. 263:14621–14624; Hartmut et al., Canadian Patent Application No. 2,012,311, filed Mar. 15, 1990).

Recombinant protein can be isolated and purified by standard methods. Generally, the protein or polypeptide, which is expected to be expressed into the cytoplasm, can be obtained by lysing the membrane with detergents, such as but not limited to, sodium dodecyl sulfate (SDS), Triton X-100, nonidet P-40 (NP-40), digoxin, sodium deoxycholate, and the like, including mixtures thereof. Solubilization can be enhanced by sonication of the suspension. Soluble forms of the protein can be obtained by collecting culture fluid, or solubilizing inclusion bodies, e.g., by treatment with detergent, and if desired sonication or other mechanical processes, as described above. The solubilized or soluble protein can be isolated using various techniques, such as polyacrylamide gel electrophoresis (PAGE), chromatography (e.g., ion exchange, affinity, immunoaffinity, and sizing column chromatography), centrifugation, differential solubility, immunoprecipitation, affinity purification by dissociative binding to a CrkSH3(1) column, or by any other standard technique for the purification of proteins.

In yet another specific embodiment, as reported infra, a CB peptide can be expressed as a GST-fusion protein in a bacterial expression system. A cDNA or gene fragment can be isolated, as described above, gel purified, blunt-ended with T4 DNA polymerase, and ligated with linearized, blunt ended PGEX DNA (Smith and Johnson, 1988, Gene 67:31–40). In a specific embodiment, infra, coding sequences for CB peptides were prepared as double stranded oligonucleotides possessing a 5' BamHI and a 3' EcoRI overhang and cloned into a BamHI/EcoRI cut pGEX-2T vector. The correct reading frame and sequence of the oligonuceotides should be checked. The ligation mixture can then be transformed into E. coli and the clones obtained analyzed by restriction digestion and DNA sequencing. Products of resulting plasmids can be purified over glutathione-SEPHAROSE resin and eluted with free glutathione. The glutathione can be removed by passage through a PD10 desalting column.

For expression in insect cell, the invention specifically provides for infection of Sf9 (*Spodoptera frugiperda*) cells at a multiplicity of infection of 10, with a recombinant baculovirus (*Autographa californica*), made by subcloning cDNA into the pAcYM1 vector (Matsuura et al., 1987, J. Gen. Virol. 68:1233–50). After 72 hours, cells can be lysed by Dounce homogenization in TNE buffer, and protein products purified by gel filtration, antibody affinity chromatography, or a combination of chromatography steps.

The peptide, whether produced synthetically or recombinantly, can be analyzed. This is achieved by assays based on the physical or functional properties of the product, including radioactive labelling of the product followed by analysis by gel electrophoresis, immunoassay, etc.

For example, the ability of the expressed protein, or a fragment thereof, to function in an assay, can be determined. In particular embodiments, infra, the binding activity of a putative CB peptide with a CrkSH3(1) domain is assayed by various techniques, including but not limited to inhibition assay, direct binding by blotting, ELISA, fluorescence of the aromatic residues in the CrkSH3 domain, and similar binding analyses. The data obtained can be qualitative, i.e., binding is detected, semi-quantitative, i.e., a particular threshold level of binding is detected, or the relative binding compared to a standard, or quantitative, i.e., determination of binding constant, dissociation constant, affinity constant, etc.

The structure of a consensus peptide, preferably in association with a SH3 domain, can be analyzed by various methods known in the art. Structural analysis can be performed by identifying sequence similarity with other known proteins, as was performed in preliminarily identifying the consensus sequence. The degree of similarity (or homology) can provide a basis for predicting structure and function of a similar domain. In a specific embodiment, sequence comparisons can be performed with sequences found in GenBank, using, for example, the FASTA and FASTP programs (Pearson and Lipman, 1988, Proc. Natl. Acad. Sci. USA 85:2444–48).

The consensus sequence, or the structure of a protein or polypeptide containing the consensus sequence, can be further characterized by a hydrophilicity analysis (e.g., Hopp and Woods, 1981, Proc. Natl. Acad. Sci. U.S.A. 78:3824). A hydrophilicity profile can be used to identify the hydrophobic and hydrophilic regions.

Secondary structural analysis (e.g., Chou and Fasman, 1974, Biochemistry 13:222) can also be done, to identify specific secondary structure of the consensus peptide, particularly in the context of a protein or polypeptide.

Manipulation, translation, and secondary structure prediction, as well as open reading frame prediction and plotting, can also be accomplished using computer software programs available in the art.

By providing an abundant source of recombinant proteins and polypeptides, as well as the 9 to 12 residue peptides, the present invention enables quantitative structural determination of the protein, or domains thereof. In particular, enough material is provided for nuclear magnetic resonance (NMR), infrared (IR), Raman, and ultraviolet (UV), especially circular dichroism (CD), spectroscopic analysis. In particular NMR provides very powerful structural analysis of molecules in solution, which more closely approximates their native environment (Marion et al., 1983, Biochem. Biophys. Res. Comm. 113:967–974; Bar et al., 1985, J. Magn. Reson. 65:355–360; Kimura et al., 1980, Proc. Natl. Acad. Sci. U.S.A. 77:1681–1685). Other methods of structural analysis can also be employed. These include but are not limited to X-ray crystallography (Engstom, A., 1974, Biochem. Exp. Biol. 11:7–13). In a specific embodiment, infra, X-ray crystallography is used to characterize the interaction of a CB consensus peptide with a first Crk SH3 domain.

Computer modeling can also be used, especially in connection with NMR or X-ray methods (Fletterick, R. and Zoller, M. (eds.), 1986, Computer Graphics and Molecular Modeling, in *Current Communications in Molecular Biology*, Cold Spring Harbor Laboratory, Cold Spring Harbor, N.Y.).

Antibodies

According to the invention, a peptide containing a CB consensus domain, or a recombinant proteins or polypeptide containing the CB consensus domain, may be used as an immunogen to generate antibodies which recognize a peptide, protein, or polypeptide that contains the domain. Such antibodies include but are not limited to polyclonal, monoclonal, chimeric, single chain, Fab fragments, and an Fab expression library.

Various procedures known in the art may be used for the production of polyclonal antibodies. For the production of antibody, various host animals can be immunized by injection with the recombinant, or a derivative (e.g., fragment) thereof, including but not limited to rabbits, mice, rats, etc. In one embodiment, a peptide can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward the consensus peptide, any technique which provides for the production of antibody molecules by continuous cell lines in culture may be used. These include but are not limited to the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in *Monoclonal Antibodies and Cancer Therapy*, Alan R. Liss, Inc., pp. 77–96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026–2030) or by transforming human B cells with EBV virus in vitro (Cole et al., 1985, in *Monoclonal Antibodies and Cancer Therapy*, Alan R. Liss, pp. 77–96). In fact, according to the invention, techniques developed for the production of "chimeric antibodies" (Morrison et al., 1984, J. Bacteriol. 159–870; Neuberger et al., 1984, Nature 312:604–608; Takeda et al., 1985, Nature 314:452–454) by splicing the genes from a mouse antibody molecule specific for a λ together with genes from a human antibody molecule of appropriate biological activity can be used; such antibodies are within the scope of this invention. Such human or humanized chimeric antibodies are preferred for use in therapy (described infra), since the human or humanized antibodies are much less likely than xenogenic antibodies to induce an immune response, in particular an allergic response, themselves.

According to the invention, techniques described for the production of single chain antibodies (U.S. Pat. No. 4,946,778) can be adapted to produce specific single chain antibodies. An additional embodiment of the invention utilizes the techniques described for the construction of Fab expression libraries (Huse et al., 1989, Science 246:1275–1281) to allow rapid and easy identification of monoclonal Fab fragments with the desired specificity.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment; and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

The foregoing antibodies can be used in methods known in the art relating to the localization and activity of their binding partners, e.g., for Western blotting, imaging, measuring levels thereof in appropriate physiological samples, etc.

In a specific embodiment, antibodies that agonize the activity of a CB peptide can be generated. In particular, such antibodies can inhibit binding of an intracellular protein that contains a CB consensus sequence according to the invention to an SH3 domain. Such antibodies can be tested using the assays described infra for identifying ligands.

CB Molecules—CB Peptide Analogs and Conjugates

The present invention further contemplates development of small molecule analogs of the CB consensus sequence, e.g., non-peptidyl molecules that are capable of specifically binding to the c-CrkSH3(1) domain with high affinity. Such molecules can be designed using rational techniques, based on the detailed structural information provided herein, and by application of available computer assisted structure design.

Another approach uses recombinant bacteriophage to produce large libraries of peptides. Using the "phage method" (Scott and Smith, 1990, Science 249:386–390; Cwirla, et al., 1990, Proc. Natl. Acad. Sci., 87:6378–6382; Devlin et al., 1990, Science, 249:404–406), very large libraries can be constructed ($10^6$–$10^8$ chemical entities). A second approach uses primarily chemical methods, of which the Geysen method (Geysen et al., 1986, Molecular Immunology 23:709–715; Geysen et al. 1987, J. Immunologic Method 102:259–274) and the recent method of Fodor et al. (1991, Science 251, 767–773) are examples. Furka et al. (1988, 14th International Congress of Biochemistry, Volume 5, Abstract FR:013; Furka, 1991, Int. J. Peptide Protein Res. 37:487–493), Houghton (U.S. Pat. No. 4,631,21 1, issued December 1986) and Rutter et al. (U.S. Pat. No. 5,010,175, issued Apr. 23, 1991) describe methods to produce a mixture of peptides, which may contain L-amino acids, non-peptidyl bonds, and peptidomimetics.

In another aspect, synthetic libraries (Needels et al., 1993, "Generation and screening of an oligonucleotide encoded synthetic peptide library," Proc. Natl. Acad. Sci. USA 90:10700–4; Lam et al., International Patent Publication No. WO 92/00252, each of which is incorporated herein by reference in its entirety), and the like can be used to screen for analogs of the CB consensus peptide according to the present invention.

Screening can be performed on the basis of specific, high affinity binding to a c-CrkSH3(1) domain, inhibition assays, e.g., using a labelled GST-NSPPPALPPKKR (SEQ ID NO:21) fusion protein, and other binding assays, as described herein.

Preferably, a CB peptide of the invention is associated with a carrier molecule to facilitate or enhance biological activity. Preferred carrier molecules facilitate transport through the cell membrane into the cytoplasm, where a CB peptide can function by binding to an SH3 domain. Alternatively, or in addition, the CB peptide can be associated with a carrier that specifically targets the peptide to a cell in which binding of the CB peptide to an SH3 domain is desired. Such targeting molecules peptides, proteins, antibodies, antibody fragments, lectins, carbohydrates, or steroids. Accordingly, as used herein, the term "targeting molecule" refers to a molecule that can be conjugated to a CB peptide, which molecule binds specifically to a molecule found in vivo, such as a receptor or other recognition molecule or a molecule specific to a cell or cells, etc. Steroids are useful carriers, since they are receptor specific and facilitate transport into the cytoplasm. In a specific embodiment in which the targeting molecule is a peptide, the peptide may contain the well known sequence Arg-Gly-Asp (R-G-D). RGD receptors are found on the surface of cells such as endothelial cells, cancer cells, or ova. Antibodies for use as targeting molecules may be specific for a cell surface antigen. In one embodiment, the antigen is a receptor. For example, an antibody specific for a receptor on a tumor cell can be used. In another embodiment, antibodies specific for leukocyte surface antigens, such as lymphocyte antigens, CD (clusters of differentiation) antigens, and receptors (e.g., T cell antigen receptors) can be conjugated to the peptide. Any antibody known in the art that is specific for a cell antigen can be used as a targeting molecule. In another embodiment, the targeting molecule transferrin may be used. More than one targeting molecule can be used, for example, by using two different molecules to target an peptide to the same in vivo location.

A CB peptide may be conjugated to the targeting molecule covalently, using well known cross-linking techniques, or by expression of a chimeric construct, e.g., a single chain monoclonal antibody or a transferrin construct containing the CB consensus sequence.

In a further aspect, a CB peptide or molecule may be labeled. In one aspect, the CB molecule (including CB peptide) may be directly labeled. In another embodiment, a labeled secondary reagent may be used to detect binding of a CB molecule to another molecule, e.g., a CrkSH3(1)-containing protein. Binding may be detected by formation of a chromophore by an enzyme label. Suitable enzymes include, but are not limited to, alkaline phosphatase and horseradish peroxidase. Other labels for use in the invention include colored latex beads, magnetic beads, fluorescent labels (e.g., fluorescene isothiocyanate (FITC), phycoerythrin (PE), Texas red (TR), rhodamine, free or chelated lanthanide series salts, especially $Eu^{3+}$, to name a few fluorophores), chemiluminescent molecules, radio-isotopes, or magnetic resonance imaging labels. Alternatively, a CB molecule may be biotinylated (or conjugated to another molecule) for detection with labeled avidin or streptavidin (or a secondary molecule specific for the conjugated molecule).

As exemplified herein, a CB molecule (e.g., a chimeric GST-CB peptide) expressed recombinantly can be metabolically labeled. In addition to metabolic (or biosynthetic) labeling with $^{35}S$-methionine, the invention further contemplates labeling with $^{14}C$-amino acids and H-amino acids (with tritium substituted at non-labile positions).

Diagnostic and Therapeutic Compositions and Methods

Protein binding is one means by which cells accomplish signal transduction, and thus control activation, proliferation, and differentiation. Therefore, the level of expression of cellular c-Crk can be very important for the diagnosis and treatment of diseases of disorders, particularly cellular transformations that lead to cancer.

Thus, the labeled CB molecules of the invention can be used to detect expression, and measure the level of expression, of cellular Crk, in selected tissues. For example, the presence or absence of expression of c-Crk in cancer cells obtained in a tissue biopsy can be important in evaluating whether the normal cellular control machinery is operating. Similarly, the presence or absence, and level of expression, of c-Crk in immune cells can provide information about the level of immune activation and regulation.

In another embodiment, the level of c-Crk, and, to some extent, other SH3-containing proteins, can be evaluated by detecting the level of binding of a CB peptide to a protein containing such SH3 domains in the sample being assayed. However, as noted above, the present invention advantageously provides a highly specific molecule for binding to the first SH3 domain of c-Crk, and demonstrates much lower binding affinity for other SH3 domains. Therefore, the CB molecules of the invention are highly preferred for detecting the presence and level of expression of c-Crk.

In a further embodiment, antibodies generated to the CB consensus sequence can be used to evaluate the presence or level of activity of the intracellular proteins or polypeptides that bind to c-CrkSH3(1), e.g., the presence or level of intracellular signal transducing proteins. A particular advantage of the present invention is that antibodies can be prepared that are highly specific for an epitope having the consensus sequence of the invention, and thus will be specific for detecting proteins, such as C3G, that bind the c-CrkSH3 domain with high specificity. Immunoassays can be performed by any of the standard techniques described above. The presence of low levels of proteins containing the CB consensus may be indicative of a disease or disorder characterized by a decrease in cellular metabolic activity, possibly resulting from the low level of CB-containing proteins. Conversely, increased levels of these proteins may be characteristic of cellular activation, e.g., such as accompanies oncogenesis.

In another aspect of the invention, antisense oligonucleotides capable of hybridizing to a mRNA encoding a protein containing a CB consensus sequence can be used to inhibit expression of the protein in a cell, and thus modulate signal transduction activity in a cell. Inhibition of signalling activity can be useful, e.g., to modulate the activity of various cells. For example, if testicular or ovarian cells become transformed, it may be desirable to inhibit signalling mediated by c-Crk and C3G in order to inhibit or reverse the transformation.

In a further aspect of the invention, a non-signal transducing CB molecule, e.g., a protein containing one or more CB consensus sequences, can be introduced into cells, either directly or by gene therapy, to modulate the level of signal transduction mediated by c-Crk.

The present invention may be better understood by reference to the following non-limiting example, which is provided by way of exemplification.

EXAMPLE 1

FOUR PROLINE-RICH SEQUENCE WITH UNIQUE SPECIFICITY TO THE FIRST Src HOMOLOGY 3 DOMAIN OF Crk

The widely expressed cellular Crk protein has the domain structure SH2-SH3-SH3. We have previously demonstrated that the more N-terminal S113 domain of Crk [CrkSH3(N)] specifically binds several cytoplasmic proteins. A cDNA encoding one of these proteins was isolated and found to have two different splice forms. The sequence is virtually identical to C3G, a guanine-nucleotide exchange factor. The center region of the 145–155 kDa protein contains four similar proline-rich sequences which are capable of binding individually to the SH3(N) domains of c-Crk and v-Crk. Comparison of these sequences in C3G to proline-rich sequences in other Crk binding proteins suggests that positively charged amino acids following the prolines play an important role in binding to the CrkSH3(N) domain. The endogenous C3G can be co precipitated with Crk from cell lysates of cells expressing high levels of c-Crk or v-Crk, suggesting high binding affinity and a possible interaction in vivo. Unlike many other SH3-binding proteins which interact with multiple SH3 domains, C3G from cell lysates binds preferentially to the CrkSH3(N) domain. This unique binding specificity supports the idea that C3G plays an important role in Crk signaling pathways.

Materials and Methods

Expression of SH3-containing gst-fusion Proteins. gst-GAPSH3, gst-CskSH3, gst-AblSH3, gst-PLC-g-SH3, gst-SpectrinSH3, gst-Nck, gst-SrcSH3 and all gst-Crk constructs have been described (Feller et al., 1994, EMBO J. 13:2341; Chou, 1993, Ph.D. Thesis, The Rockefeller Univeristy). The Grb2 N- and C-terminal SH3 domains obtained as a generous gift from A. M. Pendergast as described (Pendergast et al, 1993, Cell 75:175). The PI3Kp85-a-SH3 domain was a gift of L. Cantley (Kapeller et al., 1994, J. Biol. Chem. 269:1927). Unlabeled and $^{35}$S-labeled gst-fusion proteins were prepared as described (Feller et al., supra).

Library Screening for CrkSH3 Binding Proteins. $2\times10^5$ plaques of a HeLa expression library (Clontech) were screened with $^{35}$S-labeled gst-CrkSH3SH3 for the first screen. Four positive plaques were identified. Two of them gave a strong signal and the corresponding phages were plaque purified in subsequent screens using unlabeled gst-CrkSH3SH3 as a probe. Bound gst-CrkSH3SH3 was detected with an affinity-purified gst antiserum and $^{125}$I-labeled proteinA (Amersham). The first screen with the $^{35}$S-labeled probe gave a very low background since it did not result in isolation of gst binding phages. The two isolated phages contained inserts of 1.2 kb with an identical restriction pattern. The inserts were excised from the phage with EcoRI, subcloned into pBluescript II SK+/−(Stratagene) and pGEX-1N (AMRAD) or pGEX-3X (Pharmacia) and their identity confirmed by sequencing. One of these clones was used as a probe to obtain a 5.5 kb clone from a lpCEV15-M426 human embryonic fibroblast library (a gift of Toru Miki and Stuart Aaronson; Miki et al., 1989, Gene 83:137), which encoded a 5' truncated C3G cDNA that extended to the polyA tail. The original C3G clone of 1.2 kb was also used to probe a blot of HeLa poly(A)$^+$ selected RNA. The missing region of C3G was cloned by PCR. The clones were sequenced using a commercial sequencing kit (UBI).

C3G gst-fusion. pGEX constructs of the C3G proline-rich sequences were constructed by subcloning into pGEX vectors. The correct reading frame was confirmed by sequencing through the junctions. CB-2, CB-3 and CB-4 were generated from PCR products and sequenced entirely. Proteins generated from these constructs were expressed and purified essentially as described (Smith and Johnson, 1988, Gene 67:31). During all steps of purification protease inhibitors (0.3 mM Aprotinin, 50 mg/ml Antipain-dihydrochloride, 100 mg/ml PMSF, 1 mM Leupeptin and 1 mM PepstatinA) were added.

Antisera. The C3G-antiserum (Knudsen et al., 1986, J. Biol. Chem. 261:10765) was produced in rabbits immunized with gst-C3G-C-2,3,4 (amino acids 410–652, see Table I). Antibody binding to C3G was confirmed by Western blotting and showed a doublet of 145/155 kDa. Gag (3C2) and Crk antibodies have previously been described (Potts et al., 1987, J. Gen. Virol. 68:3177).

SH3 Blot Assay. One mg of gst or equimolar amounts of SH3-fusion proteins were subjected to SDS-PAGE, electroblotted and incubated with 2 mg/ml (70,000 dpm/ml) $^{35}$S-labeled gst-C3G CB region as described (Feller et al., supra). Filters were exposed over night.

Precipitation of C3G and Crk Proteins from Cell Lysates. Crk/3Y1 cells (rat fibroblasts expressing v-Crk; Shou e al. 1992, Nature 358:351), c-Crk/CEF (chick embryo fibroblasts overexpressing c-Crk, Reichman, 1993, Ph.D. Thesis, The Rockefeller University) and HeLa cells were harvested in RIPA buffer (20 mM Tris-HCl pH7.5, 150 mM NaCl, 1% Triton-X100, 0.5% deoxycholate, 0.1% SDS, 1 mM Na$_2$EDTA) with protease inhibitors as described (Feller et al., supra). Particulate material was removed by centrifugation for 30 min at 10,000 g. Cytosolic HeLa proteins (S100) for precipitation of C3G were obtained as described (Feller et al., supra). Protein complexes with gst-fusion proteins were precipitated with glutathione-Sepharose beads (Phannacia). For precipitation with the C3G antibody, 1 mg of total cell lysate of Crk/3Y1 or c-Crk/CEF was precipitated with 10 ml of anti-C3G. Protein complexes were precipitated with proteinG Sepharose beads (Pharmacia). In all precipitation experiments, beads were washed three times with RIPA buffer. Proteins were then separated by SDS-PAGE, electroblotted and probed with the antibodies described in the figure legends.

ELISA. gst-CB-1 to -4 proteins were biotinylated with Sulfosuccinimidyl 6-(biotinamido) hexanoate (Pierce) according to the manufacturers instructions. ELISA plates (Nunc) were coated with 100 ng/well of gst-Grb2, gst-CrkSH3SH3 or gst in 0.1M NaHCO$_3$, pH 9.6, over night at room temperature (Jones et al., 1991, Mol. Cell Biol. 11:2641). Wells were then blocked with 2% BSA. After washing three times with blocking buffer (20 mM Tris-HCl, pH 7.5, 100 mM NaCl, 0.05% Tween-20, 1 mM EDTA, 0.2% BSA and 0.1% Ovalbumin), biotinylated gst-CB fusion proteins were added at the concentrations indicated in FIG. 6. To measure bound gst-CB fusion proteins, wells were incubated with horseradish Peroxidase coupled streptavidin (Gibco). A chromogenic substrate, 2,2'-azinobis(3-ethylbenzothiazoline-6-sulfonic acid) diaminonium salt (ABTS, Pierce) was then added and the OD was measured at 405 nm after 5 and 15 min and the 5 min OD value subtracted from the 15 min OD value to yield DOD$_{405}$. In each experiment, the DOD$_{405}$ at saturation of SH3 domain binding sites was considered 100%. DOD$_{405}$ values for all other points within the same experiment were expressed as a percentage of this 100% value. Binding to gst alone was subtracted at each data point.

Results

Cloning of a Protein that Binds to the CrkSH3 Domain. The N-terminal CrkSH3 domain [CrkSH3(N)] binds specifically to a limited number of proteins from HeLa cell lysates (Feller et al., supra). A HeLa expression library was screened to clone proteins encoding CrkSH3 binding proteins. A phage containing a 1.2 kb insert with an open reading frame was isolated. The protein expressed from the phage showed strong binding to gst-CrkSH3SH3, weak binding to gst-Grb2 and no binding to gst-Nck or gst alone. The sequence of the 1.2 kb phage insert is almost identical to the middle region (amino acids 280–653) of C3G, a CrkSH3 binding protein that was recently published by Tanaka et al. (1994, Proc. Natl. Acad. Sci. USA 91:3443). However, the two sequences differ at nucleotide 861 which changes threonine 287 in the previously reported sequence to a proline in our sequence (FIG. 1A). Since this proline residue was subsequently shown to be involved in the binding to the CrkSH3(N) domain, its presence was further confirmed by sequencing PCR amplified HeLa mRNA's. Probing of HeLa poly(A)$^+$ RNA with the 1.2 kb clone detected a 6.5 kb band (FIG. 1B). In addition, two differentially spliced C3G mRNAs were identified by PCR. The shorter one has a 114 nucleotide deletion between nucleotides 151 and 265 (amino acids 50–88) of the coding sequence. Even though this difference was not detectable in Northern blots, multiple bands between 145 and 155 kDa appeared in Western blots that may represent the two splice variants. The C-terminal domain of C3G is homologous to the catalytic domain of the guanine-nucleotide exchange factor CDC25 (Jones et al., 1991, Mol. Cell Biol. 11:2641).

The amino acid sequence of the phage insert contains four stretches of proline-rich sequences (FIGS. 1A and C). They were subsequently shown to bind the CrkSH3 domain and were therefore named Crk Binding sequence 1 to 4 (CB-1 to -4). Alignment of the sequences showed remarkable similarity spanning nine amino acids (FIG. 1C). CB-2 and CB-4 have 8/9 amino acids identical with CB-1, whereas CB-3 has 6/9 identical amino acids with CB-1. CB-1 to -4 are good candidates for SH3 domain binding sequences since they contain a Pro-X-X-Pro motif. One additional proline-rich sequence is localized N-terminal to the first CB motif (amino acids 267 –276). It differs significantly from the other four CB sequences and from sequences in other known Crk binding proteins (Table 1) and was not analyzed in detail.

TABLE 1

Sequence alignment of known or potential (*) CrkSH3(N) binding sequences in Crk binding proteins

| Protein | CrkSH3 binding sequence | SEQ ID NO: |
| --- | --- | --- |
| C3G/CB-1 | SPPPALPPKKRQ | 4 |
| C3G/CB-2 | DTPPALPEKKRR | 5 |
| C3G/CB-3 | EKPPPLPEKKNK | 6 |
| C3G/CB-4 | APPPALPPKQRQ | 7 |
| Abl CB-1 | LQAPELPTKTRT | 10 |
| Abl/CB-2 | AVSPLLPRKERG | 11 |
| Arg/CB-1* | PRLPILPSKTET | 12 |
| Arg/CB-2* | SGSPALPRKQRD | 13 |
| mSos1/P-1 | PVPPPVPPRREP | 14 |
| mSos2/P-1* | LIPPPLPPRKKF | 15 |
| Consensus | XXPPXLPXKXRX | 16 |

Figure 2A:
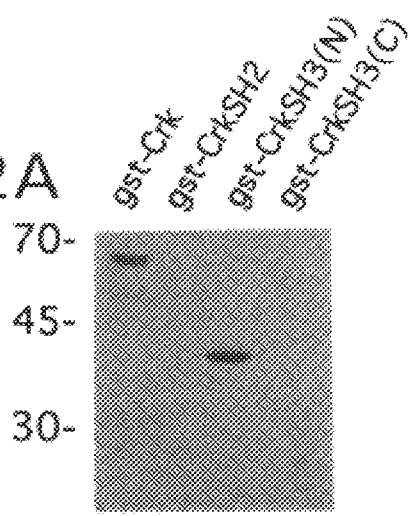
FIG. 2: Specific binding of C3G to the CrkSH3(N) domain. A. Full length Crk and the isolated SH2 and SH3 domains were tested for binding to the C3G CB-region. 1 mg gst or equimolar amounts of gst-fusion proteins as indicated were separated by SDS-PAGE (11%), blotted and probed for binding to $^{35}$S-gst-C3G CB-region. B. Analysis of a panel of SH3 domains for binding to C3G CB-region. Experimental procedures as in A.
Figure 2B:
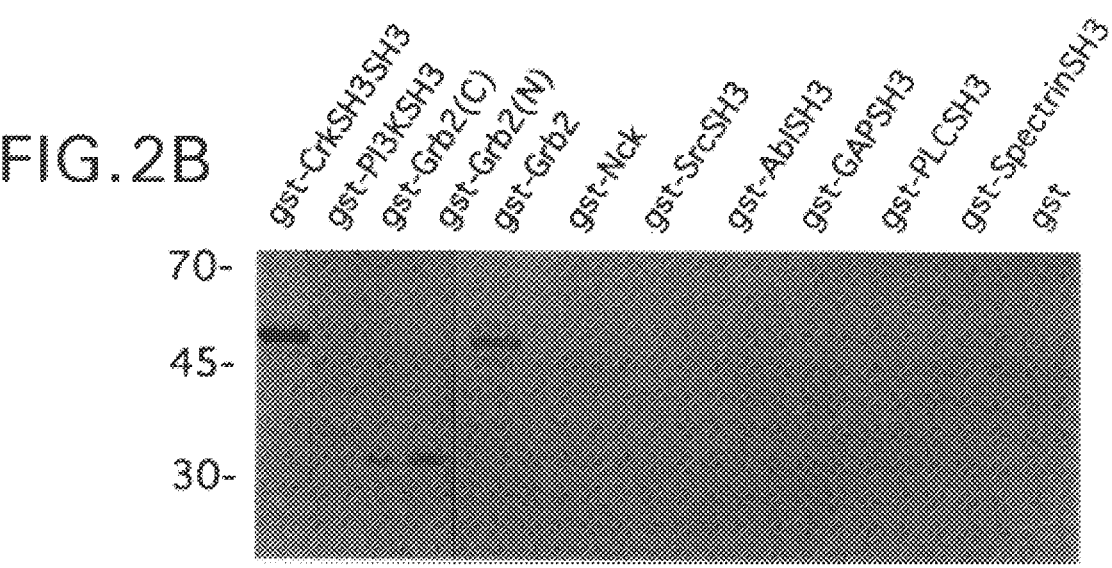
Figure 3:
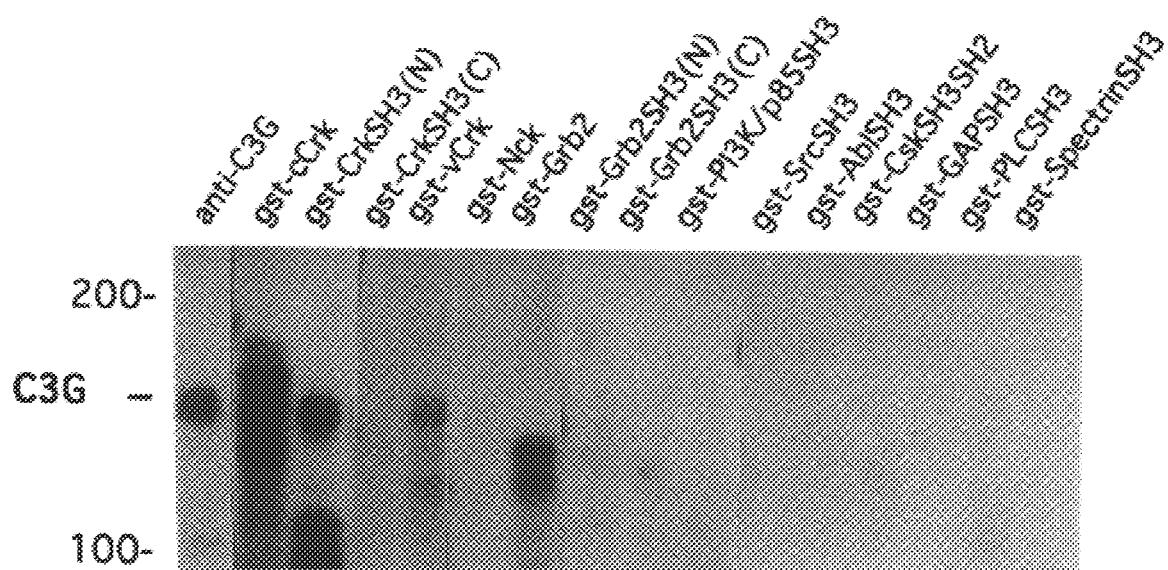
FIG. 3: Specific binding of C3G from cell lysates to Crk proteins containing the CrkSH3(N) domain. One mg of cytosolic proteins from HeLa cells (S100 fraction) was precipitated with 10 ml C3g antiserum (lane 1) or with SH3 domains expressed as gst-fusion proteins (lanes 2–15). 20 mg of gst c-Crk or equimolar amounts of other gst-fusion proteins were used for precipitation. The precipitated proteins were washed with RIPA buffer, subjected to SDS-PAGE (7%), blotted and probed with an antiserum to C3G. In a control experiment the C3G antiserum was preincubated with the immunogen. The bands at 145/155 kDa were specifically competed while the other bands remained visible (not shown).
Figure 6:
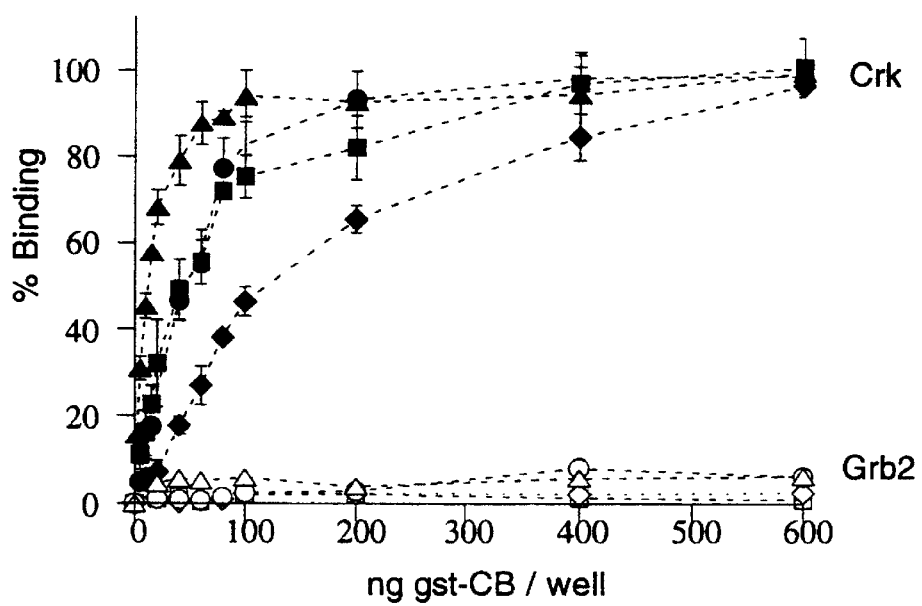
FIG. 6: ELISA of CB-1 to CB-4 binding to the Crk and Grb2. Wells were coated with 100 ng/well gst-CrkSH3SH3 or gst-Grb2. Biotinylated gst-CB-1 (squares), gst-CB-2 (diamonds), gst-CB-3 (circles), gst-CB-4 (triangles) were added at concentrations indicated. Binding of biotinylated gst-CB proteins was detected by a colorimetric assay as described under Material and Methods. Each data point reflects the mean of three independent experiments. The standard error of the mean was usually less than 10%.

C3G Preferentially Binds to the CrkSH3(N) Domain. Since the library screen involved a gst-fusion protein that contained both c-Crk SH3 domains, the domain in Crk sufficient for the binding to C3G was not yet clearly identified. The C3G CB-region containing all four CB-sequences was expressed as an $^{35}$S-labeled gst-fusion protein and tested for binding to full length c-Crk, the CrkSH2 domain and the individual Crk SH3 domains which were immobilized on a filter (FIG. 2A). The C3G CB-region bound only to the isolated CrkSH3(N) domain and full length c-Crk. To assess whether C3G CB-sequences can also bind to other SH3 domains, the $^{35}$S-labeled C3G CB-fragment was tested against a panel of SH3 domains (FIG. 2B). Only gst-fusion constructs that contained the CrkSH3(N) domain bound strongly to the $^{35}$S-labeled C3G CB-region. Grb2, the individual Grb2SH3 domains and the PI3Kp85-a-SH3 domain only bound weakly. Binding to the Grb2 and PI3Kp85-a SH3 domains was only observed in this filter binding assay but did not occur in precipitations from solution or in the ELISA (FIGS. 3 and 6). This may result from the partial denaturation of the blotted SH3 domains.

Subsequently the binding the C3GCB-region to cellular proteins other than Crk was analyzed. Blotted HeLa proteins, initially precipitated with unlabeled gst-CB-1, were probed with $^{35}$S-labeled gst-CB-1. Apart from a faint signal of about 38 kDa, no additional binding proteins were detected beyond nonspecific binding to gst3. This band was also detected when $^{35}$S-labeled cell lysates were precipitated with gst-CB-1 and could be Crk or the Crk-related protein CRKL. It is not possible to distinguish between Crk and CRKL in this assay, since the proteins have almost identical molecular weights. The unambiguous identification of this CB-1 binding protein awaits further analysis with antisera specific for Crk and CRKL. The specificity of C3G-SH3 domain interactions in solution was further analyzed by incubating proteins of the cytosolic fraction of HeLa cells (S100) with a panel of SH3-gst-fusion proteins. Protein complexes were precipitated with glutathione-beads, washed with RIPA buffer and probed with an antiserum raised against C3G. C3G was detectable as a broad band between 145 and 155 kDa in precipitates with gst-fusion proteins of full length c-Crk, the CrkSH3(N) domain and v-Crk (FIG. 3). All these constructs contain the CrkSH3(N) domain. No binding was observed to any other SH3 domain including Grb2, the individual Grb2 SH3 domains and the PI3Kp85-a-SH3 domain. When the antiserum was preincubated with immunogen in a control experiment the 145/155 kDa band was the only signal that was no longer visualized. The proteins precipitated with Grb2 (FIG. 3) were not competed by the antigen.

These data demonstrate that the unique binding specificity of the C3G-CB region towards the CrkSH3(N) domain is retained in the full length C3G protein.

Figure 4:
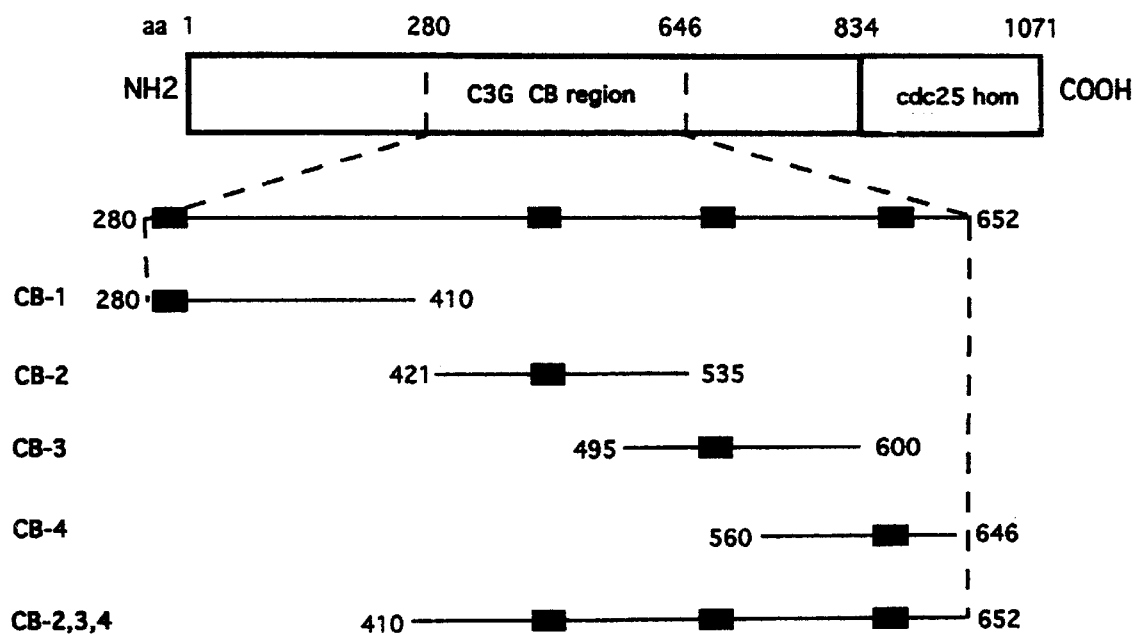
FIG. 4: CrkSH3 binding sites in C3G and C3G fragments that were used for bacterial expression. Schematic diagram of C3G showing the positions of the proline-rich CrkSH3 binding sequences (black boxes) and the constructs used in this study. Numbers indicate the amino acid boundaries of the C3G fragments (see also Table 1).
Figure 5A:
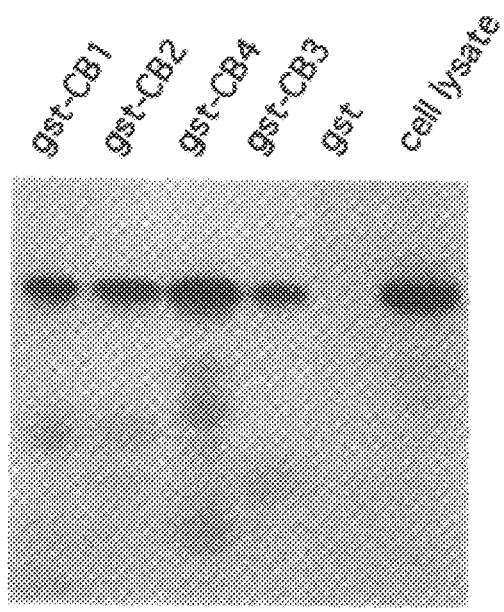
FIG. 5: Binding of individual proline-rich sequences of C3G to v-Crk and c-Crk. A. Total cell lysates (300 mg) of v-Crk/3Y1 cells were incubated with 20 mg of gst-fusion proteins as indicated (see also FIG. 4). Complexes were precipitated with glutathione-beads. The precipitates were washed with RIPA buffer, separated by SDS-PAGE (11%) and blotted. The blot was probed with a monoclonal antibody raised against the Gag portion of the v-Crk protein. B. c-Crk protein was precipitated from total cell lysates (500 mg) of c-Crk/CEFs with gst-fusion proteins as indicated. The precipitated proteins were separated and immobilized as in A and probed with the Crk antiserum.
Figure 5B:
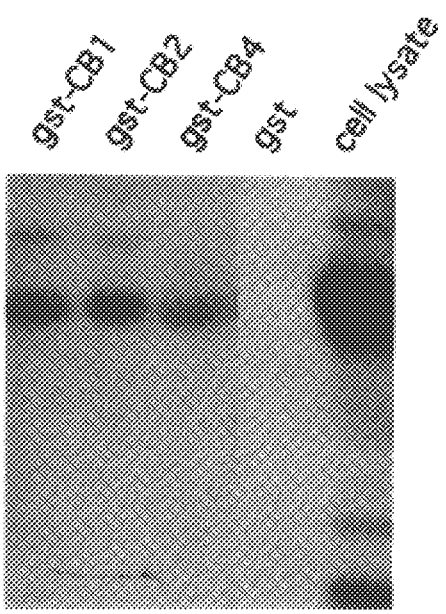

Binding of the Individual Proline-rich C3G-CB Sequences to v-Crk and c-Crk. The four proline-rich motifs in C3G are remarkably similar, but the differences in the amino acid sequences could influence the binding to the CrkSH3 domain. To investigate the binding of each individual proline-rich sequence, gst-fusion proteins containing only a single proline-rich sequence were expressed (FIG. 4). Since the v-CrkSH3 domain slightly differs from the c-CrkSH3 domain in its sequence the binding of both, c-Crk and v-Crk proteins, was tested. Cell lysates of v-Crk expressing rat fibroblasts (v-Crk/3Y1) or c-Crk overexpressing chick embryo fibroblasts (c-Crk/CEF) were incubated with gst-CB-1 to -4 and analyzed by Western blot for the binding to Crk proteins. Both c-Crk and v-Crk bound well to all CB-constructs tested (FIG. 5). The binding was stable in RIPA buffer, suggesting strong binding of each proline-rich CB-sequence to the Crk proteins. These experiments show that there are four potential Crk binding sites in the C3G protein.

Analysis of CrkSH3-C3G Binding by ELISA. To quantify the affinity of the C3G-CrkSH3 interaction we utilized an ELISA. The binding of each proline-rich sequence was analyzed. Gst-CB fusion proteins were biotinylated and probed for binding to immobilized gst-CrkSH3SH3, gst-Grb2 or gst alone. Binding to the CrkSH3SH3 domain was saturable in all cases (FIG. 6). However, Grb2 showed little binding and the binding did not saturate even at the highest concentrations of gst-CB fusion proteins used in these experiments. Binding to gst alone was minimal and was subtracted from the binding to gst-CrkSH3SH3 and gst-Grb2. The high binding affinity between gst-CrkSH3SH3 and the four proline-rich sequences is reflected in apparent $K_d$'s (half saturation points) of 10.4 nM (gst-CB-1), 27 nM (gst-CB-2), 11.3 nM (gst-CB-3) and 2.85 nM (gst-CB-4). The ELISA binding data are consistent with the solution phase binding results shown in FIG. 3 and suggest that the affinity of Grb2 to C3G is not high enough for stable binding.

Figure 7A:
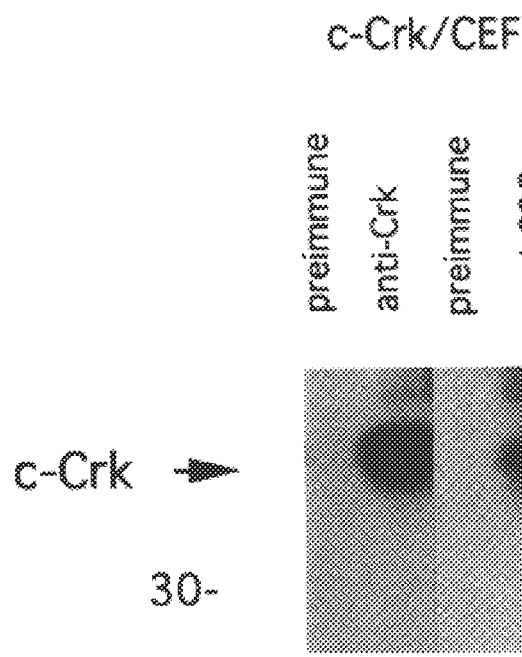
FIG. 7: Coprecipitation of Crk and C3G. A. Total cell lysates of c-Crk/CEFs (1 mg) were precipitated with anti-C3G or control sera as indicated above each lane and blots were probed for c-Crk with a Crk antiserum. B. Total cell lysates of v-Crk/3Y1 (1 mg) were precipitated with anti-C3G or control antibodies as indicated above each lane and probed for v-Crk.
Figure 7B:
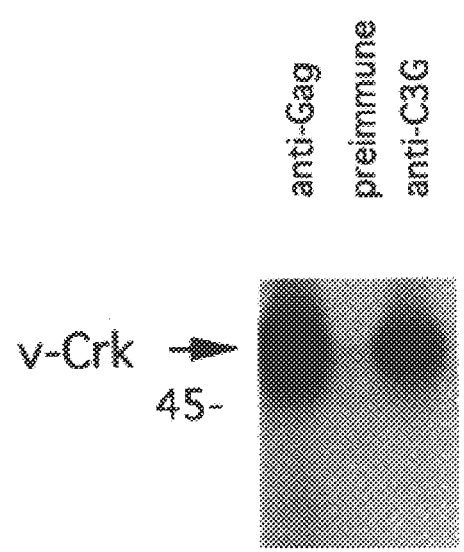

Coprecipitation of Crk and C3G from Cell Lysates. Since the endogenous cellular Crk-II does not form detectable complexes with cytoplasmic proteins in different unstimulated cells (Feller et al., supra), we used cells that overexpress Crk proteins to examine the formation of complexes between C3G and Crk. The endogenous C3G was precipitated with the C3G antiserum from c-Crk/CEF or v-Crk/3Y1 cell lysates and the immune complexes probed for Crk proteins (FIGS. 7A and B). v-Crk is a fusion protein containing viral Gag sequences and was detected with a monoclonal antibody directed against Gag. Crk proteins were only detected in precipitates with the C3G antiserum but not with the preimmune serum. In summary, our data strongly suggest that the interaction between C3G and Crk is highly specific and therefore likely of biological relevance.

Discussion

This example reports cloning a Crk binding protein, C3G, that contains a domain homologous to guanine-nucleotide exchange factors for Ras GTPases and binds with remarkable specificity to the SH3(N) domain of Crk. The stable association between Crk and C3G in cell lysates suggests a biologically important interaction of these two proteins in a yet undefined c-Crk signaling pathway, as well as a possible role for C3G in v-Crk transformation.

Our results differ significantly from the previous report (Tanaka et al, 1994, Proc. Natl. Acad. Sci. USA 91:3443) in the elucidation of C3G sequences that mediate binding to the CrkSH3(N) domain and the binding specificity of C3G for SH3 domains. In our study, four homologous, proline-rich sequences, CB-1 to -4, were identified. Each sequence can bind individually and with similar affinity to the SH3 domains of c-Crk and v-Crk. In contrast, Tanaka et al. found one strong and one weak Crk binding sequence, which correspond to our CB-4 and CB-3 sequences, respectively (FIG. 1C). The reason for the weak binding of the construct corresponding to part of the CB-3 sequence is probably the truncation of this sequence after the first lysine residue following the proline-rich stretch of amino acids. A similar truncation in the CB-1 sequence resulted in a dramatic decrease of the binding affinity. Our data indicate that basic amino acids following the prolines in certain positions strongly increase the affinity of proline-rich sequences to the CrkSH3(N) domain. Alignment of the CrkSH3(N) binding sequences identified in C3G and the Abl kinase with proline-rich sequences of the CrkSH3(N) binding proteins Sos and Arg, also points to the importance of basic amino acids in CrkSH3(N) binding sequences. The consensus sequence for high affinity binding to the CrkSH3(N) domain obtained from this alignment (Table 1) includes two basic amino acids following the prolines and differs therefore significantly from the consensus sequence previously proposed.

Factors that determine the specificity of the various SH3 domains for certain proline-rich sequences are currently not well understood. Only one example of a highly specific SH3 interaction has been previously reported. It occurs between a proline-rich sequence of $p47^{phox}$ and the $p67^{phox}$SH3 domain (Finan et al., 1994, J. Biol. Chem. 269:13752; Sumimoto et al., 1994, Proc. Natl. Acad. Sci. USA 91:5345). Other proline-rich sequences which have been tested often interact with multiple SH3 domains. The results vary to some extent, depending on the experimental system. Interactions of different SH3 domains with short proline-rich peptides or protein fragments have been analyzed in vitro, using purified proteins (Ren et al., 1993, Science 259:1157; Gout et al, 1993, Cell 75:25). However, binding of the corresponding full length proteins is not always detectable in vivo. For example, the GTPase dynamin binds in vitro to the SH3 domain of the p85-a subunit of PI3-Kinase (Gout et al., supra), but no interaction of these proteins was detected when p85-a and dynamin were overexpressed together in cells (Seedorf et al., 1994, J. Miol. Chem. 269:16009). This lack of correlation between in vitro and in vivo binding results has also been observed for the AblSH3 binding proteins 3BP-1 and 3BP-2 and some partial clones obtained by screening of expression libraries with Crk. The binding of the C3G's proline-rich sequences to SH3 domains of Grb2 and PI3Kp85-a which are immobilized on a membrane (FIG. 2B) is likely a similar artifact of the assay system and was not observed in solution phase binding assays. In agreement with the specific, high affinity interaction between Crk and C3G, indicated by the coprecipitation of these proteins from cell lysates, apparent $K_d$'s (half saturation points) in the nanomolar range were obtained for the binding the the CrkSH3SH3 protein in the ELISA, while Grb2 showed very poor, nonsaturable binding. The ELISA dissociation constants are about 1000 fold lower than the values obtained with small proline-rich peptides in solution binding studies (Yu et al., 1994, Cell 76:933). This difference results most likely from the surface adsorption of one of the binding partners. We propose that C3G is not important for intracellular signaling through Grb2.

The consequence of Crk binding to C3G could be the activation of Ras or a Ras-related protein. C3G contains a C-terminal domain with homology to the Ras guanine-nucleotide releasing factor (GRF) CDC25 of S. cervisiae, (Tanaka et al, supra; Shou et al., 1992, Nature 358:351). It belongs therefore into a growing family of mammalian GRFs with CDC25 homology. This family includes currently a brain specific Ras-GRF (CDC25Mn) and the widely expressed Sos proteins (Shou et al., supra; Bowtell et al, 1992, Proc. Natl. Acad. Sci. USA 89:6511). In addition to their catalytic exchange factor domain, $CDC25^{Mm}$ and the Sos proteins contain functionally equivalent, non homologous sequences that control their association with growth factor receptors (Cen et al., 1993, Mol. Cell. biol. 13:7718; Pleiman et al., 1994, Science 263:1609). Sos has four proline-rich stretches of amino acids C-terminal of the catalytic domain which mediate receptor binding via the Grb2 adapter protein, and $CDC25^{Mm}$ has sequences at the N-terminus which are crucial in ligand-induced activation of the exchange factor activity (Cen etl al., supra). While the biological relevance of having two C3G splice variants (FIG. 1A) is currently not understood, divergent N-terminal sequences seem to be common in the family of Ras GRFs. Four different RNAs, which are likely a consequence of differential splicing, were detected for $CDC25^{Mm}$ (Cen et al., supra). They encode a full length protein and three proteins with truncated N-termini. Only the longest protein, can function in a ligand dependent manner. It may therefore be interesting to functionally compare the two forms of C3G.

The specific complex formation between SH3 domains and cellular proteins can have at least three functional consequences. Recent reports indicate that the binding of SH3-containing proteins to enzymes can regulate their catalytic activity. Binding of Grb2 or the SrcSH3 domain to dynamin (Gout et al., supra) as well as the binding of the SrcSH3 domain to PI3Kp85-a (Mayer and Baltimore, 1994, Mol. Cell Biol. 14:2883), increases the enzymatic activities of dynamin and PI3-Kinase. Besides the regulation of enzymatic activities (Gout et al., supra; Cen et al., supra; Mayer and Baltimore, supra), SH3 domains can mediate the substrate recognition of enzymes and the targeting of proteins to specific subcellular locations (Bar-Sagi et al., Cell 74:83).

The best studied SH3 domain-dependent interaction of functionally similar proteins is the binding of the adapter protein Grb2 to the mammalian guanine-nucleotide exchange factor Sos. Upon exposure of cells to some mitogenic stimuli, Grb2 is recruited from the cytoplasm to the membrane where it forms a link between tyrosine kinases and the Ras pathway. Several activated receptor tyrosine kinases generate high affinity binding sites for the Grb2SH2 domain (Olivier et al., 1993, Cell 73:179; Buday and Downward, 1993, Cell 73:611; Gale et al., 1993, Nature 363:88; Baltensperger et al., 1993, Science 260:1950; TObe et al., 1993, J. Biol. Chem. 268:11167). The Grb2 SH3 domains in turn bind to proline-rich sequences at the C-terminus of Sos (Lowenstein et al, 1992, Cell 70:431; Egan et al., 1993, Nature 363:45), thereby bringing Sos in proximity to Ras. The expression of v-Crk or c-Crk-I in PC12 cells potentiates neurite outgrowth. Based on these results, it has been postulated that Crk can activate the Ras pathway (Hempstead et al., 1994, Mol. Cell Biol. 14:1964; Tanaka et al., 1993, Mol. Cell Biol. 113:4409). This activation could result from the binding of Sos and C3G to the CrkSH3(N) domain. While the function of Sos as a Ras exchange factor has been established (Gale et al., supra), the biological activity of C3G in higher eukaryotes is not yet characterized. However, C3G is able to complement a temperature sensitive CDC25 mutant yeast strain (Tanaka et al., 1994, supra), suggesting that C3G acts as an exchange factor for a member of the Ras or Ral family of GTPases. The yeast complementation assay cannot distinguish these activities. A more precise functional analysis of C3G signaling pathways should greatly advance our understanding of the biological functions of c-Crk as well as mechanisms of v-Crk transformation.

EXAMPLE 2

AFFINITY AND SPECIFICITY REQUIREMENTS FOR CrkSH3(1)

The specificity of SH3 domain complex formation plays an important role in determining signal transduction events. The previous example identifies a highly specific interaction between the first CrkSH3 domain [CrkSH3(1)] and proline-rich sequences in the guanine-nucleotide exchange factor C3G. A ten amino acid peptide derived from the first proline-rich sequence ($P^3$-$P^4$-$P^5$-$A^6$-$L^7$-$P^8$-$P^9$-$K^{10}$-$K^{11}$-$R^{12}$) (SEQ ID NO:17) bound with a $K_d$ of 1.89±0.06 μM and fully retained the high affinity and unique selectivity for the CrkSH3(1) domain. Mutational analysis showed that $P^5$, $P^8$, $L^7$ and $K^{10}$ are critical for high affinity binding. A conservative mutation, K10R significantly decreased the affinity to the CrkSH3(1) domain while increasing the affinity to Grb2. Comparative binding studies with the K10R and K10A mutant peptides to c-Crk and v-Crk further suggested that $K^{10}$ binds via a charge dependent and a charge independent interaction to the RT-loop of the CrkSH3(1) domain. Besides determining important structural features necessary for high affinity and specificity binding to the CrkSH3(1) domain, our results also demonstrate that a conservative mutation in a single amino acid can significantly alter the specificity of an SH3 binding peptide.

MATERIALS AND METHODS

Proteins expressed in bacteria. Gst-fusion peptides derived from the C3G CB-1 sequence (amino acids 278–291) were constructed with double stranded oligonucleotides that possessed a 5' BamH-I and a 3' EcoR-I overhang. The oligonucleotides were cloned into BamH-I/EcoR-I cut pGEX-2T. The correct reading frame and sequence of the oligonucleotides was confirmed by sequencing using a UBI sequencing kit. Most gst-SH3 fusion proteins have previously been described in Example 1, supra. All SH3 domain gst-fusion proteins and [35S]-labeled gst-fusion proteins were produced as previously described (Feller et al., 1994, EMBO J. 13:2341). Briefly, gst-fusion proteins were metabolically labeled in bacteria with 1 mCi [35S]-methionine (from a 200 ml culture) in 20 ml methionine-free medium upon induction with 0.1 mM IPTG. Gst-fusion proteins were isolated with Glutathione beads, eluted, and dialyzed against phosphate buffered saline, PBS (10 mM phosphate pH 7.0, 150 mM NaCl), containing 0.05% Tween-20 and 5% glycerol. The specific activity was approximately 35,000 dpm/μg gst-fusion protein.

Peptide synthesis. Peptides were synthesized by automated solid phase methodology utilizing an Applied Biosystems Inc. Model 431A synthesizer programmed with the manufacturer's standard fluorenylinethoxycarbonyl (Fmoc) single coupling protocol. Preloaded resins, Fmoc protected amino acids and other prepackaged reagents were purchased from Applied Biosystems Inc. Cleavage from the resin support and simultaneous side chain deprotection was accomplished with a four-hour treatment with 90% trifluoroacetic acid, 2.5% thioanisole, 2,5% 2-mercaptoethanol, 5% phenol at room temperature. The precipitated, crude peptides were purified to greater than 95% homogeneity using preparative HPLC chromatography. Characterization consisted of analytical HPLC, amino acid analysis and electrospray mass spectrometry. Peptides were resuspended in Tris buffered saline, TBS (10 mM Tris-HCl pH 7.5, 150 mM NaCl), containing 0.05% Tween-20 at 5 mg peptide/ml for all measurements.

Fluorescence Measurements. The fluorescence measurements were based predominantly on the interactions of the peptides with the aromatic residues, predominantly Trp (Yu et al., 1994, Cell 76:933) in the CrkSH3 domain.

Measurements were made with a Perkin-Elmer 760-40 fluorescence spectrophotometer at a excitation wavelength of 290 nm (slitwidth 2 nm) and an emission wavelength of 345 nm (slitwidth 17 nm). A mini-magnetic stirrer, CUV-O-STIR model 333 (HELLMA, Long Island, N.Y.) was used to mix the solution in a 1 cm square quartz fluorescence cell. A circulating water bath was used to maintain the sample temperature at 18° C. To obtain the titration curves for calculations of the binding constants, peptides from a stock solution of 5 mg/ml in TBS, 0.05% Tween-20 were added in small increments to a 1 ml volume of 0.5 μM SH3 domain in PBS, 1 mM Dithiothreitol (DTT). Upon addition of the peptide solutions, maximal changes in fluorescence between 25% and 40% were observed.

Calculation of the binding constant. Since the concentration of the SH3-domain containing protein was low, the experimental data were fitted to the following equation:

$$F=F_{max}*[\text{peptide}]/(K_d+[\text{peptide}]) \tag{1}$$

where [peptide] is the final peptide concentration at each data point, F the measured protein fluorescence intensity at the particular peptide concentration and $F_{max}$ the observed maximal fluorescence intensity of the protein when saturated with the peptide. Non-linear regression curve fitting using SigmaPlot (Jandel Scientific, San Rafael, Calif.) was carried out to fit the experimental data to equation (1) with $F_{max}$ and $K_d$ as fitted parameters. The change in protein concentration as a result of addition of the peptide was properly corrected.

SH3 filter binding assay. The SH3 filter binding assay was carried out as described previously (Reichman, 1993, Cell Growth Diff. 3:451). Briefly, about 30 pmoles of each gst-fusion peptide or gst-fusion SH3 domain were blotted and incubated at room temperature over night in a buffer (TBS, 0.05% Tween-20, 1 mM DTT, 2% BSA, 1% ovalbumin) to allow renaturation. The blot with the gst-fusion peptides was probed with 1–2 μg/ml $^{35}$S-labeled gst-fusion CrkSH3(1) domain, whereas the blot that contains the SH3 domains was probed with $^{35}$S-labeled CB-1/gst-4-12 fusion peptide at 1–2 μg/ml. The blots were washed 3 times with TBS, 0.05% Tween-20, 1 mM DTT, 0.2% BSA, 0.1% ovalbumin, and bound probe was visualized by autoradiography.

Peptide competition assay. Competition of peptides for binding to the CrkSH3 domain was carried out in total cell lysates from chicken embryo fibroblast overexpressing c-Crk upon infection with c-Crk virus. One mg of cell lysate in RIPA buffer (TBS, 1% Triton X-100, 0.5% Na-deoxycholate, 0.1% SDS) was diluted (1:1) with a buffer (TBS, 0.05% Tween-20) containing 2 mM DTT, 2% BSA, 1% ovalbumin, protease inhibitors (20 μg/ml aprotinin, 10 mM PMSF, 10 μM leupeptin, 10 μM antipain, 10 μM pepstatin). One μM CB-1/gst-1-12 was added to each tube and competing peptides were added at a concentration of 500 μM. CB-1/gst-1-12 peptide was precipitated with glutathione-beads, washed 4 times with RIPA buffer and subjected to SDS-PAGE. After blotting c-Crk bound to the CB-1/gst-1-12 fusion peptide was detected with the Crk antiserum (Mayer and Hanafusa, 1990, Proc. Natl. Acad. Scie. USA 87:2638). To quantitate the amount of c-Crk bound to CB-1/gst-1-12, each lane was scanned with a gel scanner. The inhibition of c-Crk CB-1/gst-1-12 binding by the competing peptide was then calculated as follows:

% binding=100% -[peak(competitor peptide)×100]/peak(no peptide)

Results

Analysis of the proline-rich CrkSH3(1) binding (CB) sequences in C3G. We have previously identified four similar proline-rich sequences in the guanine-nucleotide exchange factor C3G, that can bind individually to the CrkSH3(1) domain. Furthermore full length C3G coprecipitates with c-Crk II and v-Crk from cell lysates, suggesting that at least one of these proline-rich sequences binds with high affinity. In addition, when testing a broad panel of SH3 domains, only the first CrkSH3 domain bound to C3G in cell lysates, thus pointing to a remarkable specificity of this interaction. These results suggested that further analysis of the proline-rich sequences derived from C3G should provide better insight into affinity and specificity requirements of the first CrkSH3 domain.

Sequence alignment of Crk binding (CB) sequences from C3G, c-Abl and SOS led to a preliminary consensus sequence for CrkSH3(1) binding spalming about 10 amino acids. A sequence of 10 amino acids that corresponded to the first CB region on C3G (CB-1 peptide), and contained the CB consensus was therefore expressed as a gst-fusion peptide and shown to precipitate C3G from cell lysates (data not shown) indicating that a 10 amino acid sequence is sufficient for high affinity binding. In order to measure the binding affinity more precisely, 10 amino acid peptides identical to the four CB sequences within C3G (CB-1 to CB-4) were compared for binding to the first CrkSH3 domain by fluorescence measurements and inhibition studies in cell lysates (FIG. 8A). The four peptides bound with different affinities with $K_d$'s between 1.89 μM and 35.8 μM. These peptides were also effective in inhibiting the binding of a 12 amino acid gst-fusion peptide (gst-1-12, amino acids 278 to 291 in C3G) to c-Crk II in cell lysates (FIG. 1A). The degree of inhibition correlated with the $K_d$ obtained by the fluorescence measurements. The peptide derived from the first Crk-binding site within the C3G protein (CB-1 peptide) bound with the highest affinity to the CrkSH3(1) domain ($K_d$=1.89±0.06 μM).

Determination of essential elements for high affinity and specificity binding to the CrkSH3(1) domnain. Since the CB-1 sequence bound with highest affinity it was used for further analysis. To determine the minimal sequence that bound with high affinity to the CrkSH3(1) domain, we used a filter binding assay (Feller et al., 1994, EMBO J., 13:2341). A series of truncated gst-fusion peptides were Western blotted and probed for binding to $^{35}$S-gst-CrkSH3 (1) (FIG. 8B). There was no difference in the amount of bound $^{35}$S-gst-CrkSH3(1) to the 12 amino acid, 10 amino acid, and 9 amino acid gst-fusion peptides as long as they contained the Arg residue at the C-terminus. Deletion of the Arg or further truncation from the N-terminius diminished the binding to the $^{35}$S-CrkSH3(1) probe. In addition, mutations of either of the two proline residues from the Pro-x-x-Pro motif, the highly conserved Lys, or the C-terminal Arg residue greatly reduced the binding of the mutated peptides to the CrkSH3(1) domain, demonstrating that these positions are crucial in the interaction.

Since a great preference of full length C3G for the CrkSH3(1) domain was previously observed, binding of an $^{35}$S-labeled 9 amino acid gst-fusion peptide (gst-4-12) to a panel of SH3 domains was tested. In a filter binding assay, the 9 amino acid gst-fusion peptide only bound strongly to the first CrkSH3 domain (FIG. 9). While a weak interaction was detectable with the SH3 domains of Grb2, p85α/PI3-Kinase, Fyn and α-Spectrin in the filter binding assay, as shown in Example 1, these SH3 domains do not form stable complexes with C3G from cell lysates. In summary, these experiments are consistent with a remarkable specificity of C3G for the CrkSH3(1) domain and further demonstrate that the specificity is maintained in a 9 amino acid sequence derived from CB-1.

Alanine scan through the 10 amino acid high affinity binding peptide. To comprehensively analyze the importance of each position within the CB-1 peptide with regards to the binding to the CrkSH3(1) domain, an alanine scan was performed (FIG. 10). Each mutant synthetic peptide was tested for its ability to inhibit the binding of the wild type gst-1-12 peptide to c-Crk in cell lysates. As expected, mutations in either Pro of the Pro-x-x-Pro motif greatly reduced the ability of the mutant peptides to compete for the binding of the wild type gst-1-12 peptide to the c-Crk protein. In addition, a dramatic decrease in the binding affinity was observed when the Leu-7 (the amino acid numbering in the peptides corresponds to the numbers shown in FIG. 8B in italics for the gst-1-12 peptide) was mutated. Weak but significant reductions in affinity were also observed with mutations in the conserved Lys-10 and Arg-12 residues. The Lys-10Ala mutant showed a considerable loss of binding affinity, but less than expected from the Lys-10Leu mutation in the gst-fusion peptide (FIG. 8B) where a great reduction in the binding was obtained. The $K_d$'s for both mutant peptides were therefore measured fluorometrically. While the $K_d$ was increased 11.7 fold with the Lys-10Ala, the $K_d$ increased 200 fold with the Lys-10Leu mutant (Table 3) which is consistent with the results obtained from the peptide inhibition study.

Effects of other domains on CrkSH3(1) binding. To rule out the possibility that sequences outside the CrkSH3(1) domain have a significant impact on the CrkSH3(1)-peptide interactions, the affinities of several murine constructs, all containing the CrkSH3(1) domain to the CB-1 derived peptide were compared. The presence of the CrkSH2 or the second CrkSH3 domain had little effect on the affinity of the CrkSH3(1) to the CB-1 peptide, nor did the gst-tag significantly influence the affinity of the isolated CrkSH3(1) domain, or full length murine Crk to the CB-1 peptide (data not shown). The isolated CrkSH3(1) domain fused to gst was therefore used in subsequent binding studies.

A single amino acid influences the binding specificity of a peptide to the Crk and Grb2 SH3 domains. Despite the large number of published SH3 domain NMR and crystal structures, essential features of physiologically important, highly specific SH3 ligands are still poorly understood. Interaction of a Pro-x-x-Pro motif with the hydrophobic SH3 domain surface occurs in the majority of the SH3 domains currently analyzed and cannot by itself account for the binding specificity. Consequently, amino acids outside the Pro-x-x-Pro motif likely control specificity by their unique interactions. Comparison of binding sequences from C3G which uniquely bind the CrkSH3(1) domain with sequences from the more promiscuous SOS protein which binds to the SH3 domains of Grb2 (Olivier et al., 1993, Cell 73:179), Crk, Nck, and Src, pointed to several potentially important differences in the binding peptides. Although all C3G and SOS sequences in Table 2 contain a Pro-x-ψ-Pro-Pro-β (ψ=hydrophobic, β=basic) motif, the binding affinities vary (Table 2). The only non-conservative difference between the CB-1 wt peptide and the SOS-1 peptide, an Ala-3 (CB-1/wt) to Pro (SOS-1) change, did not effect the binding specificity as demonstrated by the affinities of C3Gmut(1) peptide to the Crk and Grb2 SH3 domains (Table 2), suggesting that another position controls the binding specificity.

Next, the conservative changes between the CB-1 and SOS peptides were analyzed. Alignment of the four proline-rich SOS-1 sequences pointed to a conserved Arg (Table 1). Consequently, fluorometric affinity measurements showed that these SOS sequences bound better to Grb2 than to the CrkSH3(1) domain (Table 2). We therefore instituted a Lys-10Arg mutation in the CB-1 sequence to generate C3Gmut(2). Surprisingly, this conservative mutation increased the $K_d$ to the CrkSH3 about 9-fold, whereas the $K_d$ for Grb2 decreased from 142±3 μM to 23.5±0.8 μM. These data suggest that the Lys-10 residue of the CB-1 sequence plays a crucial role in controlling the binding specificity of the CB-1 peptide to the CrkSH3(1) domain.

TABLE 2

Basic amino acids of a proline-rich motif determine the binding specificity to the first Crk and to the Grb2 SH3 domains

| Origin | Peptide Sequence | SEQ ID NO: | c-CrkSH3(1) $K_d$ (μM) | Grb2SHD $K_d$ (μM) |
|---|---|---|---|---|
| DB-1/wt | PPPALPPKKR | 17 | 1.89 ± 0.06 | 142 ± 3 |
| SOS-1 | PPPVPPRRRR | 38 | 5.24 ± 0.16 | 3.54 ± 0.16 |
| SOS-2 | PPAIPPRQPT | 39 | 127 ± 5 | 42 ± 4 |
| SOS-3 | PPLLPPREPV | 40 | 206 ± 9 | 88 ± 3 |
| SOS-4 | GPPVPPRQST | 41 | 663 ± 3 | 94 ± 5 |
| C3Gmut(1) | PPPPLPPKKR | 31 | 1.45 ± 0.03 | 203 ± 3 |
| C3Gmut(2) | PPPALPPRKR | 42 | 17.2 ± 0.4 | 23.5 ± 0.8 |

The affinity of each peptide to gst-CrkSH3(1) or gst-Grb2 was determined by fluorescence measurements as described in Materials and Methods. The bolded Lys or Arg residues correspond to the highly conserved basic residues in the Crk or Grb2 binding sequences. Mutants are derived from the CB-1/wt sequence and the mutated positions are underlined. The first SH3 domains of Crk and Grb2 are expressed as gst-fusion proteins.

Interaction of acidic residues in the CrkSH3 domains with basic peptide residues. The interaction of the Lys-10 in the CB-1 sequence with the CrkSH3(1) domain was further investigated. The NMR structure of p85αSH3 with a high affinity binding peptide suggested that basic peptide residues interact with acidic residues on the loops of the SH3 domain (Yu eet al., 1994, Cell 76:933). The RT-loops of the Crk/CRKL SH3(1) domains contian a three (v-Crk, CRKL) or four (c-Crk) amino acid acidic cluster whereas the n-Src loop contains two adjacent Glu residues in all cases. In the RT-loop the two Asp residues, Asp-148 and Asp-151 in chicken c-Crk are conserved amongst the aligned Crk/CRKL SH3 domains. The second position shows a conservative change between chicken and mouse and an Ala in CRKL without a significant loss in affinity to the CB-1 peptide. In v-Crk, the third acidic residue is mutated from Glu to Gly. This mutation reduces the affinity of the v-Crk SH3 domain to the CB-1 peptide by about 14-fold suggesting that the Glu-150 in chicken c-Crk and the corresponding amino acids in mouse c-Crk and CRKL are involved in the binding to basic peptide residues.

The complexity of interaction of this acidic cluster on the RT-loop with basic peptide residues became apparent in binding studies with milutant peptides (Table 3). The Lys-10 residue was mutated to Arg, Ala or Leu and the affinity of these mutant peptides to c-CrkSH3(1), v-Crk and CRKL was determined. A Lys-10Ala mutation eliminates the positive charge and reduced the binding affinity 11.6-fold for c-CrkSH3(1) and 9.7-fold for v-Crk. In contrast, a conservative mutation from Lys-10 to Arg only decreased the binding of the mutant peptide to c-Crk but not to v-Crk. Binding to CRKL of this mutant peptide was 4-fold reduced. The SOS-1 peptide resembles the mutant peptide since it also contains an Arg at the position corresponding to Lys-10. Accordingly, binding of the SOS-1 peptide to v-Crk and CRKL occurred with affinities similar to the CB-1/Lys-10Arg mutant (C3G mut(2), Table 3). However the SOS-1 peptide bound to c-CrkSH3(1) with a $K_d$ of 5.24±0.16 μM which is a lower $K_d$ than expected from the binding affinity of the Lys-10Arg mutant, suggesting that the loss of affinity caused by the Arg is compensated by the binding of other peptide residues.

TABLE 3

Point mutations in the v-Crk and CRKL SH3 domains effect the binding to basic peptide residues

| Peptide | SEQ ID NO: | gst-c-CrkSH3(1) $K_d$ (μM) | gst-v-Crk $K_d$ (μM) | gst-CRKL $K_d$ (μM) |
|---|---|---|---|---|
| PPPALPPKKR | 17 | 1.89 ± 0.06 | 25.5 ± 0.2 | 2.79 ± 0.1 |
| PPPALPPRKR | 42 | 17.2 ± 0.4 | 23.5 ± 0.8 | 11.2 ± 0.5 |
| PPPALPPAKR | 35 | 22.1 ± 0.5 | 248 ± 10 | |
| PPPALPPLKR | 25 | 379 ± 1 | 437 ± 6 | |
| PPPALPPKAR | 43 | 5.74 ± 0.14 | | |
| PPPALPPKKA | 37 | 9.3 ± 0.2 | 71.8 ± 1.1 | |
| PPPALPPKKK | 44 | 5.0 ± 0.3 | 36.2 ± 0.8 | |
| PPPVPPRRRR | 38 | 5.24 ± 0.16 | 23.7 ± 0.6 | 10.5 ± 0.8 |

Lys-11 in the CB-1 peptide is poorly conserved amongst all CrkSH3(1) binding sequences. Accordingly, a mutation to Ala did not significantly reduce the binding affinity.(Table 3 and FIG. 10). The role of the conserved Arg residue at the end C-terminus of the peptide remains poorly understood. An Arg is present in all the high affinity Crk binding sequences derived from various proteins, but mutations of this residue did not greatly effect the affinities of the mutated peptides (Table 3 and FIG. 3). However, a deletion of the Arg-12 in the gst-fusion peptide abolished the binding almost entirely (FIG. 8). Our results from binding studies with gst-fusion peptides are consistent with the $K_d$ measurements obtained with synthetic peptides and point to important features in Crk-binding sequences that are necessary for a specific, high affinity interaction with the CrkSH3(1) domain.

DISCUSSION

As noted in Example 1, The interaction between the guanine-nucleotide exchange factor C3G and the Crk proteins likely plays an important role in signalling pathways that involve the c-Crk and v-Crk proteins (see also, Tanaka et al., 1994, Proc. Natl. Acad. Sci. USA 91:3443). In addition to the high affinity of the four proline-rich sequences in C3G for the CrkSH3(1) domain, a unique specificity of these sequences for the CrkSH3(1) domain was noticed. This highly specific interaction was therefore analyzed into more detail to determine its underlying structural features. A peptide derived from the first Crk-binding sequence within C3G (CB-1 peptide) bound with the highest affinity (1.89 $\mu$M) to the first c-Crk SH3 domain [CrkSH3(1)] (FIG. 8A). The affinity to the CrkSH3(1) domain remained unchanged upon truncation of the binding sequence to a 9 amino acid gst-fusion peptide. Further truncation to an 8 amino acid peptide from the N-terminus (FIG. 8B, gst-5-12) reduced the affinity considerably whereas deletion of the C-terminal Arg-12 (FIG. 8B, gst-3-11) abolished all binding. The loss of affinity with Arg-12 mutants (FIG. 8B, gst-3-12R12N, gst-4-12R12N) also points to the importance of a positively charged amino acid at this position which is highly conserved amongst Crk-binding sequences in proteins. This Arg may contact the CrkSH3(1) domain, may influence the conformation of the binding peptides. In general, the number of amino acids that are necessary for high affinity complex formation with SH3 domains lies between 7 and 9 amino acids (Finan et al., 1994, J. Biol. Chem. 269:13752; Yu et al., 1994, Cell 76:933). Since the design of peptides and structural analogues that inhibit SH3 domain function is one of the goals of this analysis, it is important to demonstrate that the unique specificity of C3G for the CrkSH3(1) domain was retained in the 9 amino acid peptide sequence (FIG. 9). In contrast to the less specific SOS-1-derived peptide which bound with similar affinities to the SH3 domains of Grb2 and Crk, the C3G-derived CB-1 peptide bound 75-fold better to the CrkSH3(1) domain than to Grb2 (Table 3). Consequently, when introduced into cells, the CB-1 peptide should result in a selective inhibition of Crk signalling pathways without significantly interfering with Grb2 signalling.

Alanine scanning through the CB-1 sequence demonstrated the critical role of Leu-7 within the Pro-x-Leu-Pro motif in the binding to the CrkSH3(1) domain (FIG. 10). In addition to the Pro-x-Leu-Pro sequence, a motif that interacts with many SH3 surfaces, the importance of a lysine residue (Lys-10) in controlling the binding specificity and affinity of the CB-1 sequence to the CrkSH3(1) domain is also evident. Most recently two groups (Lim et al., 1994, Nature 372:375; Feng et al., 1994, Science 266:1241) demonstrated that non-proline residues in SH3-binding motifs determine the orientation of these motifs along the SH3 domain surface. Orientation of the SOS-1 peptide N- to C-terminal across the surface of the Grb2(C)SH3 domain, defined as "minus" orientation occurs through interactions of a Val and Arg residue (Lim et al., 1994, supra). By sequence analogy, the four C3G derived sequences should be positioned similar to the SOS-1 peptide in the "minus" orientation through the interaction of their corresponding Leu-7 and Lys-10 residues with the CrkSH3(1) domain which is not consistent with the orientation suggested by Feng et al. (supra) for the C3G derived sequence. In addition to controlling the orientation of the peptide, Lys-10 strongly influences the preference of the CB-1 sequence for the CrkSH3(1) domain. A Lys to Arg mutation at this position decreases the affinity to the CrkSH3(1) domain, but increases the affinity of the peptide to Grb2 (Table 2), while the orientation of the peptide is maintained. This observation demonstrates that a single conservative amino acid change in an SH3 binding sequence can effect binding specificity. The strong preference of the CrkSH3 domain for a Lys at this position is a unique property of the CrkSH3 domain. In contrast, an Arg at this position allows for binding to several SH3-domains as illustrated by the interaction of the SOS-1 peptide with SH3 domains of Grb2, Crk (Table 2), and binding of the SOS protein to the SH3 domains of Grb2 (Olivier et al., 1993, Cell 73:179), Crk, Src and Nck. The difference in the binding spectrum of the CB-1 and SOS-1 peptides demonstrates that high affinity interactions may be of variable specificity.

Structural studies of p85$\alpha$ and Abl SH3 domains with high affinity binding peptides (Yu et al., supra; Musacchio et al., 1994, Nature Structural Biology 1:546) pointed to an interaction of the SH3 ligand with an Asp residue in the RT-loop of the p85$\alpha$SH3 domain or a Thr residue in the RT-loop of the AblSH3 domain, both corresponding to Asp-151 in chicken Crk. A Thr at this position is unique to the AblSH3 domain and explains the preference of the AblSH3 for an interacting proline in the 3BP-1 peptide. However, the Asp residue is conserved amongst most SH3 domains and by itself does not explain specificity of p85$\alpha$ binding peptides for the p85$\alpha$SH3 domain. An Asp is also present at a corresponding position in the SH3 domains of chicken c-Crk (Asp-151), v-Crk (Asp-386) and CRKL (Asp-141). Surprisingly, our binding studies show a 15-fold difference in the binding of the c-Crk and v-Crk SH3 domains to the CB-1 and SOS-1 peptides (Table 3). Therefore, additional acidic residues surrounding the Asp-151 in chicken c-Crk may influence the interaction with basic peptide residues. V-Crk has a Glu to Gly change at position 384 which causes the decrease in binding to the SOS-1 and CB-1 peptides. In agreement with the peptide binding studies, less binding of C3G to gst-v-Crk than to gst-c-Crk in cell lysates has been noticed. Since the Lys-10 in the CB-1 peptide corresponds to the Arg in the SOS peptide that forms a salt bridge with Glu-172 in the RT-loop of the Grb2SH3 domain (Feng et al., 1994, supra), acidic residues in the RT-loop and not the n-Src-loop likely contact Lys-10. This hypothesis has been confirmed upon determination of the crystal structure for the CrkSH3(1) with the CB-1 peptide (Example 3, infra). Interestingly, a Lys-10Arg mutation decreased the binding to the c-CrkSH3(1) domain by 10-fold but had no effect on the binding of the mutant peptide to the v-CrkSH3 domain. In contrast, a Lys-10Ala mutation decreased the binding by 10-fold to both c-Crk and v-Crk, suggesting that the charge of Lys-10 plays an important role in the binding of the CB-1 peptide to the c-Crk and v-Crk SH3 domains. The structural parameters that explain the similar binding affinities of the Lys-10Arg mutant peptide to c-Crk and v-Crk have been elucidated by analyzing the crystal structures of the CrkSH3(1) domain complexed to the CB-1 or SOS-1 peptides and are discussed in detail in Example 3.

The specificity of SH3-domain interactions is believed to be important in controlling the formation of protein-protein complexes that allow the spatially and timely correct propagation of a signal. Our mutational analysis together with the recently obtained crystal structure define molecular parameters that underlie the uniquely specific complex formation between the guanine-nucleotide exchange factor C3G and the Crk proteins. In contrast to C3G, the guanine nucleotide exchange factor SOS binds with high affinity to several SH3 domains. This seemingly low degree of specificity of the SOS protein which has also been observed with other SH3 binding motifs (Liu et al., 1993, Mol. Cell Biol. 13:5225; Gout et al., 1993, Cell 75:25–36) may either be a functionally important parameter of SH3 domain-ligand interactions in the cells or may be an artifact of the in-vivo or in-vitro systems that utilize high concentrations of SH3 domains and binding proteins to demonstrate these interactions. The promiscuity of the binding of proline-rich sequences in SOS to multiple SH3 domains could generate a point of convergence of several receptor pathways to Ras. The biological importance of the unique specificity between Crk and C3G compared to the lesser specificity of the SOS protein provides a unique and valuable tool for specific modulation of Crk-mediated intracellular signal transduction.

EXAMPLE 3

STRUCTUAL BASIS FOR THE SPECIFIC INTERACTION OF LYSINE WITH srkSH3(1)

Proline-rich segments in the guanine nucleotide exchange factor C3G bind much more strongly to the amino-terminal SH3 domain (SH3-N) of the proto-oncogene product Crk than to other SH3 domains. The presence of a lysine instead of an arginine in the C3G peptides appears to be crucial for this specificity towards Crk. To determine the structural role of lysine in this binding specificity, the crystal structure of Crk SH3-N complexed with a high affinity peptide from C3G (PPPALPPKKR, SEQ ID NO: 17, $K_d$~2 μM) has been determined at 1.5 Å resolution. The peptide adopts a polyproline type II helix that binds, as dictated by electrostatic complementarity, in reversed orientation relative to that seen in the earliest structures of SH3-peptide complexes. A lysine in the C3G peptide is tightly coordinated by three acidic residues in the SH3 domain. In contrast, the co-crystal structure of Crk SH3-N and a peptide containing an arginine at the equivalent position (determined at ~1.9 Å resolution) reveals non-optimal geometry for the arginine and increased disorder. From these results, it can be concluded that the Crk SH3 domain engages in an unusual lysine-specific interaction that is rarely seen in protein structures, and which appears to be a key determinant of its unique ability to bind the C3G peptides with high affinity.

Materials and Methods

Expression and purification. The DNA sequence coding for the amino-terminal SH3 domain of c-crk was amplified using polymerase chain reaction (PCR) with a mouse cDNA clone as a template. The amplified fragment encodes 58 residues (134–191) of the mouse c-Crk protein plus an initial methionine. This fragment was cloned into the *E. coli* expression vector pET3a (Novagen). Cultures of *Escherichia coli* BL21(DE3) strains, transformed by the resulting plasmid, were grown at 37° C. in LB medium supplemented with 100 μg/ml ampicillin (Sambrook et al., 1989, Cold Spring Harbor Laboratory Press). After 3 hours of induction with isopropyl-thio-βD-galactoside (IPTG) at 37° C., the cell pellet from 1 liter of culture was resuspended in 100 ml of standard buffer (20 mM Tris, pH 8.0, 2 mM DTT, 0.5 mM EDTA) supplemented with 50 μg/ml leupeptin (Boehringer-Mannheim, Germany) and 1% (v/v) aprotinin (Sigma). Cells were lysed by sonication on ice and the suspension was centrifuged for 20 minutes at 15,000 r.p.m. at 4° C. in a Beckmann JA17 rotor, and the clear supernatant was recovered. Protein purification proceeded along standard lines using a Q-Sepharose Fast Flow column (Pharmacia), a mono-Q HR 10/10 column (Pharmacia) and a Superdex75 HiLoad 16/60 column (Pharmacia). The protein was concentrated to 85 mg/ml using ultrafiltration (Amicon). SDS-PAGE electrophoresis using Coomassie blue staining reveals a single band at the expected molecular weight (7 kDa).

Crystallization with peptides. The two peptides used in this Example, C3G (PPPALPPKKR) and SOS (PPPVPPRRRR) prepared as described supra were made available to use for crystallization. Peptides were synthesized using conventional F-moc technology. The peptides were purified by HPLC and lyophilized prior to resuspension in buffer for crystallization, and their identities were confirmed by mass spectroscopy. Crystallization of the c-Crk SH3-N/peptide complexes was performed using the hanging drop technique at 21° C. The best crystals were obtained by vapor diffusion against a reservoir solution containing 0.1M sodium acetate pH 4.6, 0.2M ammonium acetate, 28–32% polyethyleneglycol (PEG) 4K. One microliter of the c-Crk SH3-N protein solution (85 mg/ml, 12 mM) was first mixed with 1.5 ml of C3G or SOS peptide solution (10 mg/ml, 9.0 mM, in water) and then mixed with 1.0 ml of reservoir solution. Crystals were reproducibly obtained over a period of several days, with final dimensions of 2.0×0.2×0.2 mm³ in the best cases. Interestingly, all attempts at obtaining crystals in the absence of high affinity peptides were unsuccessful.

Crystals of CrkSH3 complexes with either peptide are obtained in the same crystal system (tetragonal $Pp4_1$; a=47.2 Å, c=29.5 Å for the Sos complex). X-ray diffraction data were measured using a Rigaku R-AXIS IIC imaging plate area detector, mounted on a Rigaku RU200 rotating anode X-ray generator. Each data set was collected from a single crystal flash-frozen at −160° C. The crystals were cryoprotected by transferring them to a solution containing 0.1M sodium acetate, pH 4.6, 0.2M ammonium acetate, 35% PEG 4K supplemented with 10% glycerol. Data for CrkSH3/C3G were collected using a crystal to detector distance of 60 mm and exposure times of 10 minutes for 2° oscillations (for data to 1.50 Å spacings) and a total of 80 frames were collected. Data for the SOS complex were collected with a crystal to detector distance of 100 mm (for data to 1.90 Å spacings), exposures of 60 minutes and 30 oscillations. Data processing and reduction were carried out with the HKL, DENZO and SCALEPACK programs. Statistics for the final data sets are given in Table 5.

Structure determination and refinement. The structure of the c-Crk/C3G complex was determined by molecular replacement using the X-PLOR program (Brunger A. T., (1990), Acta Crystallogr. Sect. A., 46:46–57). The crystal structures of two SH3 domains, Lck SH3 (Eck et al., 1993) and Nck amino-terminal SH3 (Wu & Kuriyan, unpublished), were independently used as search models. No model for bound peptide was included in the molecular replacement calculations. Rotation function searches followed by Patterson correlation refinement (Brunger A. T., (1990), Acta Crystallogr. Sect. A., 46:46–57) gave similar results with either Lck or Nck SH3 domains as the model. The highest peak in the rotation search corresponded to an orientation of the model that gave a strong signal in translation functions calculated using $P4_1$ (but not $P4_3$) as the space group. Consistent results were obtained using various resolution ranges. The peak in the translation function was 10σ above the mean value when using data from 8.0–2.5 Å, and the next highest peak was below 5σ. This solution was used for further structural refinement.

The structure was refined following standard procedures using X-PLOR (Brunger et al., 1990, Acta Crystallogr., A46:585–593) and "O" (Jones et al., 1991, Acta Crystallogr., A47:110–119). Charges for the sidechain atoms of Lys, Arg, Glu and Asp were set to zero, and thus the refinement procedure is not expected to introduce any bias towards ion-pairing interactions. Rigid body refinement in X-PLOR of the translation function solution reduced the R-value from 50.2% to 49.7% (all data with $|F|>2\sigma$, 8.0–2.5 Å). This model was then subjected to 200 cycles of conjugate gradient optimization, which reduced the R-value to 29.7% (8.0–2.5 Å). Electron density maps calculated at this stage were interpretable in terms of the sequence of c-Crk SH3-N, and strong density corresponding to the bound peptide was visible. In particular, very strong density was observed for the sidechain of Lys 8 in the peptide, as well as for Leu 5 and Pro 2. The unambiguous placement of the lysine and leucine sidechains made it obvious that the peptide orientation was reversed relative to that seen previously in the p85, Abl and Fyn SH3 domains (Lim & Richards, 1994, Nature Struct. Biol. 1:221–225, Yu et al., 1994, Cell, 76:933–945), and a model for peptide residues 1 to 8 was built into density. The atomic model for Lck SH3 (Eck et al., 1994, Nature, 368:764–769) was modified to correspond to the sequence of c-Crk SH3-N, and rebuilt based on the electron density map. Several cycles of model building and crystallographic refinement, including simulated annealing, resulted in a final model that has an R value of 17.4% (for data between 6.0 and 1.5 A resolution) with very good stereochemistry (see Table 5). The model contains 57 residues of c-Crk SH3-N (residues 134 to 190), 9 residues of the peptide (no electron density is seen for the terminal arginine), and 119 water molecules.

The refined structure of the c-Crk SH3-N domain (with peptide removed) was used to initiate refinement against data for the SH3-N/Sos complex, since the two crystal forms are isomorphous. During the initial rigid-body refinement, the R-value dropped significantly from 51.8% to 33.6%, using data from 6.0 to 1.90 Å spacings. Positional refinement reduced the R-value further, to 26.8%. An $(|i,<d|-|Fc|)$ electron density map, with model phases, revealed the presence of bound peptide. In contrast to the C3G complex, where the density for the sidechain of Lys 8 was the strongest feature in the electron density map, the arginine sidechain in the Sos peptide does not have particularly strong density. Nevertheless, the placement of the peptide residues was unambiguous. Straightforward model building and refinement yielded the final model which contains 37 residues of c-Crk SH3-N (residues 134 to residue 190), 8 residues of SOS (residue 1 to residue 8; no electron density is present for the last two arginine residues) and 68 water molecules. The Arg 8 sidechain of Sos is not visible in electron density maps, and so an alanine residue was built at that position. The final R-value is 18.3% (using data from 6.0 to 1.9 Å, see Table 5).

Results and Discussion

The structure of c-Crk SH3-N complexed with the C3G and Sos peptides. Crystals of the two peptides bound to Crk diffract to very high resolution, and the data sets used have been limited to 1.5 Å and 1.9 Å for the C3G and Sos complexes, respectively, mainly due to experimental constraints such as the time available for data collection. FIG. 11 shows electron density at 1.5 Å resolution for the C3G peptide bound to the Crk SH3 domain. Strong density is seen for the first 8 residues of the peptide (PPPALPPK) and somewhat weaker density for the lysine at position 9. The C-terminal arginine is disordered and not visible in the electron density. The peptide adopts a left-handed polyproline type II helix over most of Its length (Table 4), and is bound with the C-terminal residues near the RT and n-Src loops (FIG. 11). A striking aspect of the electron density is that the strongest density features associated with the peptide is for the lysine sidechain at position 8. The electron density is stronger for the terminal atoms of the side chain than for the backbone, indicating unusually tight interactions between the lysine and the SH3 domain.

TABLE 4

Backbone torsion angles and structural deviations in the C3G and Sos Peptides

| Position | Peptide | Res. | Φ | Ψ | Deviation from ideal PPII helix (Å) | Deviation between C3G and Sos (Å) |
|---|---|---|---|---|---|---|
| $P_4$ | C3G | Pro | ND | 161.1 | 4.74 | |
| $P_3$ | C3G | Pro | −62.9 | 168.9 | 2.49 | 0.59 |
|  | Sos | Pro | ND | 166.8 | 1.56 | |
| $P_2$ | C3G | Pro | −78.8 | 175.6 | 0.35 | 0.35 |
|  | Sos | Pro | −71.2 | 164.6 | 0.38 | |
| $P_1$ | C3G | Ala | −60.4 | 138.8 | 0.24 | 0.61 |
|  | Sos | Pro | −64.4 | 137.7 | 0.37 | |
| $P_0$ | C3G | Leu | 81.9 | 124.2 | 0.27 | 0.48 |
|  | Sos | Val | −81.3 | 121.0 | 0.35 | |
| $P_{-1}$ | C3G | Pro | −68.4 | 152.7 | 0.26 | 0.42 |
|  | Sos | Pro | −61.9 | 150.0 | 0.29 | |
| $P_{-2}$ | C3G | Pro | −70.8 | 151.9 | 0.07 | 0.35 |
|  | Sos | Pro | −68.9 | 160.6 | 0.09 | |
| $P_{-3}$ | C3G | Lys | −91.5 | 143.0 | 0.67 | 0.28 |
|  | Sos | Arg | −97.5 | 160.3 | 0.43 | |
| $P_{-4}$ | C3G | Lys | −118.4 | ND | 0.40 | 0.41 |
|  | Sos | Arg |  | ND | 0.40 | |

Notes for Table 4.
The angles for an ideal polyproline helix are −78o and +149o, respectively (Ramachandran & Sasisekharan, 1968, Adv. Protein Chem., 23: 283–437).
An ideal polyproline type II (PPII helix was generated and aligned with the central residues ($P_1$ to $P_{-2}$) of the C3G and Sos helices, respectively.
The deviations in $C^\alpha$ positions between the ideal and actual helices are shown.
The last column shows the deviations in $C^\alpha$ positions between the C3G and Sos peptides after the protein structure are superimposed by least-squares.

The overall fold of the Crk SH3-N domain is very similar to that of other SH3 domains. In particular, comparison with the crystal structures of the SH3 domains of spectrin (Musacchio et al., 1992, Nature, 359:851–855), Fyn (Noble et al., 1993, EMBO J., 12:2617–2624), Lck (Eck et al., 1994, Nature, 368:764–769), Abl (Musacchio et al., 1994, Nature Struct. Biol., 1:546–551) and Nck, results in rms deviations in $C^\alpha$ positions between the Crk and other SH3 domains of approximately 0.5 to 0.6 Å for the secondary structural elements (deviations are larger for the structures determined by NMR). The only regions with significant structural difference are the loops connecting the β strands, in particular the so-called RT and n-Src loop that are involved in peptide recognition (FIG. 12).

FIG. 13 shows a schematic diagram of the C3G peptide as bound to the Crk SH3 domain. For consistency, we adopt the notation used previously (Lim et al., 1994, Nature, 372:375–379), and refer to sites on the polyproline helix as $P_{-1}$, $P_0$, $P_{+1}$, etc., where Leu 5 in the C3G peptide occupies the $P_0$ position (FIG. 13). Using this notation, there are 6 binding sites for the peptide on the Crk SH3 surface, corresponding to $P_{+3}$ (Pro 2 in C3G), $P_{+2}$ (Pro 3), $P_0$ (Leu 5), $P_{-1}$ (Pro 6), $P_{-3}$ (Lys 8) and $P_{-4}$ (Lys 9). The requirement for proline residues at certain positions in the peptide has been explained by considering the disposition of non-proline sidechains with respect to the SH3 surface at various positions along the polyproline type II helix (Feng et al., 1994, Science, 266:1241–1247, Lim et al., 1994, Nature, 372:375–379). The polyproline helix has a triangular cross-section, and sidechains along two of the edges interact with the surface of the SH3 domain. Non-proline sidechains along one edge tend to be in conformations that extended away from the SH3 surface, leading to poorer interactions (referred to as "external packing" (Lim et al., 1994, Nature, 372:375–379)). Proline sidechains at this edge pack well against the SH3 surface. Non-proline sidechains on the other edge of the helix point into the SH3 surface, and can replace proline at these positions (referred to as "internal packing" (Lim et al., 1994, Nature, 372:375–379)). The third edge of the helix points away from the SH3 surface and can be substituted with non-proline residues, although proline may be favored here to increase the proline content of the peptides with consequent stabilization of the helix. The characteristic PXXP motif that is a feature of SH3 target sites is thus seen to be a consequence of the need to preserve proline residues at sites of external packing, and these will be different depending on the orientation of the peptide (Feng et al., 1994, Science, 266:1241–1247, Lim et al., 1994, Nature, 372:375–379). For C3G bound to Crk SH3, sites $P_{+2}$ and $P_{-1}$ correspond external packing and have proline residues. The sites at $P_{+3}$, $P_0$ and $P_{-3}$ correspond internal packing, and are occupied by a proline, a leucine and a lysine, respectively (FIG. 13).

The interactions between the C3G peptide and the SH3 domain are illustrated in FIG. 14. The peptide residues at positions $P_{-1}$, $P_0$, $P_{+1}$ and $P_{+3}$ are closely packed against conserved hydrophobic residues in the SH3 domain (Phe 141, Phe 143, Pro 183, Tyr 186, Trp 169 and Pro 185). There are three prominent ridges formed on the surface of the SH3 domain by the sidechains of these hydrophobic groups (FIG. 14B), and their spacing is such that a snug fit arises between the sidechains presented by the polyproline helix and the SH3 surface (Lim & Richards, 1994, Nature Struct. Biol. 1:221–225), resulting in the burial of 670 Å$^2$ of surface area on the peptide and 450 Å$^2$ on the SH3 domain. These interactions are very similar to those observed in the Src and Grb2/Sos complexes in the "minus" orientation (Goudreau et al., 1994, Nature Struct. Biol., 1:898–907, Terasawa et al., 1994, Nature Struct. Biol, 1:891–897, Lim et al., 1994, Nature, 372:375–379).

The ability of the polyproline helix to make equivalent hydrophobic interactions in either orientation is reflected by the close overlap between the residues at the $P_0$, $P_{+2}$ and $P_{+3}$; sites in the Abl/3BP1 complex ("plus" orientation) (Musacchio et al., 1994, Nature Struct. Biol., 1:546–551) and corresponding residues in the C3G peptide (FIG. 12). However, the Abl/3BP1 and Crk/C3G structures diverge significantly at the $P_{-3}$ site and beyond due to fundamentally different interactions in this region. The cleft between the RT and n-Src loops in Abl is hydrophobic, allowing the N-terminal hydrophobic region of the 3BP1 peptide to wrap around the SH3 domain in a non-helical conformation (Musacchio et al., 1994, Nature Struct. Biol., 1:546–551). The presence of five acidic residues in the RT and n-Src loops of the Crk SH3 domain would prevent the hydrophobic N-terminal end of the peptide from interacting in this region. Instead, the two lysines in the peptide are bound here, and make a number of hydrogen-bonding and packing interactions (FIG. 14A).

The Sos peptide is bound to Crk SH3-N in a very similar conformation as seen for the C3G peptide. There are six differences between the two peptides. The proline at position $P_{+4}$ in C3G is missing in Sos, proline is substituted for alanine at F+1, valine for leucine at $P_0$, arginine for lysine at $P_{-3}$ and $P_{-2}$ and an extra arginine is present after $P_{-4}$. The deviations in $C^\alpha$ positions between the two peptides range from 0.33 Å to 0.60 Å (Table 5), after the protein structures have been superimposed. Deformations in the Sos peptide with respect to the C3G peptide around the $P_0$ site result in a movement of the valine (in Sos) towards the SH3 surface, so that interactions are similar to that seen for the leucine side chain in C3G. Both structures overlap reasonably well with an ideal polyproline type II helix (Table 5). If the residues at positions $P_1$ to $P_{-2}$ are superimposed upon the ideal helix, the deviations in $C^\alpha$ positions between the ideal and actual helices range from 0.07 Å to 0.37 Å for these residues. The ends of the peptide are distorted away from the ideal helix by as much as 2.5 Å (Table 5), with the distortions resulting in an increase in the interactions with the SH3 surface.

TABLE 5

Statistics for the data collection and refinement.

| Data Collection Statistics | CrkSH3/C3G | CrkSH3/Sos |
|---|---|---|
| Space group | P4$_1$ | P4$_1$ |
| Unit Cell | a = 47.2Å, c = 29.4Å | a = 47.4Å, c = 29.5Å |
| Resolution Å | 20–1.50 | 20–1.90 |
| No. of observed reflections | 66,868 | 50,442 |
| No. of unique reflections | 10,512 | 5,289 |
| Completeness of data to 1.90Å | 89.1% | 95.5% |
| Completeness of data between 1.90–1.50Å | 73.8% | — |
| 1/σ(1) in all shell | 29.6 | 21.9 |
| 1/σ in outer shell | 16.6 | 5.4 |
| Rsym | 4.0% | 9.4% |
| Refinement Statistics | | |
| Rcrys [\|F\| > 2σ(F)] | 17.4% (6.0–1.50Å) | 18.3% (6.0–1.90Å) |
| No. of unique reflections [\|F\| > 2σ(F)] | 7667 | 4616 |
| No. of molecules in asymmetric unit | 1 | 1 |

TABLE 5-continued

Statistics for the data collection and refinement.

| Data Collection Statistics | CrkSH3/C3G | CrkSH3/Sos |
|---|---|---|
| No. of non-hydrogen atoms in final model | 664 | 608 |
| No. of water molecules in final model | 119 | 68 |
| Rms deviation of bond lengths (Å) | 0.012 | 0.011 |
| Rms deviations of angles (degrees) | 1.9 | 1.9 |

Lysine-specific interactions with the C3G peptide. There are four acidic residues in the RT loop of the murine c-Crk SH3-N domain: Asp 147, Glu 148, Glu 149, and Asp 150. Of these, Glu 148 points away from the peptide and does not participate directly in binding interactions. The other three residues approach each other closely, and present three oxygen atoms that form a nearly equilateral triangle (oxygen-oxygen distances range from 4.3 Å to 4.6 Å), with the lysine nitrogen at the geometric center and at a distance of 1.0 A from the plane of the oxygens (nitrogen-oxygen distances range from 2.7 Å to 2.8 Å). The binding site is thus remarkably well suited for interaction with lysine, since each of the three protons of the $sp^3$ hybridized amino group can be donated to carboxylate oxygens from Asp 147, Glu 149 and Asp 150 (FIG. 15). A stable interaction results, as suggested by the very high electron density level for the atoms of the lysine sidechain (FIG. 1) and by the low temperature factor of the terminal nitrogen atom (6.3 $Å^2$ compared to the sidechain average of 18 $Å^2$) and the oxygen atoms nearest to the nitrogen (6.3 $Å^2$ for Asp 150, 13.5 $Å2$ for both Asp 147 and Glu 149).

The lysine is in a fully extended conformation, and it approaches the triad of oxygen atoms directly from above, leading to near-optimal geometry for simultaneous hydrogen bonding in the trans, gauche+, and gauche− orientations (FIG. 15). In particular, each of the nitrogen-hydrogen bonds is almost co-planar with the corresponding carboxyl group, and the hydrogen-oxygen distances are within the range expected for tight hydrogen-bonding interactions (~1.8 Å, (Taylor & Kennard, 1984, Acc. Chem. Res., 17:320–326)). One feature that may be somewhat less than optimal is that N—H bonds approach residues Asp 147 and Glu 149 in the slightly less favored anti rather than syn orientation (FIG. 15) (Ippolito et al., 1990, J. Mol. Biol., 215:457–471). However, the C—O—H angles are consistent with the appropriate interactions between the hydrogen and the lone pair electrons of the oxygen in either the syn or anti orientation (Ippolito et al., 1990, J. Mol. Biol., 215:457–471).

This precise alignment of the lysine appears to be maintained by other interactions between the peptide and the SH3 domain. The polypeptide backbone of the peptide is held in place by the formation of a hydrogen bond between the sidechain of Glu 166 and the backbone amide nitrogen at position 9 of the peptide, and by a conserved hydrogen bond (Lim et al., 1994, Nature, 372:375–379) between the sidechain nitrogen of Trp 169 and the peptide carbonyl group at position 6 (FIG. 15). In addition, the methylene groups of the sidechain are tightly packed against the hydrophobic surface of the sidechain of Trp 169 (FIG. 15), with carbon-carbon distances of ~3.5 Å.

The lysine-carboxyl interaction is rarely seen in protein structures. The formation of simultaneous hydrogen bonds between a lysine sidechain and three carboxylate groups appeared to us to be an uncommon interaction, and so a systematic search of the entire protein databank was carried out for other instances of this interaction. For the purposes of this search, the "Lys/30" motif was defined as a cluster formed by the terminal nitrogen atom from a Lys sidechain (the NZ atom), and three oxygen atoms from the carboxyl groups of different Asp or Glu sidechains. The only geometric constraint placed on the search was that the three distances between the NZ and oxygen atoms be less than 3.7 Å. All instances of this motif in all 2943 release and pre-release coordinate sets deposited in the Brookhaven Protein Databank (Bernstein et al., 1978, Archives of Biochemistry & Biophysics, 185:584–91) on Nov. 1, 1994, were found by brute force search. No attempt was made to generate multisubunit complexes from the symmetry operations given for some coordinate sets, although inter subunit interactions within an asymmetric unit are included. The proteins with the Lys/30 motif were organized in families such that any two proteins from the same and different families had more and less than 30% sequence identity, respectively. Only one representative protein structure from each family was retained for further analysis.

This search of the entire contents of the protein databank resulted in the identification of only 10 unique protein structures in which a lysine amino nitrogen has hydrogen bonding interactions with three carboxyl oxygens, confirming that this motif is indeed extremely rare. The ten structures identified by this search are: glycogen phosphorylase (for example, protein databank entry 1abb (Leonidas et al., 1992, Protein Sci., 1:1112)), WV reverse transcriptase (entry 3hvt (Smerdon et al., 1994, Proc. Natl. Acad. Sci. (USA), 92:3911)), aspartate aminotransferase (entry 1asn (Jager et al., 1994, J. Mol. Biol., 239:285–305)), mengo virus coat protein (entry 2mev (Krishnaswamy & Rossmann, 1990, J. Mol. Biol., 211:803–844)), Chloromuconate cycloisomerase or muconate lactonizing enzyme (entry 1chr (Goldman et al., 1987, J. Mol. Biol., 194:143–153)), the nitrogenase Mo-Fe protein (entry 1min (Kim & Rees, 1992, Nature, 260)), chorismate mutase (entry 2cht (Chook et al., 1993, Proc. Natl. Acad. Sci. (USA), 90:8600)), xylose isomerase mutant (entry 1xyl (Allen, K. N., 1994, Biochemistry, 33:1488)), enolase (entry 4enl (Lebioda & Stec, 1991, Biochemistry, 30:2817)) and actinidin (entry 1aec (Baker, E. N, 1980, J. Mol. Biol., 141:441–484)). A detailed examination of these 10 structures revealed that in many cases the lysine is part of a network of basic and acidic residues which does not quite resemble the Lys-Glu-Asp interaction seen in the SH3 domain. In two others, there are clusters that resemble the SH3 Lys/30 motif (3hvt and 2cht), but they are in regions of the protein with high temperature factors. The cluster in actinidin does resemble the SH3 case closely, but here the lysine (Lys 17) has 4 potential ligands, including 3 glutamates and one serine, as well as an additional lysine that coordinates one of the glutamates (Baker, E. N, 1980, J. Mol. Biol., 141:441–484).

It is not surprising to find that protein structures do not normally bring three carboxyl groups close together without more than one compensating basic residue nearby. Indeed, the closest analogy to the SH3-lysine interaction may be the structure of a mutant xylose isomerase, with the lysine replacing the magnesium ion at a metal binding site of the enzyme (Allen, K. N., 1994, Biochemistry, 33:1488) (FIG. 18). In an interesting protein engineering experiment, a glutamate residue that is required for metal coordination in xylose isomerase was mutated to lysine, in order to abolish metal binding. There is little structural change induced in the protein as a consequence of this mutation, and the amino group of the lysine replaces the magnesium ion and coordinates two aspartates and one glutamate sidechain (Allen, K. N., 1994, Biochemistry, 33:1488). Although there is striking similarity between this interaction and that observed in the SH3-C3G complex, it is interesting to note that the orientation of the lysine residue in the mutant xylose isomerase is not as optimal as in the SH3 domain, since it approaches the triad of carboxyl groups at an angle and is not in a fully extended conformation (FIG. 18).

Interaction with Arginine at position P4 in the Sos Peptide. The binding mode of the Sos peptide is very similar to that seen with the C3G peptide (FIG. 12) and the arginine sidechain at $P_{-3}$ extends across the face of the Tip 169 sidechain and interacts with the acidic residues in the RT loop. However, a notable difference is that in contrast to lysine, the sidechain of the arginine is not well ordered and does not adopt an optimal conformation for hydrogen bonding interactions with the acidic groups or for hydrophobic interactions with the Tip sidechain. One terminal nitrogen of the arginine sidechain makes a strong hydrogen bond with Asp 150 (N-O distance of 2.4 Å). The second nitrogen interacts less optimally with Asp 147 (N-O distance of 3.1 Å), and the imino nitrogen does is not involved in hydrogen bonding interactions with the protein. Unlike the lysine in the C3G peptide, the arginine in Sos is not in the low energy extended conformation (the $X^3$ torsion angle is in a gauche conformation) and does not pack tightly against the tryptophan (the closest van der Waals contact is at 4.2 Å, in contrast to 3.5 Å in C3G). Finally, electron density for the arginine sidechain is relatively weak, indicating conformational flexibility.

The extent of conformational disorder in the two peptide complexes was estimated by carrying out a number of independent crystallographic refinements of the structures after the introduction of random perturbations in the atomic positions (FIG. 16) (Kuriyan et al., 1991, Proteins: Struct. Funct. Genet. 10:340–358). In order to make the comparisons meaningful, these refinements were carried out using data to 1.9 Å spacings for both complexes. Atomic positions in the RT loop and the $P_{-3}$ position of the peptide were randomly displaced such that the rms deviation from the starting model was ~1.7 Å. Many perturbed structures were generated independently in this way, and subjected to crystallographic refinement by least-squares. In order to increase the radius of convergence of the procedure, the refinements were initiated at 3.5 Å, with the resolution limit being gradually increased to 1.9 Å during the course of the refinement. Excessive shifts in water molecule positions were avoided by restraining the water oxygens to their original positions by harmonic constraints. A total of 1000 steps of conjugate gradient optimization were carried out. Refinements that failed to converge to R-values within 0.3 percentile points of the original value were rejected. A set of 24 structures were generated in this way for the two peptide complexes. A more exhaustive search procedure would be to use simulated annealing and multiple conformers for the protein (Kuriyan et al., 1991, Proteins: Struct. Funct. Genet. 10:340–358), but this was not attempted.

Despite the relatively large random shifts introduced into the structures prior to refinement, the amino group of the lysine as well as the carboxyl groups of the three acidic sidechains consistently return to their original positions and are thus quite precisely localized (FIG. 16). In contrast to the tight clustering of all 24 structures in the C3G complex, the arginine sidechain and the carboxyl groups are less well localized in the Crk/Sos complex (FIG. 16). The disorder in the arginine sidechain is probably underestimated by this method, since the electron density shows evidence for an alternative arginine conformation that is not picked up by the limited radius of convergence of the refinement method and that makes fewer hydrogen bonds that those depicted in FIG. 16.

These results demonstrate that the arginine sidechain in the crystal structure does not hydrogen bond with the sidechain of Glu 149 (FIG. 16). Most interestingly, in the viral oncogene product v-Crk SH3 domain the residue at the corresponding position is a glycine. This SH3 domain binds 13 times more weakly to the C3G peptide ($K_d$=25.5 $\mu$M) than does the c-Crk SH3-N, and also does not discriminate between lysine or arginine at the $P_{-3}$ position. The comparison of the binding modes of lysine and arginine (FIG. 16) explains this effect very nicely, since the loss of Glu 149 in v-Crk removes a sidechain that interacts with lysine, but not with arginine. Likewise, the loss of Glu 148 in Crk1 (FIG. 17), which is able to discriminate between lysine and arginine (Example 1, supra) is of no consequence since this sidechain points away from the binding site (FIG. 16).

Why does the lysine-containing C3G peptide bind so much more strongly to the Crk SH3 domain than to other SH3 domains such as Grb2? Ionic interactions do not often contribute much to protein stability, and are thought to be destabilizing in most situations relative to hydrophobic packing (Tidor & Karplus, 1991, Biochemistry, 30:3217–3228). However, the involvement of charged sidechains in protein complexes can assure specificity in the interaction, since the energetic penalty for desolvating the ions has to be compensated for, at least partially, through ion-pairing and hydrogen bonding. In comparing the affinity of the C3G peptides for Crk versus other SH3 domains, the extent to which the SH3 domain can compensate for the desolvation of lysine versus arginine has to be considered. Analysis of an extensive list of SH3 sequences shows that the presence of three acidic residues in the RT loop that can form the lysine-specific interaction is unique to c-Crk and its close relatives (see FIG. 17 for an alignment of a limited set of sequences). In the case of arginine binding to SH3 domains with one or two acidic sidechains in the RT loop, the guanidium group of the arginine is able to make two or three hydrogen bonding interactions with these sidechains (Lim et al., 1994, Nature, 372:375–379). Lysine, on the other hand, cannot make multiple hydrogen bonding interactions unless the carboxylate groups approach each other closely and in a relatively precise orientation, as seen in the Crk S113 domain structure.

Biological Significance. SH3 domains bind to peptides with a relatively small interaction surface, and without the benefit of the multiple hydrogen bonding interactions that anchor the phosphotyrosine sidechain to the SH2 domain. SH3-peptide interactions are therefore of low affinity (~1 $\mu$M in the best cases). The conserved framework of sidechains on the SH3 surface allows for efficient packing with polyproline type II helices, but the reliance on hydrophobic interactions, which are generally less specific than those that involve hydrogen bond formation, results in SH3-peptide recognition generally being promiscuous. Ion-pairing interactions between the peptide and the SH3 domain have been shown previously to be a mechanism for further increasing the specificity of the interaction, by selecting for one of two possible orientations of a sequence on the SH3 domain, with corresponding restrictions on the placement of non-proline residues (Feng et al., 1994, Science, 266:1241–1247, Goudreau et al., 1994, Nature Struct. Biol., 1:898–907, Terasawa et al., 1994, Nature Struct. Biol, 1:891–897, Lim et al., 1994, Nature, 372:375–379). However, in the general case where arginine residues in the peptide are used to form the ion-pairs, the presence of acidic patches on the surfaces of a large set of SH3 domains results in the binding of particular peptides, such as those from Sos, to a large number of SH3 domains with comparable affinity.

For many SH3 domains it may be the case that biological specificity is only achieved by exploiting multiple binding sites and by tertiary interactions with the parent protein and its target. However, proline-rich peptides from C3G are able to distinguish the Crk SH3 domain from a number of others by utilizing a lysine rather than an arginine at the key $P_{-3}$ position in the polyproline helix. The lysine-specific binding site seen in the Crk SH3 domain is extremely rare in protein structures, and it may have evolved in the SH3 domain because the limited sites of variability on the proline-rich peptide makes it advantageous to discriminate between lysine and arginine while exploiting electrostatic complementarity. As specific interactions between other SH3 domains and target peptides are discovered, subtle yet precise differences in their interactions may again turn out to be crucial in discriminating SH3 binding sites.

The present invention is not to be limited in scope by the specific embodiments described herein, since such embodiments are intended as but single illustrations of one aspect of the invention and any functionally equivalent embodiments are within the scope of this invention. Indeed, various modifications of the invention in addition to those shown and described herein will become apparent to those skilled in the art from the foregoing description and accompanying drawings. Such modifications are intended to fall within the scope of the appended claims.

It is also to be understood that all base pair sizes given for nucleotides are approximate and are used for the purpose of description.

Various references are cited herein, the disclosures of which are incorporated by reference herein in their entirety.

What is claimed is:

1. An isolated nucleic acid encoding an amino acid sequence comprising SEQ ID NO:19, SEQ ID NO:26, SEQ ID NO:27, SEQ ID NO:28, SEQ ID NO:29, SEQ ID NO:31, SEQ ID NO:34, SEQ ID NO:36, SEQ ID NO:37, SEQ ID NO:43 or SEQ ID NO:44.

2. The isolated nucleic acid of claim 1 which is a DNA.

3. A cloning vector which comprises the isolated nucleic acid of claim 2.

4. An expression vector which comprises the isolated nucleic acid of claim 2 operatively associated with an expression control sequence.

5. A bacterial cell transfected or transformed with the expression vector of claim 4.

6. A marntnalian cell transfected or transformed with the expression vector of claim 4.

7. The isolated nucleic acid of claim 1 wherein said amino acid sequence contains fewer than 100 amino acids.

8. The isolated nucleic acid of claim 7 wherein said amino acid sequence contains fewer than 50 amino acids.

9. A method of expressing a protein comprising the amino acid sequence of SEQ ID NO: 19, SEQ ID NO:26, SEQ ID NO:27, SEQ ID NO:28, SEQ ID NO:29, SEQ ID NO:31, SEQ ID NO:34, SEQ ID NO:36, SEQ ID NO:37, SEQ ID NO:43 or SEQ ID NO:44, comprising culturing a bacterial cell of claim 5 in an appropriate culture medium under conditions that provide for expression of the protein.

10. The method of claim 9 further comprising the step of purifying the protein.

* * * * *

SEQUENCE LISTING ( 1 ) GENERAL INFORMATION:

( i i i ) NUMBER OF SEQUENCES: 55

( 2 ) INFORMATION FOR SEQ ID NO:1:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:1:

Xaa   Pro   Xaa   Leu   Pro   Xaa   Lys   Xaa   Xaa
    1                             5

( 2 ) INFORMATION FOR SEQ ID NO:2:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:2:

Xaa   Pro   Xaa   Ile   Pro   Xaa   Lys   Xaa   Xaa
    1                             5

( 2 ) INFORMATION FOR SEQ ID NO:3:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:3:

Xaa Pro Xaa Val Pro Xaa Lys Xaa Xaa
1               5

( 2 ) INFORMATION FOR SEQ ID NO:4:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: internal ( v i i ) IMMEDIATE SOURCE:
        ( B ) CLONE: C3G/CB-1

( x i ) SEQUENCE DESCRIPTION: SEQ ID NO:4:

Ser Pro Pro Pro Ala Leu Pro Pro Lys Lys Arg Gln
1               5                   10

( 2 ) INFORMATION FOR SEQ ID NO:5:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: internal ( v i i ) IMMEDIATE SOURCE:
        ( B ) CLONE: C3G/CB-2

( x i ) SEQUENCE DESCRIPTION: SEQ ID NO:5:

Asp Thr Pro Pro Ala Leu Pro Glu Lys Lys Arg Arg
1               5                   10

( 2 ) INFORMATION FOR SEQ ID NO:6:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: internal ( v i i ) IMMEDIATE SOURCE:
        ( B ) CLONE: C3G/CB-3

( x i ) SEQUENCE DESCRIPTION: SEQ ID NO:6:

Glu Lys Pro Pro Pro Leu Pro Glu Lys Lys Asn Lys
1               5                   10

( 2 ) INFORMATION FOR SEQ ID NO:7:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: internal ( v i i ) IMMEDIATE SOURCE:
        ( B ) CLONE: C3G/CB-4

( x i ) SEQUENCE DESCRIPTION: SEQ ID NO:7:

```
Ala  Pro  Pro  Pro  Ala  Leu  Pro  Pro  Lys  Gln  Arg  Gln
1                  5                        10
```

( 2 ) INFORMATION FOR SEQ ID NO:8:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:8:

```
Pro  Pro  Ala  Leu  Pro  Glu  Lys  Lys  Arg
1                  5
```

( 2 ) INFORMATION FOR SEQ ID NO:9:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:9:

```
Pro  Pro  Ala  Leu  Pro  Pro  Lys  Lys  Arg
1                  5
```

( 2 ) INFORMATION FOR SEQ ID NO:10:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: internal ( v i i ) IMMEDIATE SOURCE:

(B) CLONE: ABL/CB-1

(x i) SEQUENCE DESCRIPTION: SEQ ID NO:10:

Leu Gln Ala Pro Glu Leu Pro Thr Lys Thr Arg Thr
1               5                   10

(2) INFORMATION FOR SEQ ID NO:11:

(i) SEQUENCE CHARACTERISTICS:
      (A) LENGTH: 12 amino acids
      (B) TYPE: amino acid
      (C) STRANDEDNESS: single
      (D) TOPOLOGY: linear (i i) MOLECULE TYPE: peptide (i i i) HYPOTHETICAL: NO (v) FRAGMENT TYPE: internal (v i i) IMMEDIATE SOURCE:
      (B) CLONE: ABL/CB-2

(x i) SEQUENCE DESCRIPTION: SEQ ID NO:11:

Ala Val Ser Pro Leu Leu Pro Arg Lys Glu Arg Gly
1               5                   10

(2) INFORMATION FOR SEQ ID NO:12:

(i) SEQUENCE CHARACTERISTICS:
      (A) LENGTH: 12 amino acids
      (B) TYPE: amino acid
      (C) STRANDEDNESS: single
      (D) TOPOLOGY: linear (i i) MOLECULE TYPE: peptide (i i i) HYPOTHETICAL: NO (v) FRAGMENT TYPE: internal (v i i) IMMEDIATE SOURCE:
      (B) CLONE: ARG/CB-1

(x i) SEQUENCE DESCRIPTION: SEQ ID NO:12:

Pro Arg Leu Pro Ile Leu Pro Ser Lys Thr Arg Thr
1               5                   10

(2) INFORMATION FOR SEQ ID NO:13:

(i) SEQUENCE CHARACTERISTICS:
      (A) LENGTH: 12 amino acids
      (B) TYPE: amino acid
      (C) STRANDEDNESS: single
      (D) TOPOLOGY: linear (i i) MOLECULE TYPE: peptide (i i i) HYPOTHETICAL: NO (v) FRAGMENT TYPE: internal (v i i) IMMEDIATE SOURCE:
      (B) CLONE: ARG/CB-2

(x i) SEQUENCE DESCRIPTION: SEQ ID NO:13:

Ser Gly Ser Pro Ala Leu Pro Arg Lys Gln Arg Asp
1               5                   10

(2) INFORMATION FOR SEQ ID NO:14:

(i) SEQUENCE CHARACTERISTICS:

( A ) LENGTH: 12 amino acids
                    ( B ) TYPE: amino acid
                    ( C ) STRANDEDNESS: single
                    ( D ) TOPOLOGY: linear ( i i ) MOLECULE TYPE: peptide ( i i i ) HYPOTHETICAL: NO ( v ) FRAGMENT TYPE: internal ( v i i ) IMMEDIATE SOURCE:
                    ( B ) CLONE: mSos1/P-1

( x i ) SEQUENCE DESCRIPTION: SEQ ID NO:14:

Pro   Val   Pro   Pro   Pro   Val   Pro   Pro   Arg   Arg   Glu   Pro
        1                       5                             10

( 2 ) INFORMATION FOR SEQ ID NO:15:

( i ) SEQUENCE CHARACTERISTICS:
                    ( A ) LENGTH: 12 amino acids
                    ( B ) TYPE: amino acid
                    ( C ) STRANDEDNESS: single
                    ( D ) TOPOLOGY: linear ( i i ) MOLECULE TYPE: peptide ( i i i ) HYPOTHETICAL: NO ( v ) FRAGMENT TYPE: internal ( v i i ) IMMEDIATE SOURCE:
                    ( B ) CLONE: mSos2/P-1

( x i ) SEQUENCE DESCRIPTION: SEQ ID NO:15:

Leu   Ile   Pro   Pro   Pro   Leu   Pro   Pro   Arg   Lys   Lys   Phe
        1                       5                             10

( 2 ) INFORMATION FOR SEQ ID NO:16:

( i ) SEQUENCE CHARACTERISTICS:
                    ( A ) LENGTH: 12 amino acids
                    ( B ) TYPE: amino acid
                    ( C ) STRANDEDNESS: single
                    ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:16:

Xaa   Xaa   Pro   Pro   Xaa   Leu   Pro   Xaa   Lys   Xaa   Arg   Xaa
        1                       5                             10

( 2 ) INFORMATION FOR SEQ ID NO:17:

( i ) SEQUENCE CHARACTERISTICS:
                    ( A ) LENGTH: 10 amino acids
                    ( B ) TYPE: amino acid
                    ( C ) STRANDEDNESS: single
                    ( D ) TOPOLOGY: linear ( i i ) MOLECULE TYPE: peptide ( i i i ) HYPOTHETICAL: NO ( v ) FRAGMENT TYPE: internal ( v i i ) IMMEDIATE SOURCE:
                    ( B ) CLONE: CB-1

(x i) SEQUENCE DESCRIPTION: SEQ ID NO:17:

```
Pro  Pro  Pro  Ala  Leu  Pro  Pro  Lys  Lys  Arg
1                  5                       10
```

(2) INFORMATION FOR SEQ ID NO:18:

(i) SEQUENCE CHARACTERISTICS:
        (A) LENGTH: 10 amino acids
        (B) TYPE: amino acid
        (C) STRANDEDNESS: single
        (D) TOPOLOGY: linear (i i) MOLECULE TYPE: peptide (i i i) HYPOTHETICAL: NO (v) FRAGMENT TYPE: internal (v i i) IMMEDIATE SOURCE:
        (B) CLONE: CB-1

(x i) SEQUENCE DESCRIPTION: SEQ ID NO:18:

```
Thr  Pro  Pro  Ala  Leu  Pro  Glu  Lys  Lys  Arg
1                  5                       10
```

(2) INFORMATION FOR SEQ ID NO:19:

(i) SEQUENCE CHARACTERISTICS:
        (A) LENGTH: 10 amino acids
        (B) TYPE: amino acid
        (C) STRANDEDNESS: single
        (D) TOPOLOGY: linear (i i) MOLECULE TYPE: peptide (i i i) HYPOTHETICAL: NO (v) FRAGMENT TYPE: internal (v i i) IMMEDIATE SOURCE:
        (B) CLONE: CB-3

(x i) SEQUENCE DESCRIPTION: SEQ ID NO:19:

```
Lys  Pro  Pro  Pro  Leu  Pro  Glu  Lys  Lys  Gln
1                  5                       10
```

(2) INFORMATION FOR SEQ ID NO:20:

(i) SEQUENCE CHARACTERISTICS:
        (A) LENGTH: 10 amino acids
        (B) TYPE: amino acid
        (C) STRANDEDNESS: single
        (D) TOPOLOGY: linear (i i) MOLECULE TYPE: peptide (i i i) HYPOTHETICAL: NO (v) FRAGMENT TYPE: internal (v i i) IMMEDIATE SOURCE:
        (B) CLONE: CB-4

(x i) SEQUENCE DESCRIPTION: SEQ ID NO:20:

```
Pro  Pro  Pro  Ala  Leu  Pro  Pro  Lys  Gln  Arg
1                  5                       10
```

(2) INFORMATION FOR SEQ ID NO:21:

(i) SEQUENCE CHARACTERISTICS:
        (A) LENGTH: 12 amino acids
        (B) TYPE: amino acid ( C ) STRANDEDNESS: single
( D ) TOPOLOGY: linear ( i i ) MOLECULE TYPE: peptide ( i i i ) HYPOTHETICAL: NO ( v ) FRAGMENT TYPE: internal ( v i i ) IMMEDIATE SOURCE:
( B ) CLONE: GST-1-12

( x i ) SEQUENCE DESCRIPTION: SEQ ID NO:21:

Asn Ser Pro Pro Pro Ala Leu Pro Pro Lys Lys Arg
1               5                           10

( 2 ) INFORMATION FOR SEQ ID NO:22:

( i ) SEQUENCE CHARACTERISTICS:
( A ) LENGTH: 9 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( v ) FRAGMENT TYPE: internal ( v i i ) IMMEDIATE SOURCE:
( B ) CLONE: GST-3-11

( x i ) SEQUENCE DESCRIPTION: SEQ ID NO:22:

Pro Pro Pro Ala Leu Pro Pro Lys Lys
1               5

( 2 ) INFORMATION FOR SEQ ID NO:23:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( v ) FRAGMENT TYPE: internal ( v i i ) IMMEDIATE SOURCE:
( B ) CLONE: GST-5-12

( x i ) SEQUENCE DESCRIPTION: SEQ ID NO:23:

Pro Ala Leu Pro Pro Lys Lys Arg
1               5

( 2 ) INFORMATION FOR SEQ ID NO:24:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( v ) FRAGMENT TYPE: internal ( v i i ) IMMEDIATE SOURCE:
( B ) CLONE: GST-3-12 P5A, P8A ( x i ) SEQUENCE DESCRIPTION: SEQ ID NO:24:

Pro Pro Ala Ala Leu Ala Pro Lys Lys Arg
1               5                   10

( 2 ) INFORMATION FOR SEQ ID NO:25:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: internal ( v i i ) IMMEDIATE SOURCE:
        ( B ) CLONE: GST-1-12 K10L ( x i ) SEQUENCE DESCRIPTION: SEQ ID NO:25:

Pro Pro Pro Ala Leu Pro Pro Leu Lys Arg
1               5                   10

( 2 ) INFORMATION FOR SEQ ID NO:26:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: internal ( v i i ) IMMEDIATE SOURCE:
        ( B ) CLONE: GST-3-12 R12N ( x i ) SEQUENCE DESCRIPTION: SEQ ID NO:26:

Pro Pro Pro Ala Leu Pro Pro Lys Lys Asn
1               5                   10

( 2 ) INFORMATION FOR SEQ ID NO:27:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: internal ( v i i ) IMMEDIATE SOURCE:
        ( B ) CLONE: GST-4-12 R12N ( x i ) SEQUENCE DESCRIPTION: SEQ ID NO:27:

Pro Pro Ala Leu Pro Pro Lys Lys Asn
1               5

( 2 ) INFORMATION FOR SEQ ID NO:28:

( i ) SEQUENCE CHARACTERISTICS:
        ( A ) LENGTH: 10 amino acids (B) TYPE: amino acid
            (C) STRANDEDNESS: single
            (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:28:

Ala  Pro  Pro  Ala  Leu  Pro  Pro  Lys  Lys  Arg
    1                   5                        10

(2) INFORMATION FOR SEQ ID NO:29:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:29:

Pro  Ala  Pro  Ala  Leu  Pro  Pro  Lys  Lys  Arg
    1                   5                        10

(2) INFORMATION FOR SEQ ID NO:30:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:30:

Ala  Pro  Ala  Ala  Leu  Pro  Pro  Lys  Lys  Arg
    1                   5                        10

(2) INFORMATION FOR SEQ ID NO:31:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (iii) HYPOTHETICAL: NO (v) FRAGMENT TYPE: internal (vii) IMMEDIATE SOURCE:
            (B) CLONE: C3G mut(1)

(xi) SEQUENCE DESCRIPTION: SEQ ID NO:31:

Pro  Pro  Pro  Pro  Leu  Pro  Pro  Lys  Lys  Arg
    1                   5                        10

(2) INFORMATION FOR SEQ ID NO:32:

( i ) SEQUENCE CHARACTERISTICS:
 ( A ) LENGTH: 10 amino acids
 ( B ) TYPE: amino acid
 ( C ) STRANDEDNESS: single
 ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:32:

```
Ala  Pro  Pro  Ala  Ala  Pro  Pro  Lys  Lys  Arg
1                 5                           10
```

( 2 ) INFORMATION FOR SEQ ID NO:33:

( i ) SEQUENCE CHARACTERISTICS:
 ( A ) LENGTH: 10 amino acids
 ( B ) TYPE: amino acid
 ( C ) STRANDEDNESS: single
 ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:33:

```
Pro  Pro  Pro  Ala  Leu  Ala  Pro  Lys  Lys  Arg
1                 5                           10
```

( 2 ) INFORMATION FOR SEQ ID NO:34:

( i ) SEQUENCE CHARACTERISTICS:
 ( A ) LENGTH: 10 amino acids
 ( B ) TYPE: amino acid
 ( C ) STRANDEDNESS: single
 ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:34:

```
Ala  Pro  Pro  Ala  Leu  Pro  Ala  Lys  Lys  Arg
1                 5                           10
```

( 2 ) INFORMATION FOR SEQ ID NO:35:

( i ) SEQUENCE CHARACTERISTICS:
 ( A ) LENGTH: 10 amino acids
 ( B ) TYPE: amino acid
 ( C ) STRANDEDNESS: single
 ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:35:

```
Pro  Pro  Pro  Ala  Leu  Pro  Pro  Ala  Lys  Arg
1                 5                           10
```

( 2 ) INFORMATION FOR SEQ ID NO:36:

( i ) SEQUENCE CHARACTERISTICS:
   ( A ) LENGTH: 10 amino acids
   ( B ) TYPE: amino acid
   ( C ) STRANDEDNESS: single
   ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:36:

Ala Pro Pro Ala Leu Pro Pro Lys Ala Arg
1               5                   10

( 2 ) INFORMATION FOR SEQ ID NO:37:

( i ) SEQUENCE CHARACTERISTICS:
      ( A ) LENGTH: 10 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:37:

Pro Pro Pro Ala Leu Pro Pro Lys Lys Ala
1               5                   10

( 2 ) INFORMATION FOR SEQ ID NO:38:

( i ) SEQUENCE CHARACTERISTICS:
      ( A ) LENGTH: 10 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( v ) FRAGMENT TYPE: internal ( v i i ) IMMEDIATE SOURCE:
      ( B ) CLONE: SOS-1

( x i ) SEQUENCE DESCRIPTION: SEQ ID NO:38:

Pro Pro Pro Val Pro Pro Arg Arg Arg Arg
1               5                   10

( 2 ) INFORMATION FOR SEQ ID NO:39:

( i ) SEQUENCE CHARACTERISTICS:
      ( A ) LENGTH: 10 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( v ) FRAGMENT TYPE: internal ( v i i ) IMMEDIATE SOURCE:
      ( B ) CLONE: SOS-2

( x i ) SEQUENCE DESCRIPTION: SEQ ID NO:39:

Pro Pro Ala Ile Pro Pro Arg Gln Pro Thr
1               5                    10

(2) INFORMATION FOR SEQ ID NO:40:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vii) IMMEDIATE SOURCE:
        (A) CLONE: SOS-3

(xi) SEQUENCE DESCRIPTION: SEQ ID NO:40:

Pro Pro Leu Leu Pro Pro Arg Gln Pro Val
1               5                    10

(2) INFORMATION FOR SEQ ID NO:41:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vii) IMMEDIATE SOURCE:
        (A) CLONE: SOS-4

(xi) SEQUENCE DESCRIPTION: SEQ ID NO:41:

Gly Pro Pro Val Pro Pro Arg Gln Ser Thr
1               5                    10

(2) INFORMATION FOR SEQ ID NO:42:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vii) IMMEDIATE SOURCE:
        (A) LIBRARY: C3G mut(2)

(xi) SEQUENCE DESCRIPTION: SEQ ID NO:42:

Pro Pro Pro Ala Leu Pro Pro Arg Lys Arg
1               5                    10

(2) INFORMATION FOR SEQ ID NO:43:

(i) SEQUENCE CHARACTERISTICS:
        (A) LENGTH: 10 amino acids
        (B) TYPE: amino acid
        (C) STRANDEDNESS: single (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:43:

```
Pro  Pro  Pro  Ala  Leu  Pro  Pro  Lys  Ala  Arg
1                 5                         10
```

(2) INFORMATION FOR SEQ ID NO:44:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:44:

```
Pro  Pro  Pro  Ala  Leu  Pro  Pro  Lys  Lys  Lys
1                 5                         10
```

(2) INFORMATION FOR SEQ ID NO:45:

(i) SEQUENCE CHARACTERISTICS:
(A) LENGTH: 1077 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:45:

```
Met  Asp  Thr  Asp  Ser  Gln  Arg  Ser  His  Leu  Ser  Ser  Phe  Thr  Met  Lys
1                 5                         10                        15

Leu  Met  Asp  Lys  Pro  His  Ser  Pro  Lys  Ile  Lys  Arg  Thr  Pro  Ser  Lys
                 20                        25                        30

Lys  Gly  Lys  Phe  Ala  Glu  Val  Ser  Val  Lys  Ile  Pro  Glu  Lys  Pro  Val
            35                        40                        45

Asn  Lys  Glu  Ala  Thr  Asp  Arg  Phe  Leu  Pro  Glu  Gly  Tyr  Pro  Leu  Pro
       50                        55                        60

Leu  Asp  Leu  Glu  Gln  Gln  Ala  Val  Glu  Phe  Met  Ser  Thr  Ser  Ala  Val
65                        70                        75                        80

Ala  Ser  Arg  Ser  Gln  Arg  Gln  Lys  Asn  Leu  Ser  Trp  Leu  Glu  Glu  Lys
                      85                        90                        95

Glu  Lys  Glu  Val  Val  Ser  Ala  Leu  Arg  Tyr  Phe  Lys  Thr  Ile  Val  Asp
                 100                       105                       110

Lys  Met  Ala  Ile  Asp  Lys  Lys  Val  Leu  Glu  Met  Leu  Pro  Gly  Ser  Ala
            115                       120                       125

Ser  Lys  Val  Leu  Glu  Ala  Ile  Leu  Arg  Leu  Val  Gln  Asn  Asp  Pro  Arg
       130                       135                       140

Ile  Gln  His  Ser  Ser  Ala  Leu  Ser  Ser  Cys  Tyr  Ser  Arg  Val  Tyr  Gln
145                       150                       155                       160

Ser  Leu  Ala  Asn  Leu  Ile  Arg  Trp  Ser  Asp  Gln  Val  Met  Leu  Glu  Gly
                 165                       170                       175
```

```
Val  Asn  Ser  Glu  Asp  Lys  Gly  Met  Val  Thr  Thr  Val  Lys  Gly  Val  Ile
              180                      185                      190

Lys  Ala  Val  Leu  Asp  Gly  Val  Leu  Glu  Leu  Val  Arg  Leu  Thr  Ile  Glu
              195                      200                      205

Lys  Gln  Gly  Arg  Pro  Ser  Pro  Thr  Cys  Pro  Val  Lys  Pro  Ser  Ser  Pro
              210                      215                      220

Ala  Ser  Lys  Pro  Asp  Gly  Pro  Ala  Glu  Leu  Pro  Leu  Thr  Asp  Arg  Glu
225                           230                      235                      240

Val  Glu  Ile  Leu  Asn  Lys  Thr  Thr  Gly  Met  Ser  Gln  Ser  Ser  Glu  Leu
              245                      250                      255

Leu  Pro  Asp  Ala  Thr  Asp  Glu  Glu  Val  Ala  Pro  Pro  Lys  Pro  Pro  Leu
              260                      265                      270

Pro  Gly  Ile  Arg  Val  Val  Asp  Asn  Ser  Pro  Pro  Pro  Ala  Leu  Pro  Pro
              275                      280                      285

Lys  Lys  Arg  Gln  Ser  Ala  Pro  Ser  Pro  Thr  Arg  Val  Ala  Val  Val  Ala
              290                      295                      300

Pro  Met  Ser  Arg  Ala  Thr  Ser  Gly  Ser  Ser  Leu  Pro  Val  Gly  Ile  Asn
305                           310                      315                      320

Arg  Gln  Asp  Phe  Asp  Val  Asp  Cys  Tyr  Ala  Gln  Arg  Arg  Leu  Ser  Gly
              325                      330                      335

Gly  Ser  His  Ser  Tyr  Gly  Gly  Glu  Ser  Pro  Arg  Leu  Ser  Pro  Cys  Ser
              340                      345                      350

Ser  Ile  Gly  Lys  Leu  Ser  Lys  Ser  Asp  Glu  Gln  Leu  Ser  Ser  Leu  Asp
              355                      360                      365

Arg  Asp  Ser  Gly  Gln  Cys  Ser  Arg  Asn  Thr  Ser  Cys  Glu  Thr  Leu  Asp
              370                      375                      380

His  Tyr  Asp  Pro  Asp  Tyr  Glu  Phe  Leu  Gln  Gln  Asp  Leu  Ser  Asn  Ala
385                           390                      395                      400

Asp  Gln  Ile  Pro  Gln  Gln  Thr  Ala  Trp  Asn  Leu  Ser  Pro  Leu  Pro  Glu
              405                      410                      415

Ser  Leu  Gly  Glu  Ser  Gly  Ser  Pro  Phe  Leu  Gly  Pro  Pro  Phe  Gln  Leu
              420                      425                      430

Pro  Leu  Gly  Gly  His  Pro  Gln  Pro  Asp  Gly  Pro  Leu  Ala  Pro  Gly  Gln
              435                      440                      445

Gln  Thr  Asp  Thr  Pro  Pro  Ala  Leu  Pro  Lys  Lys  Lys  Arg  Arg  Ser  Ala
              450                      455                      460

Ala  Ser  Gln  Thr  Ala  Asp  Gly  Ser  Gly  Cys  Arg  Val  Ser  Tyr  Glu  Arg
465                           470                      475                      480

His  Pro  Ser  Gln  Tyr  Asp  Asn  Ile  Ser  Gly  Glu  Asp  Leu  Gln  Ser  Thr
              485                      490                      495

Ala  Pro  Ile  Pro  Ser  Val  Pro  Tyr  Ala  Pro  Phe  Ala  Ala  Ile  Leu  Pro
              500                      505                      510

Phe  Gln  His  Gly  Gly  Ser  Ser  Ala  Pro  Val  Glu  Phe  Val  Gly  Asp  Phe
              515                      520                      525

Thr  Ala  Pro  Glu  Ser  Thr  Gly  Asp  Pro  Glu  Lys  Pro  Pro  Pro  Leu  Pro
              530                      535                      540

Glu  Lys  Lys  Gln  Lys  His  Met  Leu  Ala  Tyr  Met  Gln  Leu  Leu  Glu  Asp
545                           550                      555                      560

Tyr  Ser  Glu  Pro  Gln  Pro  Ser  Met  Phe  Tyr  Gln  Thr  Pro  Gln  Asn  Glu
              565                      570                      575

His  Ile  Tyr  Gln  Gln  Lys  Met  Lys  Leu  Leu  Met  Glu  Val  Tyr  Gly  Phe
              580                      585                      590
```

```
Ser  Asp  Ser  Phe  Ser  Gly  Val  Asp  Ser  Val  Gln  Glu  Leu  Ala  Pro  Pro
          595                 600                      605

Pro  Ala  Leu  Pro  Pro  Ala  Gln  Arg  Gln  Leu  Glu  Pro  Pro  Ala  Gly  Lys
          610                 615                      620

Asp  Gly  His  Pro  Arg  Asp  Pro  Ser  Ala  Val  Ser  Val  Val  Pro  Gly  Lys
625                           630                 635                      640

Asp  Ser  Arg  Asp  Gly  Ser  Glu  Arg  Ala  Pro  Lys  Asp  Pro  Asp  Ala  Leu
                    645                      650                      655

Glu  Ser  Ala  Gln  Ser  Glu  Glu  Glu  Val  Asp  Glu  Leu  Ser  Leu  Ile  Asp
               660                      665                 670

His  Asn  Glu  Ile  Met  Ser  Arg  Leu  Thr  Leu  Lys  Gln  Glu  Gly  Asp  Asp
          675                      680                 685

Gly  Pro  Asp  Val  Arg  Gly  Gly  Ser  Gly  Asn  Ile  Leu  Leu  Val  His  Ala
     690                      695                      700

Thr  Glu  Thr  Asp  Arg  Lys  Asp  Leu  Val  Leu  Tyr  Cys  Glu  Ala  Phe  Leu
705                           710                 715                      720

Thr  Thr  Tyr  Arg  Thr  Phe  Ile  Ser  Pro  Glu  Glu  Leu  Ile  Lys  Lys  Leu
                    725                 730                      735

Gln  Tyr  Arg  Tyr  Glu  Lys  Phe  Ser  Pro  Phe  Ala  Asp  Thr  Phe  Lys  Lys
               740                 745                      750

Arg  Val  Ser  Lys  Asn  Thr  Phe  Phe  Val  Leu  Val  Arg  Val  Val  Asp  Glu
          755                      760                 765

Leu  Cys  Leu  Val  Glu  Leu  Thr  Glu  Glu  Ile  Leu  Lys  Leu  Leu  Met  Glu
     770                      775                 780

Leu  Val  Phe  Arg  Leu  Val  Cys  Asn  Gln  Glu  Leu  Ser  Leu  Ala  Arg  Val
785                      790                 795                           800

Leu  Arg  Lys  Asn  Ile  Leu  Asp  Lys  Val  Asp  Gln  Lys  Lys  Leu  Leu  Arg
                    805                 810                      815

Cys  Ala  Thr  Ser  Ser  Gln  Pro  Leu  Ala  Ala  Arg  Gly  Val  Ala  Ala  Arg
               820                      825                 830

Pro  Gly  Thr  Leu  His  Asp  Phe  His  Ser  His  Glu  Ile  Ala  Asp  Glu  Leu
               835                 840                      845

Thr  Leu  Leu  Asp  Ala  Glu  Leu  Phe  Tyr  Lys  Ile  Glu  Ile  Pro  Glu  Val
     850                      855                 860

Leu  Leu  Trp  Ala  Lys  Glu  Gln  Asn  Glu  Glu  Lys  Ser  Pro  Asn  Leu  Thr
865                      870                 875                           880

Gln  Phe  Thr  Glu  His  Phe  Asn  Asn  Met  Ser  Tyr  Trp  Val  Arg  Ser  Ile
                    885                 890                      895

Ile  Met  Leu  Gln  Glu  Lys  Ala  Gln  Asp  Arg  Glu  Arg  Leu  Leu  Leu  Lys
               900                 905                      910

Phe  Ile  Lys  Ile  Met  Lys  His  Leu  Arg  Lys  Leu  Asn  Asn  Phe  Asn  Ser
          915                      920                 925

Tyr  Leu  Ala  Ile  Leu  Ser  Ala  Leu  Asp  Ser  Ala  Pro  Ile  Arg  Arg  Leu
     930                      935                 940

Glu  Trp  Gln  Lys  Gln  Thr  Ser  Glu  Gly  Leu  Ala  Glu  Tyr  Cys  Thr  Leu
945                      950                 955                           960

Ile  Asp  Ser  Ser  Ser  Ser  Phe  Arg  Ala  Tyr  Arg  Ala  Ala  Leu  Ser  Glu
                    965                 970                      975

Val  Glu  Pro  Pro  Cys  Ile  Pro  Tyr  Leu  Gly  Leu  Ile  Leu  Gln  Asp  Leu
               980                 985                      990

Thr  Phe  Val  His  Leu  Gly  Asn  Pro  Asp  Tyr  Ile  Asp  Gly  Lys  Val  Asn
          995                      1000                1005

Phe  Ser  Lys  Arg  Trp  Gln  Gln  Phe  Asn  Ile  Leu  Asp  Ser  Met  Arg  Cys
     1010                     1015                1020
```

Phe Gln Gln Ala His Tyr Asp Met Arg Arg Asn Asp Asp Ile Ile Asn
1025                    1030                1035                    1040

Phe Phe Asn Asp Phe Ser Asp His Leu Ala Glu Glu Ala Leu Trp Glu
                1045            1050                1055

Leu Ser Leu Lys Ile Lys Pro Arg Asn Ile Thr Arg Arg Lys Thr Asp
                1060            1065                1070

Arg Glu Glu Lys Thr
        1075

( 2 ) INFORMATION FOR SEQ ID NO:46:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: internal ( v i i ) IMMEDIATE SOURCE:
        ( B ) CLONE: crk3N ( x i ) SEQUENCE DESCRIPTION: SEQ ID NO:46:

Ala Glu Tyr Val Arg Ala Leu Phe Asp Phe Asn Gly Asn Asp Glu Glu
1               5               10                  15

Asp Leu Pro Phe Lys Lys Gly Asp Ile Leu Arg Ile Arg Asp Lys Pro
                20              25                  30

Glu Glu Gln Trp Trp Asn Ala Glu Asp Ser Glu Gly Lys Arg Gly Met
        35              40                  45

Ile Pro Val Pro Tyr Val Glu Lys Tyr Arg
        50              55

( 2 ) INFORMATION FOR SEQ ID NO:47:

( i ) SEQUENCE CHARACTERISTICS:
        ( A ) LENGTH: 56 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: internal ( v i i ) IMMEDIATE SOURCE:
        ( B ) CLONE: v-crk ( x i ) SEQUENCE DESCRIPTION: SEQ ID NO:47:

Val Glu Tyr Val Arg Ala Leu Phe Asp Phe Lys Gly Asn Asp Asp Gly
1               5               10                  15

Asp Leu Pro Phe Lys Lys Gly Asp Ile Leu Lys Ile Arg Asp Lys Pro
                20              25                  30

Glu Glu Gln Trp Trp Asn Ala Glu Asp Met Asp Gly Lys Arg Gly Met
        35              40                  45

Ile Pro Val Pro Tyr Glu Lys Cys
        50              55

( 2 ) INFORMATION FOR SEQ ID NO:48:

( i ) SEQUENCE CHARACTERISTICS:
  ( A ) LENGTH: 57 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: NO ( v ) FRAGMENT TYPE: internal ( v i i ) IMMEDIATE SOURCE:
  ( B ) CLONE: crk1

( x i ) SEQUENCE DESCRIPTION: SEQ ID NO:48:

Leu Glu Tyr Val Arg Thr Leu Tyr Asp Phe Pro Gly Asn Asp Ala Glu
1               5                   10                  15

Asp Leu Pro Phe Lys Lys Gly Glu Ile Leu Val Ile Ile Glu Lys Pro
            20                  25                  30

Glu Glu Gln Trp Trp Ser Ala Arg Asn Lys Asp Gly Arg Val Gly Met
        35                  40                  45

Ile Pro Val Pro Tyr Val Glu Lys Leu
        50                  55

( 2 ) INFORMATION FOR SEQ ID NO:49:

( i ) SEQUENCE CHARACTERISTICS:
    ( A ) LENGTH: 61 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( v ) FRAGMENT TYPE: internal ( v i i ) IMMEDIATE SOURCE:
    ( B ) CLONE: nck3A ( x i ) SEQUENCE DESCRIPTION: SEQ ID NO:49:

Ala Glu Glu Val Val Val Val Ala Lys Phe Asp Tyr Val Ala Gln Gln
1               5                   10                  15

Glu Gln Glu Leu Asp Ile Lys Lys Asn Glu Arg Leu Trp Leu Leu Asp
            20                  25                  30

Asp Ser Lys Ser Trp Trp Arg Val Arg Asn Ser Met Asn Lys Thr Gly
        35                  40                  45

Phe Val Pro Ser Asn Tyr Val Glu Arg Lys Asn Ser Ala
        50                  55                  60

( 2 ) INFORMATION FOR SEQ ID NO:50:

( i ) SEQUENCE CHARACTERISTICS:
    ( A ) LENGTH: 57 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( v ) FRAGMENT TYPE: internal ( v i i ) IMMEDIATE SOURCE:
    ( B ) CLONE: lck ( x i ) SEQUENCE DESCRIPTION: SEQ ID NO:50:

Asp Asn Leu Val Ile Ala Leu His Ser Tyr Glu Pro Ser His Asp Gly
1               5                       10                      15

Asp Leu Gly Phe Glu Lys Gly Glu Gln Leu Arg Ile Leu Glu Gln Ser
            20                  25                      30

Gly Glu Trp Trp Lys Ala Gln Ser Leu Thr Thr Gly Gln Glu Gly Phe
            35              40                      45

Glu Pro Phe Asn Phe Val Ala Lys Ala
        50              55

(2) INFORMATION FOR SEQ ID NO:51:

(i) SEQUENCE CHARACTERISTICS:
        (A) LENGTH: 59 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vii) IMMEDIATE SOURCE:
        (B) CLONE: fyn (xi) SEQUENCE DESCRIPTION: SEQ ID NO:51:

Val Thr Leu Phe Val Ala Leu Tyr Asp Tyr Glu Ala Arg Thr Gly Asp
1               5                       10                      15

Asp Leu Ser Phe His Lys Gly Glu Lys Phe Gln Ile Leu Asn Ser Ser
            20                  25                      30

Glu Gly Asp Trp Trp Glu Ala Arg Ser Leu Thr Thr Gly Glu Thr Gly
            35              40                      45

Tyr Ile Pro Ser Asn Tyr Val Ala Pro Val Asp
        50              55

(2) INFORMATION FOR SEQ ID NO:52:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vii) IMMEDIATE SOURCE:
        (B) CLONE: spec (xi) SEQUENCE DESCRIPTION: SEQ ID NO:52:

Asp Glu Thr Gly Lys Glu Leu Val Leu Ala Leu Tyr Asp Tyr Gln Glu
1               5                       10                      15

Lys Ser Pro Arg Glu Val Thr Met Lys Lys Gly Asp Ile Leu Thr Leu
            20                  25                      30

Leu Asn Ser Thr Asn Lys Asp Trp Trp Lys Val Glu Val Asn Asp Arg
            35              40                      45

Gln Gly Phe Val Pro Ala Ala Tyr Val Lys Lys Leu Asp
        50              55                  60

(2) INFORMATION FOR SEQ ID NO:53:

( i ) SEQUENCE CHARACTERISTICS:
  ( A ) LENGTH: 58 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: NO ( v ) FRAGMENT TYPE: internal ( v i i ) IMMEDIATE SOURCE:
  ( B ) CLONE: abl ( x i ) SEQUENCE DESCRIPTION: SEQ ID NO:53:

| Leu | Phe | Val | Ala | Leu | Tyr | Asp | Phe | Val | Ala | Ser | Gly | Asp | Asn | Thr | Leu |
|---|---|---|---|---|---|---|---|---|---|---|---|---|---|---|---|
| 1 | | | | 5 | | | | | 10 | | | | | 15 | |
| Ser | Ile | Thr | Lys | Gly | Glu | Lys | Leu | Arg | Val | Leu | Gly | Tyr | Asn | His | Asn |
| | | | 20 | | | | | 25 | | | | | 30 | | |
| Gly | Glu | Trp | Cys | Glu | Ala | Gln | Thr | Lys | Asn | Gly | Gln | Gly | Trp | Val | Pro |
| | | 35 | | | | | 40 | | | | | 45 | | | |
| Ser | Asn | Tyr | Ile | Thr | Pro | Val | Asn | Ser | Leu | | | | | | |
| | 50 | | | | | 55 | | | | | | | | | |

( 2 ) INFORMATION FOR SEQ ID NO:54:

( i ) SEQUENCE CHARACTERISTICS:
    ( A ) LENGTH: 59 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( v ) FRAGMENT TYPE: internal ( v i i ) IMMEDIATE SOURCE:
    ( B ) CLONE: grb2N ( x i ) SEQUENCE DESCRIPTION: SEQ ID NO:54:

| Met | Glu | Ala | Ile | Ala | Lys | Tyr | Asp | Phe | Lys | Ala | Thr | Ala | Asp | Asp | Glu |
|---|---|---|---|---|---|---|---|---|---|---|---|---|---|---|---|
| 1 | | | | 5 | | | | | 10 | | | | | 15 | |
| Leu | Ser | Phe | Lys | Arg | Gly | Asp | Ile | Leu | Lys | Val | Leu | Asn | Glu | Glu | Cys |
| | | | 20 | | | | | 25 | | | | | 30 | | |
| Asp | Gln | Asn | Trp | Tyr | Lys | Ala | Glu | Leu | Asn | Gly | Lys | Asp | Gly | Phe | Ile |
| | | | 35 | | | | | 40 | | | | | 45 | | |
| Pro | Lys | Asn | Tyr | Ile | Glu | Met | Lys | Pro | His | Pro | | | | | |
| | 50 | | | | | 55 | | | | | | | | | |

( 2 ) INFORMATION FOR SEQ ID NO:55:

( i ) SEQUENCE CHARACTERISTICS:
    ( A ) LENGTH: 80 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( v ) FRAGMENT TYPE: internal ( v i i ) IMMEDIATE SOURCE:
    ( B ) CLONE: PI3Kb ( x i ) SEQUENCE DESCRIPTION: SEQ ID NO:55:

| | | | | | | | | | | | | | | | |
|---|---|---|---|---|---|---|---|---|---|---|---|---|---|---|---|
| Met 1 | Ser | Ala | Glu | Gly 5 | Tyr | Gln | Tyr | Arg | Ala 10 | Leu | Tyr | Asp | Tyr | Lys 15 | Lys |
| Glu | Arg | Glu | Glu 20 | Asp | Ile | Asp | Leu | His 25 | Leu | Gly | Asp | Ile | Leu 30 | Thr | Val |
| Asn | Lys | Gly 35 | Ser | Leu | Val | Ala | Leu 40 | Gly | Phe | Ser | Asp | Gly 45 | Gln | Glu | Ala |
| Arg | Pro 50 | Glu | Glu | Ile | Gly | Trp 55 | Leu | Asn | Gly | Tyr | Asn 60 | Glu | Thr | Thr | Gly |
| Glu 65 | Arg | Gly | Asp | Phe | Pro 70 | Gly | Thr | Tyr | Val | Glu 75 | Tyr | Ile | Gly | Arg | Lys 80 |